United States Patent [19]

Muraoka et al.

[11] Patent Number: 5,556,860
[45] Date of Patent: Sep. 17, 1996

[54] QUINAZOLINONE DERIVATIVES POSSESSING CALCIUM UPTAKE INHIBITING ACTIVITY

[75] Inventors: Masami Muraoka; Kazuki Matsui; Hirohiko Hasegawa, all of Osaka; Atsuyuki Kojima, Hyogo, all of Japan

[73] Assignee: Sumitomo Pharmaceuticals Co., Ltd., Osaka, Japan

[21] Appl. No.: 249,212

[22] Filed: May 26, 1994

[30] Foreign Application Priority Data

May 26, 1993 [JP] Japan .................................. 5-148495

[51] Int. Cl.$^6$ ...................... C07D 239/82; C07D 239/84; A61K 31/505; A61K 31/435
[52] U.S. Cl. ................. 514/258; 514/259; 544/278; 544/279; 544/284; 544/286
[58] Field of Search ................................. 514/258, 259; 544/278, 279, 284, 286

[56] References Cited

U.S. PATENT DOCUMENTS

| | | | |
|---|---|---|---|
| 3,547,921 | 12/1970 | Hardtmann et al. | 260/251 |
| 3,686,178 | 8/1972 | Cooke et al. | 260/251 |
| 3,812,257 | 5/1974 | Yamamoto et al. | 424/251 |
| 3,819,627 | 6/1974 | Ott | 260/251 |
| 3,829,420 | 8/1974 | Inaba et al. | 544/286 |
| 4,009,166 | 2/1977 | Noda et al. | 260/256.4 |
| 4,099,002 | 7/1978 | Inaba et al. | 544/119 |
| 4,179,560 | 12/1979 | Yamamoto et al. | 544/250 |
| 4,335,127 | 6/1982 | Vandenberk et al. | 424/251 |
| 4,522,945 | 6/1985 | Vandenberk et al. | 514/259 |

FOREIGN PATENT DOCUMENTS

| | | |
|---|---|---|
| 0029707 | 6/1981 | European Pat. Off. . |
| 2012062 | 3/1970 | France . |
| 2027023 | 9/1970 | France . |
| 9304047 | 3/1993 | WIPO . |

OTHER PUBLICATIONS

G. E. Hardtmann et al., "Synthesis and Antiinflammatory Activity of Some . . . pyrimidin-2(1H)-ones", *Journal of Medicinal Chemistry*, vol. 17, No. 6, 1974, pp. 636–639.
G. Zigeuner et al., "Über Dihydro-6-methyl-. . . cinnamoyl-4,7-diphenyl-2(1H)-chinazolinone (-thione)", *Monatshefte für Chemie*, 101, 1970, pp. 1767–1787.
Masato Tani, "Mechanisms of Ca$^{2+}$ Overload In Reperfused Ischemic Myocardium", Annu. Rev. Physiol., 1990, 52:543–59.
Gordon L. Todd et al., "Protective effects of slow channel calcium antagonists on noradrenaline induced myocardial necrosis", Cardiovasc. Res., 1986, 20, 645–651.
Stephen V. Frye et al. "Synthesis of 2-Aminobenzophenones via Rapid Halogen–Lithium Exchange in the Presence of a 2-Amino-N-methoxy-N-methylbenzamide", J. Org. Chem., 1991, 56, 3750–3752.
L. Estel et al., "Synthesis of ortho–Substituted Aminopyridines. Metalation of Pivaloylamino Derivatives" J. Heterocyclic Chem., 1989, 26, 105.

M. Yamamoto et al., "Synthetic Studies on Quinazoline Derivatives I. Formation of 2(1H)–Quinazolinones from the Reaction of 2–Trihaloacetamidophenyl Ketones with Ammonia", Chem. Pharm. Bull., 1978, 26(6)1633–1651.
Francis J. Tinney et al., "Synthesis and Pharmacological Evaluation of 2,3–Dihydro–1H–thieno[2,3–e][1,4]diazepines", J. Med. Chem., 1974, vol. 17, No. 6, 624–630.
Miyuki Ishizaki et al., J. Org. Chem., 1992, 57, 7285–7295.
Osamu Hoshino et al., "A stereoselective Synthesis of a Basic Skeleton of Amaryllidaceae Montanine–type Alkaloids, (±)–4a,11a–cis–11,11a–syn–5,11–Methanomorphanthridine Ring System", Chem. Lett. 1990, 1817–1820.
Ramesh Vemuri et al., "Quabain treatment of cardiac cells induces enhanced Na$^+$–Ca$^+$ exchange activity" Am. J. Physiol., 1989, 256, C1273–C1276.
J. C. Khatter et al., "Digitalis cardiotoxicity:cellular calcium overload a possible mechanism", Basic Res. Cardiol., 1989, 84:553–563, P116L20.
Donghee Kim et al., "Inhibition of Multiple Trans-sarcolemmal Cation Flux Pathways by Dichlorobenzamil Cultured Chick Heart Cells", Mol. Pharmacol., 1986, 30:164–170, P120L21–22.
Roy C. Ziegelstein et al., Circ. Res., 1992, 70:804–811, P120L22.
Tomoe Y. Nakamura et al., Circ. Res. 1993, 73:758–770, P120L27.
Database WPI, Week 8229, Derwent Publications Ltd., corresponding to JP–A–57–095966, Jun. 15, 1982.

(List continued on next page.)

*Primary Examiner*—Mukund J. Shah
*Assistant Examiner*—Matthew V. Grumbling
*Attorney, Agent, or Firm*—Sughrue, Mion, Zinn, Macpeak & Seas

[57] ABSTRACT

This invention is to provide quinazolinone derivatives, and their acid salts and quaternary ammonium salts, having an effect of preventing or treating diseases caused by calcium ion overload in cells, such as ischemic heart disease, ischemic cerebral disease and ischemic renal disease, and their usage. The quinazolinone derivatives are represented by the formula:

typically, T represents an oxygen atom; Y represents a phenyl or cyclohexyl group; $R^1$ represents a hydrogen or chlorine atom; $R^2$ represents a hydrogen atom; ring W represents a benzene or pyridine ring; Z represents a group of the formula:

8 Claims, 2 Drawing Sheets

OTHER PUBLICATIONS

Database WPI, Week 8142, Derwent Publications Ltd., corresponding to JP–A–56–113769, Sep. 7, 1981.

F. Ishikawa and H. Yamaguchi, "Cyclic Guanidines. XIII. Synthesis of . . . pyrimidine Derivatives", *Chem. Pharm. Bull.*, vol. 28, No. 11, 1980, pp. 3172–3177.

M. Yamamoto and H. Yamamoto, "Synthetic Studies on Quinazoline Derives . . . Primary Amines", *Chem. Pharm. Bull.*, vol. 29, No. 8, 1981, pp. 2135–2156.

Yamamoto et al., "Synthetic Studies on Quinazoline Derivatives. II. The Reactions of 2–Trichlor and 2–Trifluoracetamidobenzophenones with Primary Amines," Chemical and Pharmaceutical Bulletin, 1981, vol. 29, No. 8, 2135–2156.

QUINAZOLINONE DERIVATIVES POSSESSING CALCIUM UPTAKE INHIBITING ACTIVITY

BACKGROUND OF THE INVENTION

1. Field of the Invention

The present invention relates to quinazolinone derivatives, their acid-addition salt or their quaternary ammonium salt, having an effect of preventing overload of calcium ions ($Ca^{2+}$) in cells, as well as their usages.

2. Description of the Prior Art

Overload of calcium ions ($Ca^{2+}$) in cells has been regarded as an important matter in the cell injury mechanism after ischemia or reperfusion. See, for example, Annu. Rev. Physiol., 1990, 52, 543–559. Cell injuries caused by ischemia or reperfusion are observed in many diseases routinely encountered, and those in heart, brain and kidney, among others, are serious problems experienced clinically. Thus, an agent preventing overload of calcium ions could be a useful preventing or treating agent for ischemic heart disease, ischemic cerebral disease and ischemic renal disease.

Heretofore, a calcium antagonist has been used as an agent for preventing the influx of calcium ions into myocardial cells or blood vessel smooth muscle cells. However, its effect on the overload of calcium ions in myocardial cells after ischemia or reperfusion is not satisfactory. Thus, an agent for preventing the calcium overload has been keenly desired.

Calcium ion overload induces injuries in myocardial cells or smooth muscle cells, such as disorders, not only in case of ischemia, but in the contraction and relaxation function and in the energy metabolism, as well as morphological damages and electro-physiological disorder, thus causing diseases in the circulatory organs. See, for example, Cardionvasc. Res., 1986, 20, 645–651. Accordingly, an agent for preventing calcium ion overload could be a useful preventing or treating agent for circulatory diseases, such as heart failure, hypertension and arrhythmia.

SUMMARY OF THE INVENTION

An object of the invention is to provide for a group of compounds which prevents overload of calcium ions in cells. Other objects will be apparent from the following descriptions.

After extensive studies to solve the problems encountered in the past, the present inventors have found that compounds represented by the following formula (1) prevent the occurrence of calcium ion overload in cells, and accomplished the present invention based on such findings.

Thus, the invention relates to a calcium ion overload preventing agent containing a pharmaceutically effective amount of a quinazolinone derivative represented by the formula (1):

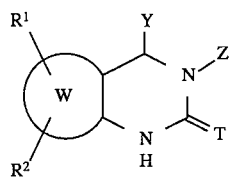
(1)

wherein T represents an oxygen or sulfur atom; Y represents an alkyl, cycloalkyl, cycloalkylalkyl, phenyl, substituted phenyl, aralkyl, substituted aralkyl, heteroaryl or substituted heteroaryl group; ring W represents a benzene, 5–6 membered heteroaromatic, or 5–10 membered cycloalkene or cycloalkane ring; $R^1$ and $R^2$ represent, independently, a hydrogen or halogen atom, or a lower alkyl, cyano, trifluoromethyl, nitro, amino, substituted amino, hydroxy, lower alkoxyl, lower alkylthio, lower alkylsulfinyl or lower alkylsulfonyl group; Z represents the following group (1a) or (1b):

(1a)

in which $A^1$ and $A^2$ represent, independently, a hydrogen atom, or an alkyl, substituted alkyl, cycloalkyl, saturated heterocyclic, cycloalkylalkyl, cycloalkenylalkyl, aralkyl, substituted aralkyl, heteroarylalkyl, substituted heteroarylalkyl or —$CH_2R^3$ group, $R^2$ being an alkenyl or alkynyl group, or $A^1$ and $A^2$ may be bound each other to form a hetero ring; and G represents a straight chain alkylene group having 1 to 6 carbon atoms, a branched alkylene group having 1 to 8 carbon atoms, or the following group:

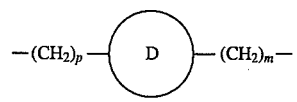

wherein p and m stand, independently, 0 or an integer of 1 and 2; and D is a cycloalkane ring; or

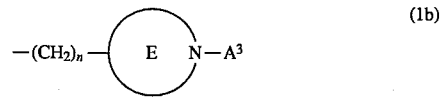
(1b)

in which n stands 0 or an integer of 1 and 2; ring E represents a 4–8 membered saturated heterocyclic ring containing a nitrogen atom; and $A^3$ represents a hydrogen atom, or an alkyl, substituted alkyl, cycloalkyl, saturated heterocyclic, cycloalkylalkyl, cycloalkenylalkyl, aralkyl, substituted aralkyl, heteroarylalkyl, substituted heteroarylalkyl or —$CH_2R^3$ group, $R^3$ being an alkenyl or alkynyl group, or may be bound to the ring E to form a bicyclo ring; or a pharmaceutically acceptable acid-addition salt or quaternary ammonium salt thereof.

Furthermore, the invention relates to a quinazolinone derivative of the formula (1) in which the ring W is a 5–6 membered heteroaromatic or 5–10 membered cycloalkene or cycloalkane ring, and to a pharmaceutically acceptable acid salt or quaternary ammonium salt thereof, and to a quinazolinone derivative of the formula (1) in which the ring W is a benzene ring and Z is the following group:

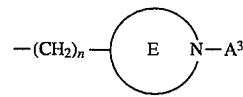

in the formula, n, ring E and $A^3$ having the same meanings as mentioned above, or a pharmaceutically acceptable acid-addition salt or quaternary ammonium salt thereof.

Among the compounds which may be employable in the present invention, some compounds in which the ring W is a benzene ring and Z is a group of the following formula:

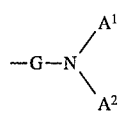

wherein G, $A^1$ and $A^2$ have the same meanings as above, have been already known as central nervous system depressants, anti-inflammatory drugs and sedatives in the Japanese Patent Laid-Open publication No. 14183/1972, as central nervous system depressants in the French Patent No. 2,027,023. Some compounds employable in the invention have been disclosed as inhibitors for HIV reverse transcriptase in WO 93/04047. However, the compounds claimed in the present invention are not shown in the examples mentioned in such patent. Compounds which are analogous to some of those employable in the present invention have been described as antipyretic compounds in the French Patent No. 2,012,062, as hypotensive, anti-ulcer, anti-platelet coagulating compounds in the Japanese Patent Laid-Open Publication No. 92,884/1981, as sedative, anti-inflammatory and central nervous system depressant compounds in the Japanese Patent Laid-Open Publication No. 13,794/1976, and as anti-inflammatory compounds in the J. Med. Chem., 1974, 17, 636–639.

Groups in the compounds of the present invention will be mentioned in detail below.

Specifically, the 5–6 membered heteroaromatic ring in the ring W includes that having 0, 1 or 2 of nitrogen atoms, that having 0 or 1 of sulfur atom and that having 0 or 1 of oxygen atom. More specifically, the rings as mentioned below:

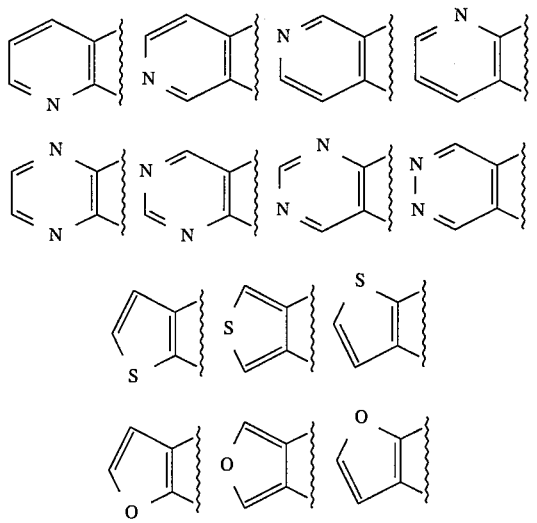

preferably the rings as mentioned below.

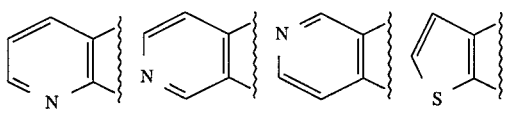

may be illustrated.

The 5–10 membered cycloalkene or cycloalkane ring in the ring W includes specifically the following rings:

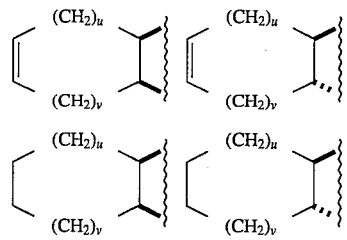

in which u and v mean, independently, 0 or an integer of 1 to 5, u+v being an integer of 1 to 6, and the thick lines and dotted lines in the formulas represent the relative steric configurations of the carbon atoms each adjacent at the bridgeheads, but do not mean sole specific optical isomers, the same being applied in the following formulas, and, preferably, the following rings;

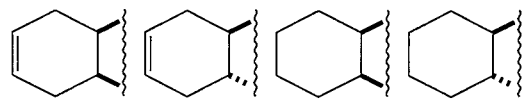

may be illustrated.

In G, the straight chain alkylene group having 1 to 6 carbon atoms includes methylene, dimethylene, trimethylene and tetramethylene, and the branched alkylene group having 1 to 8 carbon atom includes the following groups:

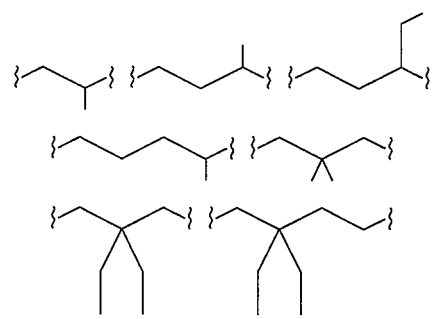

In D, the cycloalkane ring may be that having 3 to 8 carbon atoms. Specifically, it includes, for example, cyclopropane, cyclobutane, cyclopentane, cyclohexane, cycloheptane and cyclooctane.

As preferable groups in G, there may be illustrated dimethylene, trimethylene, tetramethylene, and the following groups:

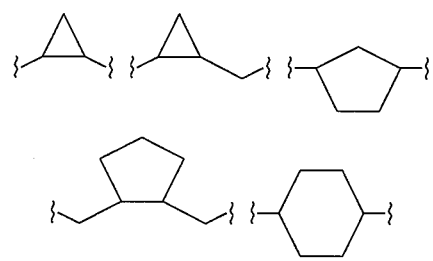

The alkyl group may be straight chain or branched alkyl group having 1 to 8 carbon atoms. Specifically, it includes, for example, methyl, ethyl, propyl, 2-propyl, butyl, 2-butyl, 2-methylpropyl, 1,1-dimethylethyl, 3-pentyl, 3-hexyl, 4-heptyl, 4-octyl and the like. As preferable groups, 2-propyl, butyl, 2-butyl, 2-methylpropyl, 3-pentyl and 3-hexyl, in Y, and alkyl group having 1 to 4 carbon atoms such as methyl, ethyl, propyl and 2-propyl, in $A^1$, $A^2$ and $A^3$, are illustrated.

The cycloalkyl group may be that having 3 to 7 carbon atoms. Specifically, it includes, for example, cyclopropyl, cyclobutyl, cyclopentyl, cyclohexyl, cycloheptyl and the like.

The cycloalkylalkyl group may be that having not more than 10 carbon atoms. Specifically, it includes, for example, cyclopropylmethyl, 2-cyclopentylethyl, cyclohexylmethyl, 3-cyclohexylpropyl, 4-cyclohexylbutyl and the like.

The cycloalkenylalkyl group may be that having not more than 10 carbon atoms. Specifically, it includes, for example, 4-cyclohexenylmethyl, 4-cyclopentenylmethyl, 4-(4-cyclohexenyl)butyl and the like.

The alkenyl group may be that having 2 to 6 carbon atoms. Specifically, it includes, for example, vinyl, allyl, 1-propenyl, 1-butenyl, 2-pentenyl, 5-hexenyl and the like, among which vinyl and allyl are preferred.

The alkynyl group may be that having 2 to 6 carbon atoms. Specifically, it includes, for example, ethynyl, propargyl, 2-butynyl, 3-pentynyl and the like, among which ethynyl and propargyl are preferred.

The aralkyl group may be that having not more than 12 carbon atoms. Specifically, it includes benzyl, 1-phenylethyl, 2-phenylethyl, 2-naphthylmethyl and the like. The preferable aralkyl group in $A^3$ is benzyl.

The heteroaryl group may be that having 5 to 6 membered ring with 1 to 2 nitrogen atoms, that having 5 to 6 membered ring with 1 to 2 nitrogen atoms and one oxygen or sulfur atom, and that having 5 to 6 membered ring with one oxygen or sulfur atom. Specifically, they include, for example, 2-pyridyl, 3-pyridyl, 4-pyridyl, 2-thienyl, 3-oxadiazolyl, 2-imidazolyl, 2-thiazolyl, 3-isothiazolyl, 2-oxazolyl, 3-isoxazolyl, 2-furyl, 3-pyrrolyl and the like.

The heteroarylalkyl group may be that having a heteroaryl group of 5 or 6 membered ring with 1 to 4 nitrogen atoms or with 1 or 2 nitrogen atoms and one oxygen or sulfur atom. Specifically, it includes, for example, 2-pyridylmethyl, 3-pyridylmethyl, 4-pyridylmethyl, 1-(2-pyridyl)ethyl, 2-(2-pyridyl)ethyl, 2-thienylmethyl, 3-thienylmethyl, 3-oxadiazolylmethyl, 2-imidazolylmethyl, 2-thiazolylmethyl, 3-isothiazolylmethyl, 2-oxazolylmethyl, 3-isoxazolymethyl, 2-furylmethyl, 3-furylmethyl, 2-pyrrolylmethyl and the like.

The saturated heterocyclic group may be that composed of one hetero atom, such as oxygen and sulfur, and 3 to 5 carbon atoms. Specifically, it includes, for example, tetrahydropyran-4-yl, tetrahydrofuran-3-yl, tetrahydrothiophen-3-yl and the like.

The hetero ring formed when $A^1$ and $A^2$ are bound each other may be that having 5 to 7 membered ring with 1 or 2 nitrogen atoms or with one nitrogen atom and one oxygen atom. Specifically, it includes, for example, pyrrolidine, piperidine, homopiperidine, piperazine, homopiperazine, morpholine and the like.

The 4 to 8 membered saturated heterocyclic ring with nitrogen atom in ring E may be that having 1 or 2 nitrogen atoms and 0 or 1 oxygen atom. Specifically, it includes, for example, pyrrolidin-2-yl, pyrrolidin-3-yl, piperidin-2-yl, piperidin-3-yl, piperidin-4-yl, homopiperidin-2-yl, homopiperidin-3-yl, homopiperidin-4-yl, morpholin-2-yl and the like. Preferred are piperidin-4-yl in case of n being 0, and pyrrolidin-2-yl, pyrrolidin-3-yl, piperidin-2-yl, piperidin-3-yl and morpholin-2-yl in case of n being 1 or 2.

The bicyclo ring formed from ring E and $A^3$ includes, for example, quinuclidin-3-yl, quinuclidin-4-yl and the like.

The lower alkyl group may be a straight chain or branched alkyl group having not more than 4 carbon atoms. Specifically, it includes methyl, ethyl, propyl, 2-propyl, butyl, 2-butyl, 2-methylpropyl, 1,1-dimethylethyl and the like.

The halogen atom may be fluorine, chlorine, bromine and iodine.

The lower alkoxyl group may be a straight chain or branched alkoxyl group having not more than 4 carbon atoms. Specifically, it includes, for example, methoxy, ethoxy, propoxy, 2-propoxy, butoxy, 1,1-dimethylethoxy and the like.

The lower alkylthio group may be a straight chain or branched alkylthio group having not more than 4 carbon atoms. Specifically, it includes, for example, methylthio, ethylthio, 2-propylthio, butylthio and the like.

The lower alkylsulfinyl group may be a straight chain or branched alkylsulfinyl group having not more than 4 carbon atoms. Specifically, it includes, for example, methylsulfinyl, ethylsulfinyl, propylsulfinyl, 2-propylsulfinyl, butylsulfinyl and the like.

The lower alkylsulfonyl group may be a straight chain or branched alkylsulfonyl group having not more than 4 carbon atoms. Specifically, it includes, for example, methylsulfonyl, ethylsulfonyl, propylsulfonyl, 2-propylsulfonyl, butylsulfonyl and the like.

The substituent in the substituted amino group may be an alkyl or —$CH_2R^6$ group wherein $R^6$ is alkenyl or alkynyl. The substituent may be either single or two of the same or different kinds. Preferable substituted amino group includes, for example, methylamino, ethylamino, allylamino, propargylamino, propylamino, 2-propylamino, butylamino, N,N-dimethylamino, N,N-diethylamino, N,N-dipropylamino, N,N-diallylamino and the like.

The substituents in the substituted phenyl, substituted aralkyl, substituted heteroaryl and substituted heteroarylalkyl groups include, for example, halogen atoms and lower alkyl, lower alkoxy, methylenedioxy, cyano, trifluoromethyl, nitro, hydroxy, lower alkanoyloxy, amino, lower alkylamino, di-lower alkylamino, carbamoyl, lower alkylaminocarbonyl, di-lower alkylaminocarbonyl, carboxyl, lower alkoxycarbonyl, lower alkylthio, lower alkylsulfinyl, lower alkylsulfonyl, lower alkanoylamino, lower alkylsulfonamido groups and the like. The term, "lower", referred to herein means that the alkyl portion in the groups is a lower alkyl, including that having 1 to 4 carbon atoms, such as methyl, ethyl, propyl, 2-propyl, butyl and the like. Also, two lower alkyl groups in the di-lower alkylamino and di-lower alkylaminocarbonyl groups may be the same or different. The substituent may be either single or plural of the same or different kinds.

The substituent in the substituted alkyl group includes hydroxy, lower alkoxy, cyano, carboxy, carbamoyl, lower alkoxycarbonyl and the like groups. The term, "lower", referred to herein means that the alkyl portion in the groups is a lower alkyl, including that having 1 to 4 carbon atoms, such as methyl, ethyl, propyl, 2-propyl, butyl and the like.

The acids forming the acid addition salt include, for example, inorganic acids, such as hydrogen chloride, hydrogen bromide, hydrogen iodide and sulfuric acid, and organic acids such as acetic acid, oxalic acid, citric acid, malic acid, tartaric acid, fumaric acid, maleic acid and methanesulfonic acid.

The quaternary ammonium salt may be that prepared by a reaction with an alkylating agent represented by the formula, $R^4$—$L^1$, in which $R^4$ means a lower alkyl group and $L^1$ means a leaving group, if necessary, followed by exchanging the anion with another physiologically acceptable anion. The preferable lower alkyl group includes methyl and ethyl. The physiologically acceptable anion includes halogen ion, sulfate, phosphate, nitrate, acetate, citrate, fumarate, succinate and the like. The preferable leaving group includes chlorine, bromine and iodine atoms.

The compounds of the invention retain one or more asymmetric carbon atoms, thus, there being the stereoisomers. Accordingly, the compounds of the invention comprise those isomers in the form of mixtures and as isolated ones.

When the compounds represented by the formula (1) or their acid salt or quaternary ammonium salt are used as treating or preventing agents for diseases, such as ischemic heart disease, ischemic cerebral disease and ischemic renal disease, they may be administered parenterally or orally. They may be administered as an injection in the form of a solution, emulsion, suspension, If required, a buffer, solubilizing agent or etc. isotonic agent may be added thereto. They may be administered via rectum as suppositories. The administering formulations may be prepared according to any of the conventional methods, for example, by blending the active ingredient with a carrier, excipient, binder, stabilizer etc. They may also be administered orally, in any administering formulation, for example, as tablets, capsules, syrup, suspension, etc. Amount and frequency for administration vary depending upon the symptom, age, body weight and type of formulation. In case of injecting administration, they may be administered, in general, in an amount of 0.1 to 100 mg at once or in several times for adult. They may also be administered by drip infusion. In case of oral administration, an amount of 1 to 1,000 mg/day, preferably 1 to 100 mg/day, may be administered once or in several times a day.

The compounds of the invention in which the ring W in the formula (1) is a benzene ring or a 5 or 6 membered heteroaromatic ring can be synthesized according to any method described in the literatures for example, Chem. Pharm. Bull., 1981, 29, 2135–2156, as follows:

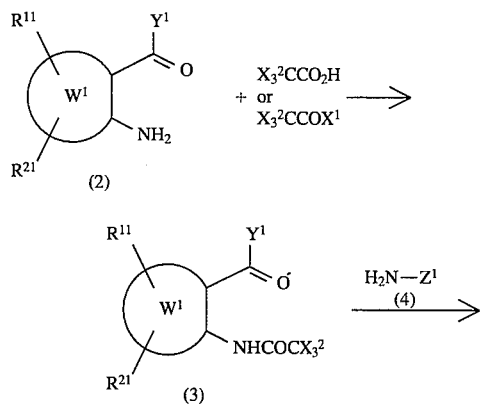

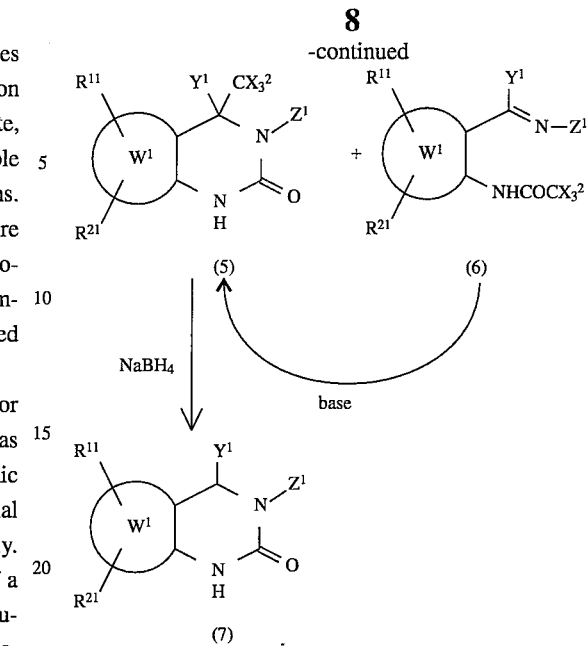

wherein, the ring $W^1$ represents a benzene or 5 or 6 membered heteroaromatic ring; $X^1$ represents a chlorine, bromine or iodine atom; $X^2$ represents a fluorine, chlorine or bromine atom; $Y^1$ represents the same group as in Y, but, when the group contains a reactive group such as amino, alkylamino and hydroxy group, as the substituent, such a reactive group should have been protected by conventional protective group; $R^{11}$ represents the same group as in $R^1$, but, when the group is a reactive group such as amino, alkylamino and hydroxy group, such a group should have been protected by conventional protective group; $R^{21}$ represents the same group as in $R^2$, but, when the group is a reactive group such as amino, alkylamino and hydroxy group, such a group should have been protected by conventional protective group; and $Z^1$ represents the same group as in Z, in which a case of both $A^1$ and $A^2$ being hydrogen is excluded, and, when $A^1$, $A^2$ or $A^3$ contains a reactive group such as amino, alkylamino and hydroxy group as the substituent, such a reactive group should have been protected by conventional protective group.

The starting material represented by the formula (2) are commercially available, or can be synthesized according to any of the methods described in the literatures, for example, J. Org. Chem., 1991, 56, 3750–3752; J. Heterocyclic Chem., 1989, 26, 105; Chem. Pharm. Bull., 1978, 26, 1633–1651; and J. Med. Chem., 1974, 17, 624–630. The protective group for amino, alkylamino or hydroxy group may be an ordinary one employed in the field of organic synthetic chemistry, for example, a benzyl or acetyl group for the protection of hydroxy group, and a benzyl group for the protection of amino group. Such a protective group may be introduced or removed according to any conventional method, for example, that described in "Protective Groups in Organic Synthesis", 2nd Ed., John Wily & Sons, Inc.: New York.

The ketone derivatives represented by the formula (2) may be converted to the amide derivatives represented by the formula (3) according to any known method, for example, by an acylation with a trihaloacetic acid or its acid chloride.

The quinazolinone derivative of the formula (5), its imine derivative of the formula (6) or a mixture of the both derivatives can be obtained by the reaction of the ketone derivative of the formula (3) with a primary amine of the formula (4) in an aprotic polar solvent, such as dimethylformamide, dimethylsulfoxide and tetrahydrofuran, at temperature of 0° C. to 50° C. The amount ratio of the quinazolinone derivative of the formula (5) and the imine derivative of the formula (6) formed varies depending on the structure of the ketone derivative of the formula (3) and the primary amine of the formula (4), and the reaction conditions. The imine derivative of the formula (6) can be converted to the quinazolinone derivative of the formula (5) by heating in a solvent as mentioned above at temperature of about 50° C. to 100° C., or up to the boiling point of the solvent, in the presence of a base. As the base, tertiary amines and aromatic amines, such as triethylamine or pyridine are suitable.

The quinazolinone derivative of the formula (5) is treated with sodium borohydride ($NaBH_4$) in an aprotic polar solvent such as dimethylformamide or tetrahydrofuran at a temperature of about 0° C. to ambient temperature to give the quinazolinone derivative of the formula (7) in which the trihalomethyl group has been substituted to a hydrogen atom. In this course of reaction, borane ($BH_3$) might be coordinated to the nitrogen atom in the group $Z^1$. In such a case, the borane can be eliminated normally by heat under reflux in an alcoholic solvent such as ethanol or methanol, if necessary, in the presence of an aqueous hydrochloric acid. If no borane is coordinated, such a process is not necessary.

The imine derivative of the formula (6) can be derived to the quinazolinone derivative of the formula (7) via the following route:

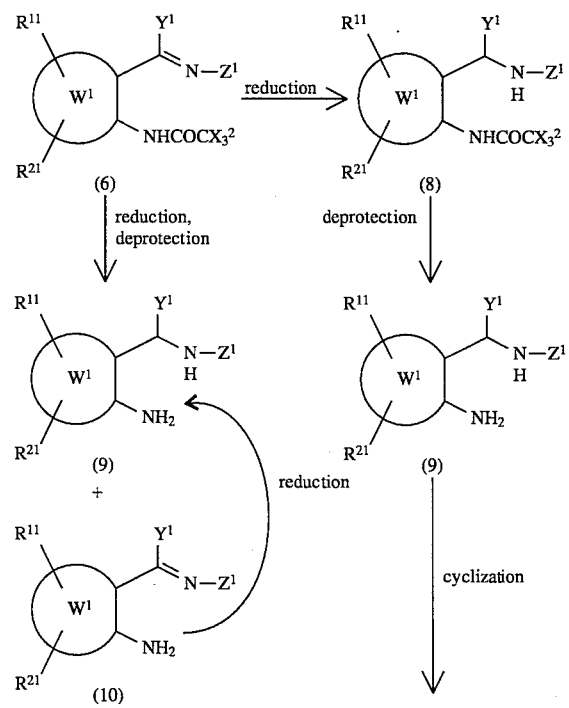

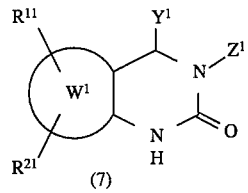

wherein ring $W^1$, $Z^1$, $R^{11}$, $R^{21}$, $Y^1$ and $X^2$ have the same meanings as above.

The imine derivative of the formula (6) can be derived to the amine derivative of the formula (8) by reduction with sodium borohydride in an aprotic polar solvent, such as dimethylformamide, dimethylsulfoxide or tetrahydrofuran, at temperature of about 0° C. to 50° C. Then, the diamine derivative of the formula (9) can be obtained by removing the trihaloacetyl group therefrom. The removal of the trihaloacetyl group (namely, deprotection) can suitably be conducted by treating with sodium borohydride in a lower alcohol, such as methanol or ethanol, at temperature of about 0° C. to 50° C. Also, the diamine derivative of the formula (9) can be obtained from the imine derivative of the formula (6) in one step, by treating with sodium borohydride in a lower alcohol, such as methanol or ethanol, at temperature of about 0° C. to 50° C. In this reaction, the imine derivative of the formula (10) might also be formed, which can be converted to the diamine derivative of the formula (9) by the reduction with lithium aluminum hydride ($LiAlH_4$) in an ethereal solvent, such as diethyl ether or tetrahydrofuran, at temperature between ambient temperature and the boiling point of the solvent.

The quinazolinone derivative of the formula (7) can be synthesized by the reaction of the diamine derivative of the formula (9) with 1.0 to 5 times equivalent of 1,1'-carbonyldiimidazole in a solvent, halogenated hydrocarbon such as methylene chloride, chloroform or diethyl ether, tetrahydrofuran, dioxane, acetonitrile, dimethylformamide or dimethylsulfoxide, at a temperature between ambient temperature and the boiling point of the solvent. Also, the quinazolinone derivative of the formula (7) can be synthesized by the reaction of the diamine derivative of the formula (9) with a carboxylic acid chloride, for example, phosgene or alkyl chlorocarbonates, according to the well known procedure.

The quinazolinone derivative of the formula (11) can be obtained from the quinazolinone derivative of the formula (7), as required, according to the following procedures:

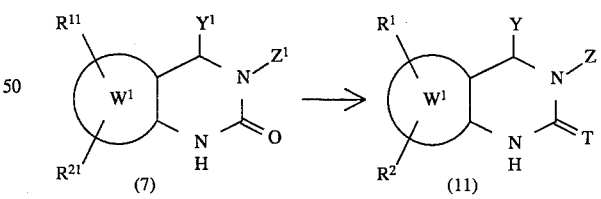

wherein ring $W^1$, Z, $R^1$, $R^2$, Y and T have the same meanings as above.

(a) To obtain the compound in which T in the formula (11) is a sulfur atom, a conversion of urea to thiourea.
(b) A conversion of $Z^1$.
(c) Deprotection of the protective group, when $R^{11}$ or $R^{21}$ in the formula (7) has been protected, or when $Y^1$ or $Z^1$ contains a protective group.
(d) A conversion of the substituent in $R^1$, $R^2$ or $Y^1$, or in $Z^1$.

The conversion of urea to thiourea can be performed by the reaction with phosphorus pentasulfide in an inert solvent, such as carbon disulfide, toluene or xylene, at a temperature between ambient temperature and the boiling point of the solvent.

When, for example, the compound (7) is the quinazolinone derivative of the formula (12), the conversion of $Z^1$ can be performed by subjecting to a de-benzylating reaction according to any well known method, and then subjecting to a reductive amination or alkylation to give the quinazolinone derivative represented by the formula (15) or (17).

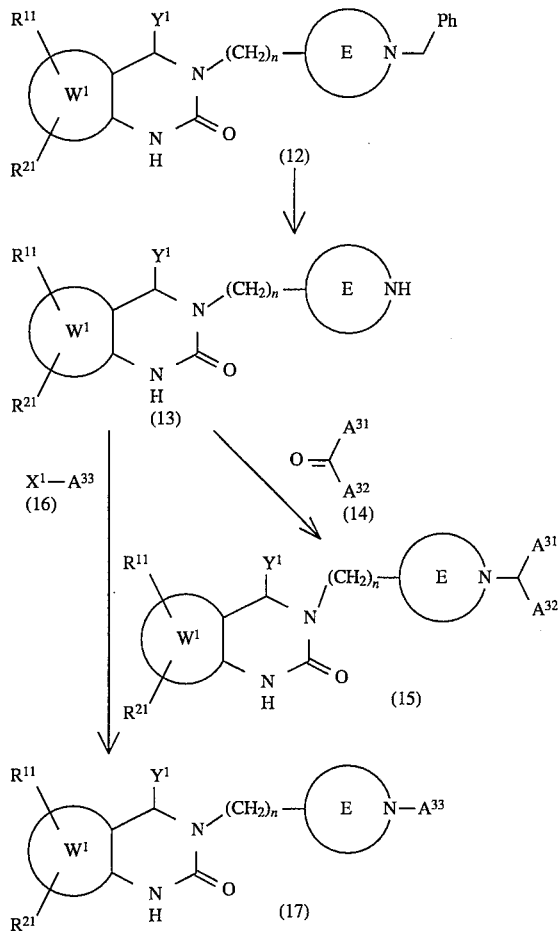

wherein ring $W^1$, ring E, $R^{11}$, $R^{21}$, $Y^1$, $X^1$ and n have the same meaning as above; $A^{3\,1}$ represents a hydrogen atom or a methyl or ethyl group; $A^{3\,2}$ represents an alkyl, substituted alkyl, cycloalkyl, cycloalkenyl, aryl, substituted aryl, heteroaryl, substituted heteroaryl or —$CH_2R^3$ group, wherein $R^3$ is an alkenyl or alkynyl group, or, $A^{3\,1}$ and $A^{3\,2}$ may be bound each other to form a cyclopentane, cyclohexane or cycloheptane ring; and $A^{3\,3}$ represents an alkyl, substituted alkyl, cycloalkyl, saturated heterocyclic, cycloalkylalkyl, cycloalkenylalkyl, aralkyl, substituted aralkyl, heteroarylalkyl, substituted heteroarylalkyl, or —$CH_2R^3$ group, wherein $R^3$ is an alkenyl or alkynyl group.

The reductive aminating reaction can be per formed by treating the compound of the formula (13) and 1 to 5 equivalents of the carbonyl compound of the formula (14) with 1 to 5 equivalents of a reducing agent in a lower alcohol, such as methanol or ethanol, at temperature of 0° C. to 50° C. As the reducing agent, sodium borohydride ($NaBH_4$) or sodium cyanoborohydride ($NaBH_3CN$) are suitably used.

The alkylating reaction can be performed according to any well known procedure. For example, the compound of the formula (13) is treated with 1 to 5 equivalents of the halide compound of the formula (16) in a solvent, such as tetrahydrofuran, dimethylformamide, dichloromethane, methanol or ethanol, if required, in the presence of a base such as potassium carbonate or triethylamine, at temperature between 0° C. and the boiling point of the solvent.

When the compound of the formula (11) is the quinazolinone of the formula (18), the reductive amination or alkylation can be performed in similar way. The quinazolinone derivative of the formula (18) can be synthesized from the quinazolinone derivative of the formula (20) which own is included in the formula (18), according to the method mentioned above. The quinazolinone derivative of the formula (20) can be obtained preferably by the de-benzylating reaction of the quinazolinone derivative of the formula (19), according to any well known procedure.

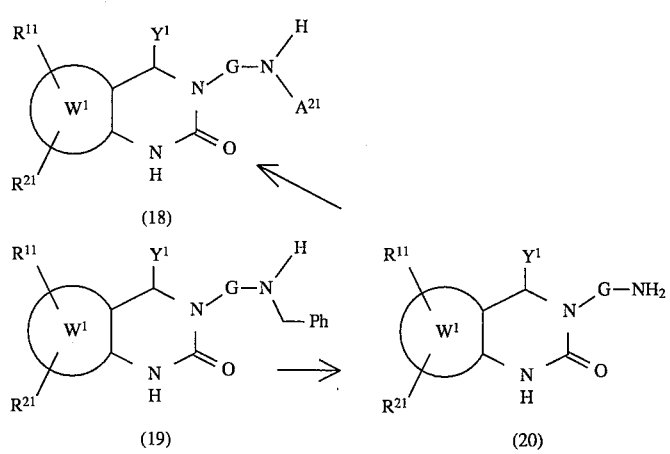

wherein ring $W^1$, $R^{11}$, $R^{21}$, Y and G have the same meanings as above; and $A^{21}$ has the same meanings as in $A^2$, but, when the group contains a reactive group, such as amino, alkylamino or hydroxyl group, as the substituent, such a reactive group should have been protected by a protective group.

When the groups in $R^{11}$ or $R^{12}$ have been protected, or $Y^1$ or $Z^1$ contains a protected group, in the formula (7), the removal of the protective group can be performed according to any conventional procedure for deprotection employed in the field of organic synthetic chemistry, for example, as described in "Protective Groups in Organic Synthesis", 2nd Ed., John Wily & sons, Inc.: New York.

As for the conversion of the substituents in $R^1$, $R^2$ or $Y^1$, or in $Z^1$, for example, the lower alkylthio group can be converted to a lower alkylsulfinyl or lower alkylsulfonyl group by oxidation; the nitro group can be converted to an amino group by reduction: the amino group can be converted to the mono- or dialkylamino group by alkylation; or the amino group can be acylated. Such conversions of substituents can be performed according to the general procedures ordinarily employed in the field of organic synthetic chemistry.

The compound (22), which is the quinazolinone derivative of the formula (11) having a sulfur atom as T, may be synthesized by the diamine derivative of the formula (9) according to the following steps:

The quinazolinone derivative of the formula (21) can be synthesized by the reaction of a diamine derivative of the formula (9) with 1.0 to 5 times equivalents of 1,1'-thiocarbonyldiimidazole in an solvent, such as methylene chloride, chloroform or other halogenated hydrocarbons, diethyl ether, tetrahydrofuran, dioxane, acetonitrile, dimethylformamide or dimethylsulfoxide, at a temperature between ambient temperature and the boiling point of the solvent. Then, the product can be derived, if necessary, to the quinazolinone derivative of the formula (22) through the conversion or deprotection of the substituent in similar way as in the compound (7).

The compounds in which the ring W in the formula (1) is a 5 to 10 membered cycloalkene or cycloalkane ring can be synthesized according to the following steps:

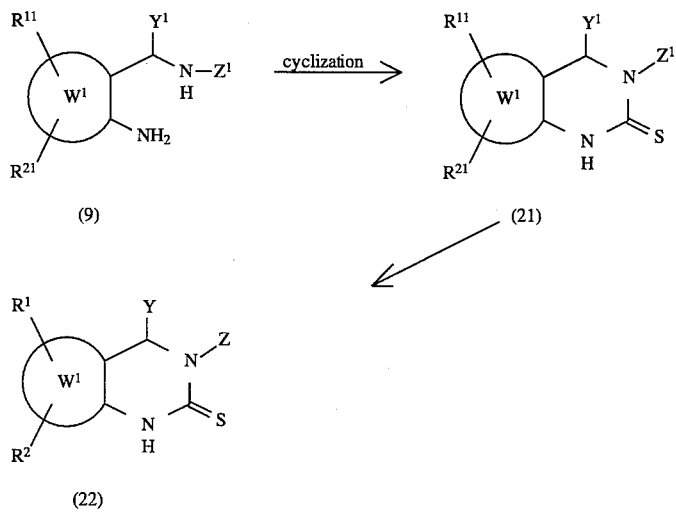

wherein ring $W^1$, $R^{11}$, $R^{21}$, $Y^1$, $Z^1$, $R^1$, $R^2$, Z and Y have the same meanings as above.

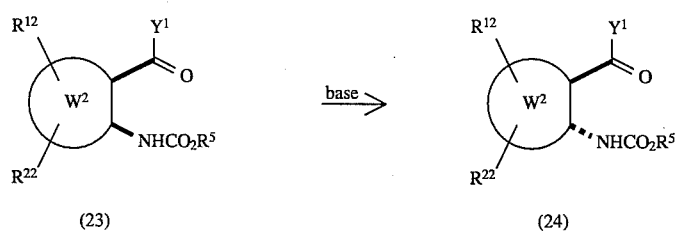

-continued

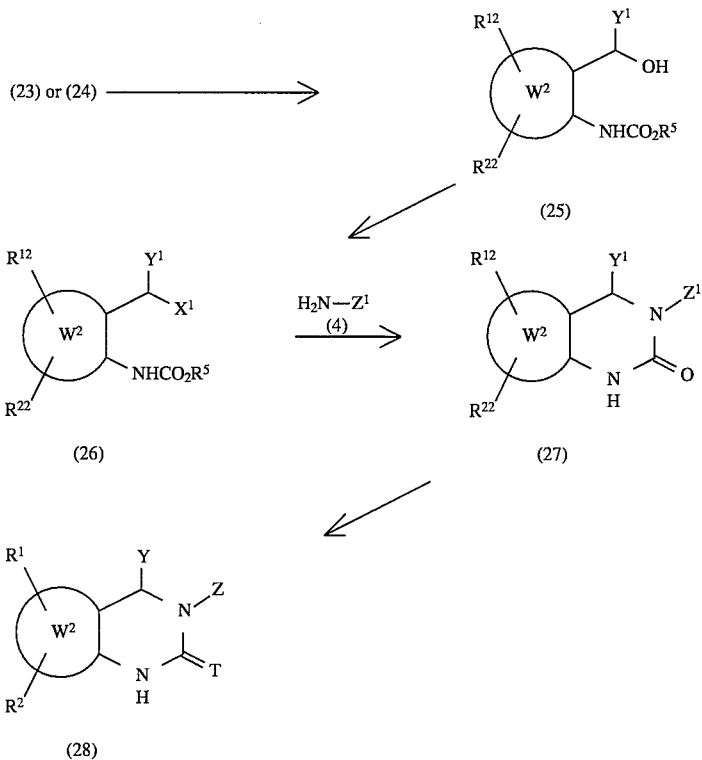

wherein ring $Y^1$, $Z^1$, $X^1$, Y, $R^1$, $R^2$, Z and T have the same meanings as above; ring $W^2$ represents a 5 to 10 membered cycloalkene or cycloalkane ring; $R^{12}$ has the same meaning as defined in $R^{11}$, except that the halogen atom is excluded; $R^{22}$ has the same meaning as defined in $R^{21}$, except that the halogen atom is excluded; $R^5$ represents a lower alkyl group; and the thick lines and dotted line in the formulas show the relative steric configuration of each carbon atoms at the adjacent bridgehead, and do not mean sole specific optical isomers, thus the same being applied in the following description.

The material compound of the formula (23) may be synthesized according to any method described in literatures (for example, J. Org. Chem., 1992, 57, 7285–7295; Chem. Lett. 1990, 1817–1820). If necessary, the compound (23) of the cis-configuration may be isomerized to the corresponding trans-isomer, the compound (24), before use. The isomerization can be performed by treating with a base in a solvent at a temperature between ambient temperature and the boiling point of the solvent. Preferably, the isomerization is performed in an alcoholic solvent, such as methanol, ethanol or tert.-butanol, using an alkoxide of sodium or potassium.

The ketone derivative of the formula (23) or (24) is treated with a reducing agent such as sodium borohydride in an alcoholic solvent, such as methanol or ethanol, at temperature between 0° C. and ambient temperature to give the alcohol derivative of the formula (25), which is then derived to the halide compound of the formula (26) by substituting the hydroxyl group to a halogen atom. The substitution to a halogen atom is suitably performed by the reaction with carbon tetrachloride, carbon tetrabromide, N-chlorosuccinimide or N-bromosuccinimide in a halogenated solvent, such as dichloromethane or 1,2-dichloroethane, at temperature between ambient temperature and the boiling point of the solvent, in the presence of triphenylphosphine. The iodine compound in the formula (26) can be obtained by treating the corresponding chlorine or bromine compound with sodium iodide in a solvent, such as acetone or dimethylformamide, at temperature between ambient temperature and 60° C.

The quinazolinone derivative of the formula (27) can be obtained by the reaction of a halide compound of the formula (26) with a primary amine of the formula (4) in a solvent at temperature between ambient temperature and the boiling point of the solvent in the presence of a base. As such solvents, aprotic polar solvents, such as dimethylformamide, dimethylsulfoxide or acetonitrile; alcoholic solvents, such as methanol or ethanol; and halogenated solvents, such as dichloroethane, may be used. As such bases, inorganic salts, such as potassium carbonate or sodium carbonate, and tertiary amines, such as triethylamine and N,N-diisopropylethylamine, may be used. Preferably, the reaction is suitably conducted in dimethylformamide in the presence of the tertiary amine, such as triethylamine or N,N-diisopropylethylamine at temperature of 50° C. to 100° C.

The quinazolinone derivative of the formula (28) can be obtained from the compound (27) using the procedure (a), (b), (c) or (d) employed in the compound (7), if required, or a combination thereof. In this instance, the derivative having $R^1$ and $R^2$ as halogen atoms can be synthesized from the compound having hydroxy groups as $R^{12}$ and $R^{22}$. The conversion reaction of such a substituent may be conducted according to the general procedure ordinarily employed in the field of organic synthetic chemistry.

The quaternary ammonium salt may be synthesized, for example, according to the following steps:

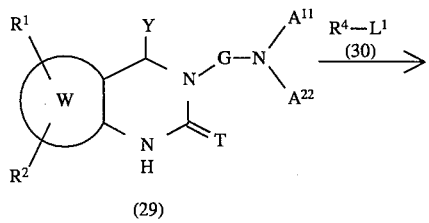

(29)

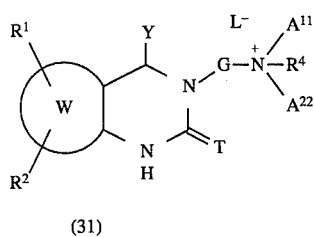

(31)

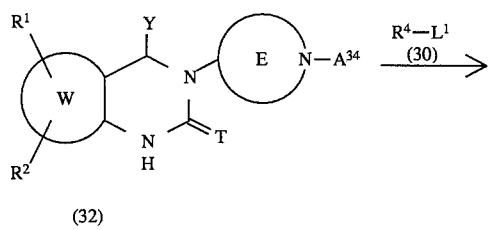

(32)

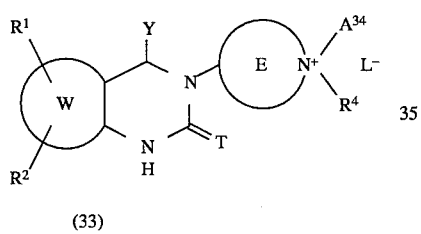

(33)

wherein ring W, ring E, $R^1$, $R^2$, Y, G and T have the same meanings as above; $A^{11}$ has the same meaning as defined in $A^1$, except that the hydrogen atom is excluded; $A^{22}$ has the same meaning as defined in $A^2$, except that the hydrogen atom is excluded; $A^{34}$ has the same meaning as defined in $A^3$, except that the hydrogen atom is excluded; $R^4$ represents a lower alkyl group; $L^1$ represents a leaving group; and $L^-$ represents a physiologically acceptable anion.

The quaternary ammonium salt can be obtained by mixing the quinazolinone derivative of the formula (29) or (32) with an alkylating agent of the formula (30) in a solvent at a temperature between ambient temperature and the boiling point of the solvent. If the reaction proceeds too slowly, heating up to approximately 120° C. in an autoclave is preferred.

As the preferable leaving group, chlorine, bromine and iodine atoms are illustrated. Preferable solvents include alcoholic solvents, such as methanol or ethanol, and ether solvents, such as tetrahydrofuran. The anion exchange can be performed by the reaction with an alkali metal salt, for example, sodium salt or potassium salt, containing a desirable anion.

DESCRIPTION OF THE PREFERRED EMBODIMENTS

Figure 1:
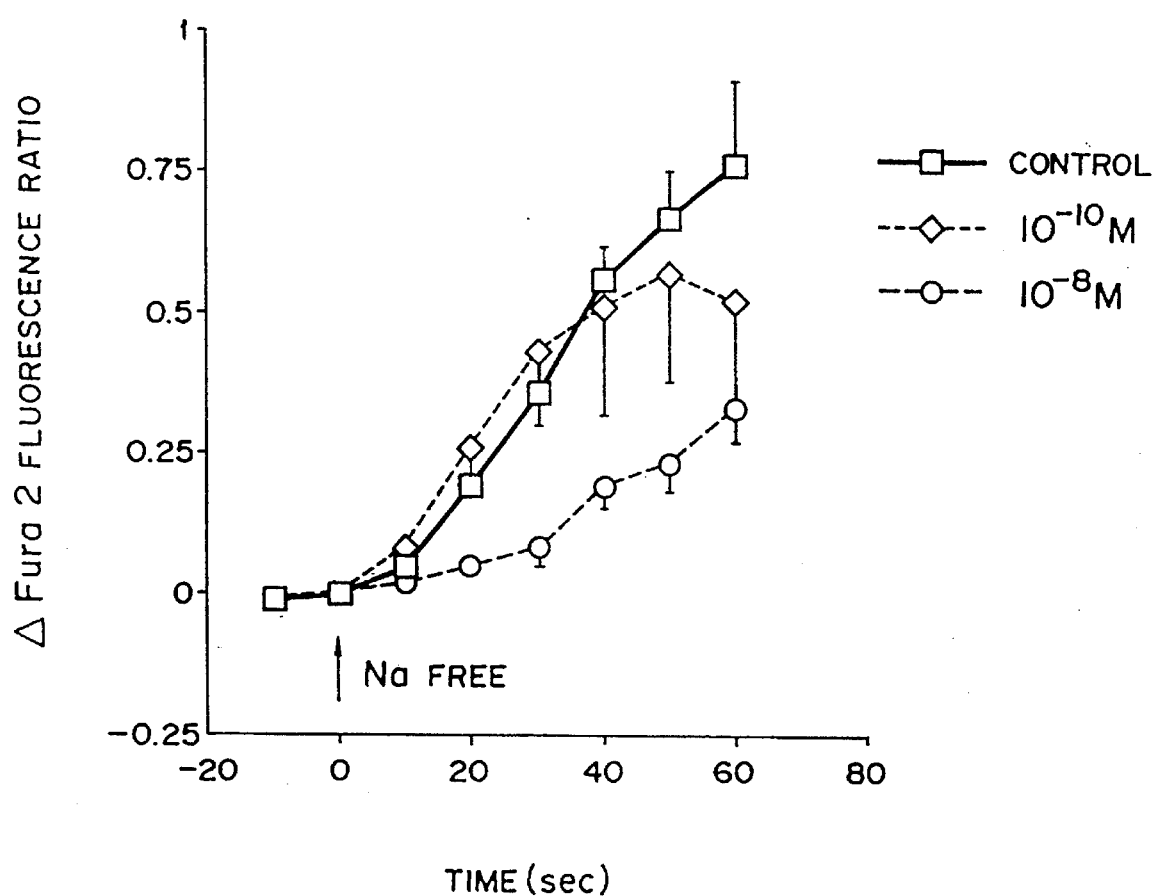
FIG. 1 is a graph showing the preventing effect of the Compound No. 6 on the increase in cytosolic $Ca^{2+}$ concentration through substitution with a $Na^+$ free solution (Preparation Example 24; citrate). The axis of abscissas represents the time period after the treatment with the test compound, and the axis of ordinates represents the change in Fura 2-AM fluorescence ratio during perfusion of the Na free HEPES solution.

The invention will more fully be described with respect to the following Preparation Examples, Formulation Examples and Testing Examples, which are, however, merely for illustration, and not for limitation. The nomenclature of the compounds is based upon the following structural formulas:

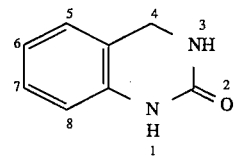

3, 4-dihydro-2(1H)quinazoline

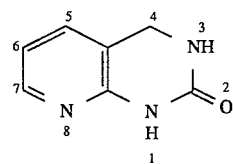

2-oxo-1, 2, 3, 4-tetrahydropyrido[2, 3-d]pyrimidine

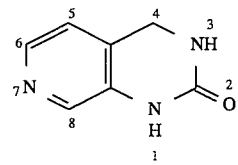

2-oxo-1, 2, 3, 4-tetrahydropyrido[3, 4-d]pyrimidine

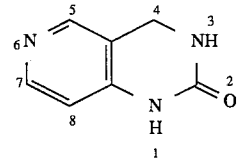

2-oxo-1, 2, 3, 4-tetrahydropyrido[4, 3-d]pyrimidine

The formulas of the compounds prepared in the following Preparation Examples are shown below:

Preparation Example 1

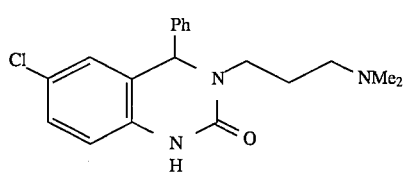

Preparation Example 2

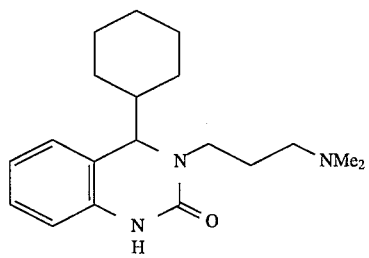

Prelaration Example 3

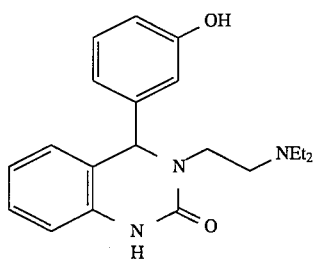

Hereinafter, Q represents the formula:

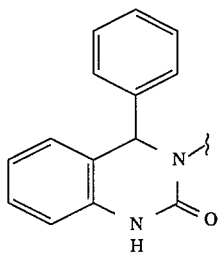

Preparation Example 4

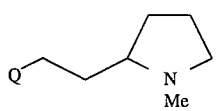

Preparation Example 5

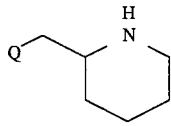

Preparation Example 6

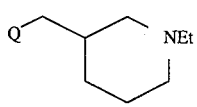

Preparation Example 7

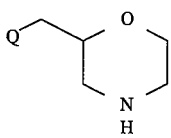

Preparation Example 8

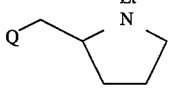

Preparation Example 9

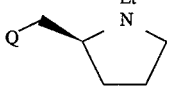

Preparation Example 10

Preparation Example 11

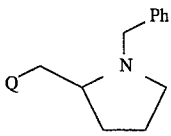

Preparation Example 12

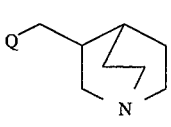

Preparation Example 13

Preparation Example 14

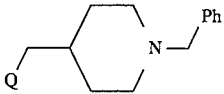

Preparation Example 15

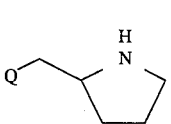

-continued

Preparation Example 16

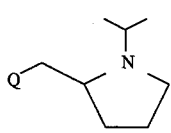

Preparation Example 17

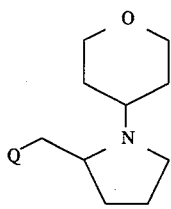

Preparation Example 18

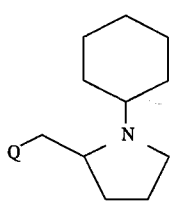

Preparation Example 19

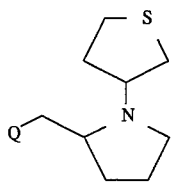

Preparation Example 20

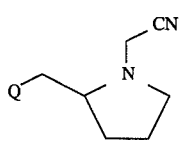

Preparation Example 21

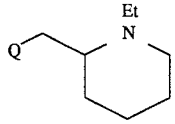

Preparation Example 22

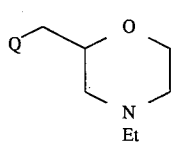

Preparation Example 23

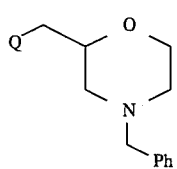

-continued

Preparation Example 24

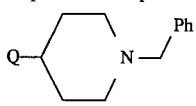

Preparation Example 25

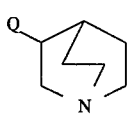

Preparation Example 26

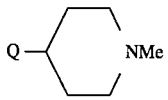

Preparation Example 27

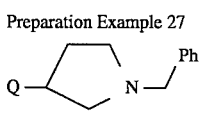

Preparation Example 28

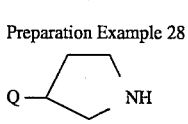

Preparation Example 29

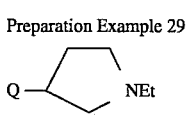

Preparation Example 30

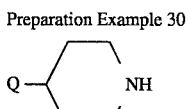

Preparation Example 31

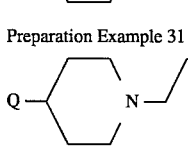

Preparation Example 32

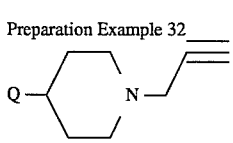

Preparation Example 33

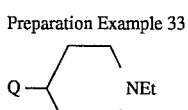

Preparation Example 34

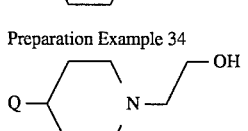

Preparation Example 35

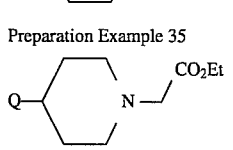

Preparation Example 36
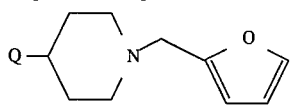

Preparation Example 37
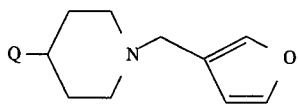

Preparation Example 38
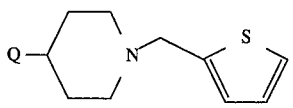

Preparation Example 39
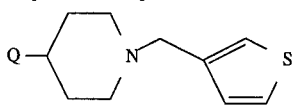

Preparation Example 40
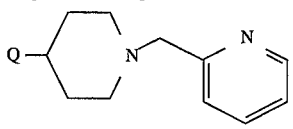

Preparation Example 41
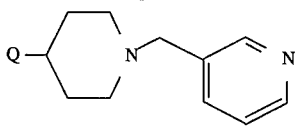

Preparation Example 42
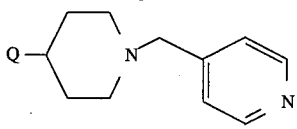

Preparation Example 43
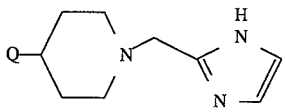

Preparation Example 44
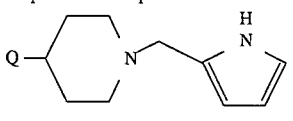

Preparation Example 45
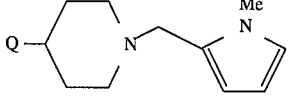

Preparation Example 46
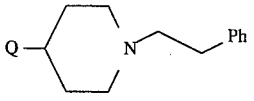

Preparation Example 47
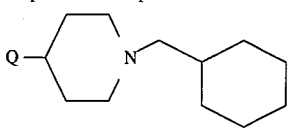

Preparation Example 48
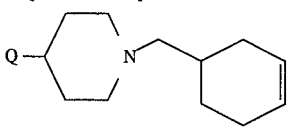

Preparation Example 49
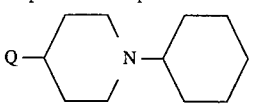

Preparation Example 50
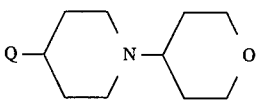

Preparation Example 51
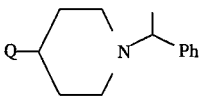

Preparation Example 52
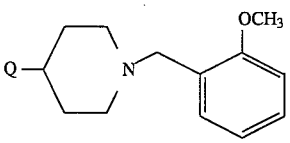

Preparation Example 53
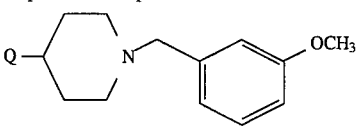

Preparation Example 54
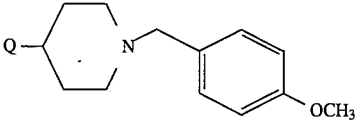

Preparation Example 55
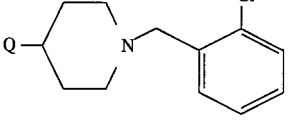

Preparation Example 56
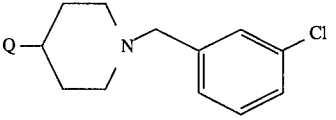

-continued

Preparation Example 57
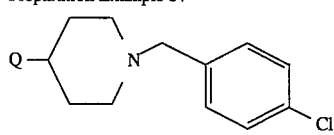

Preparation Example 58
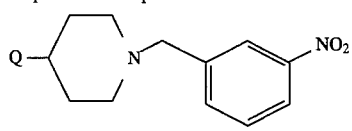

Preparation Example 59
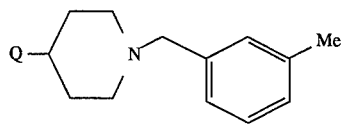

Preparation Example 60
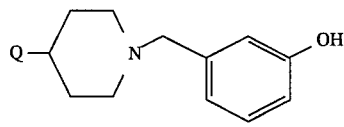

Preparation Example 61
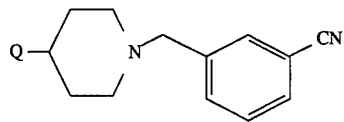

Preparation Example 62
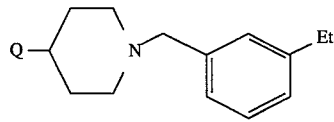

Preparation Example 63
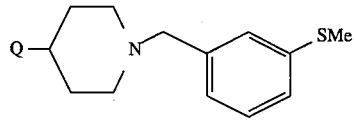

Preparation Example 64
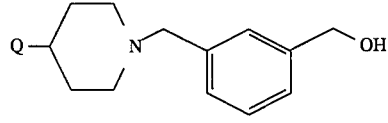

Preparation Example 65
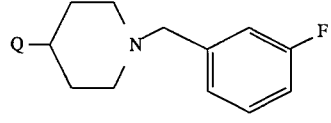

Preparation Example 66
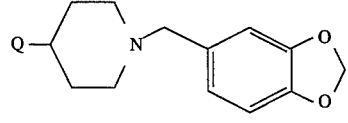

-continued

Preparation Example 67
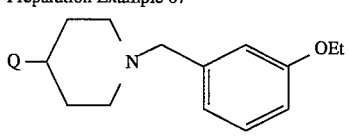

Preparation Example 68
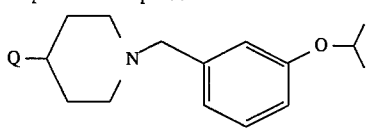

Preparation Example 69
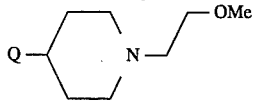

Preparation Example 70
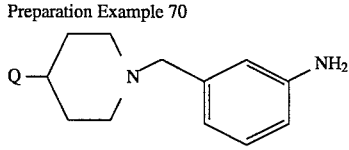

Preparation Example 71
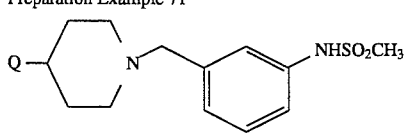

Preparation Example 72
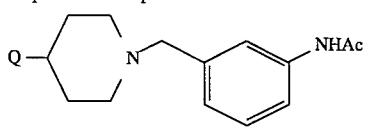

Preparation Example 73
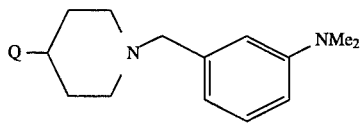

Preparation Example 74
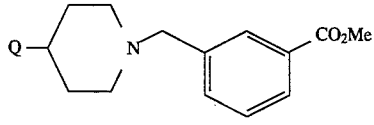

Preparation Example 75
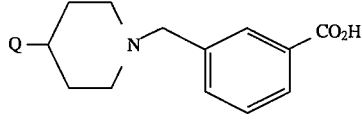

Preparation Example 76
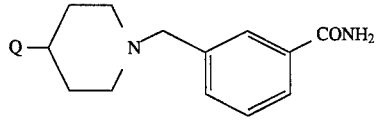

27
-continued
Preparation Example 77
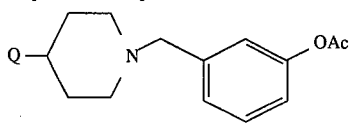
Preparation Example 78
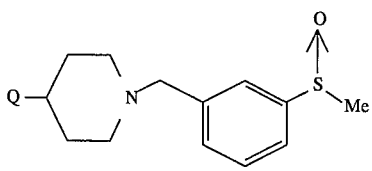
Preparation Example 79
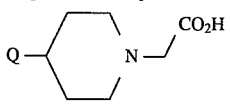
Preparation Example 80
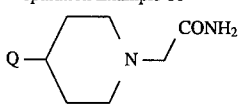
Preparation Example 81
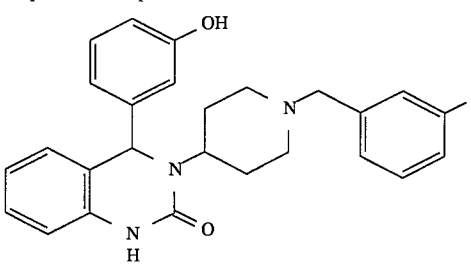
Preparation Example 82
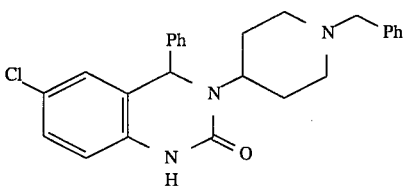
Preparation Example 83
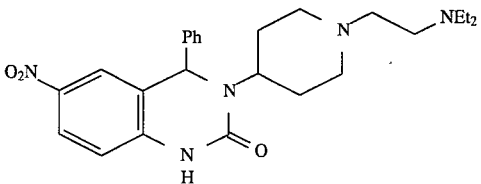
Preparation Example 84
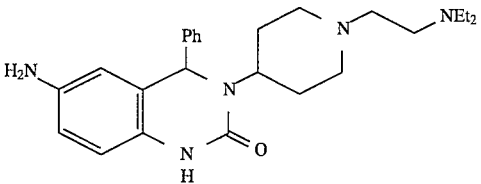
28
-continued
Preparation Example 85
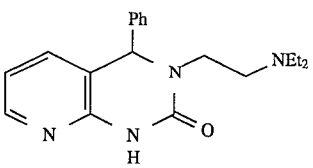
Preparation Example 86
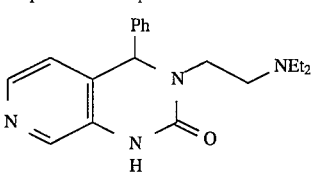
Preparation Example 87
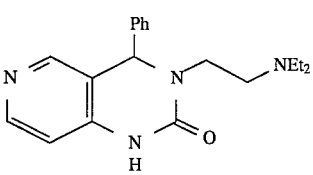
Preparation Example 88
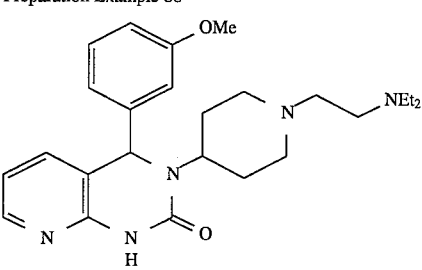
Preparation Example 89
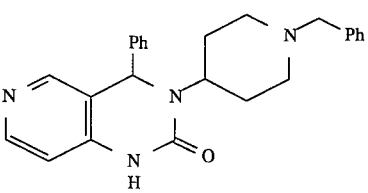
Preparation Example 90
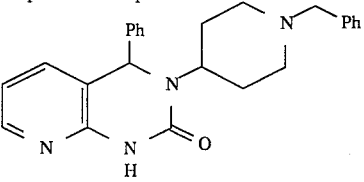
Preparation Example 91
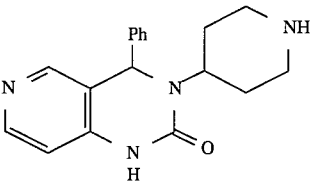

Preparation Example 92
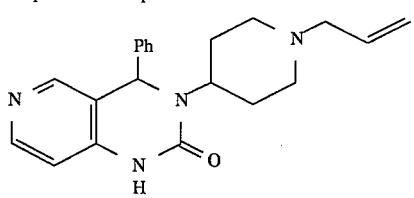
Preparation Example 93
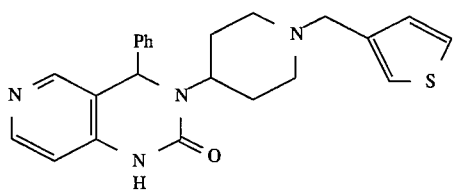
Preparation Example 94
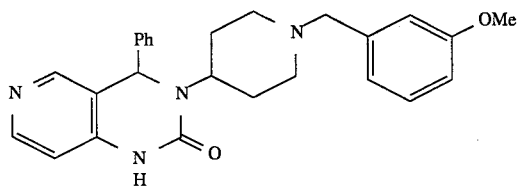
Preparation Example 95
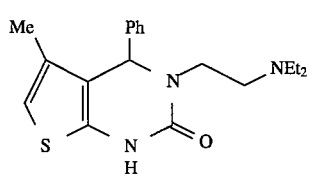
Preparation Example 96
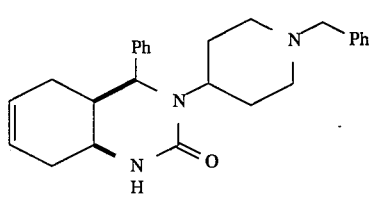
Preparation Example 97
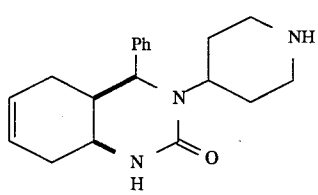
Preparation Example 98
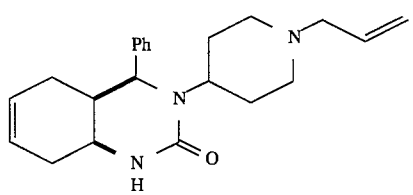
Preparation Example 99
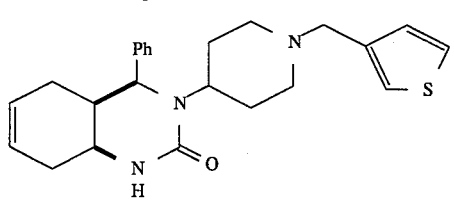
Preparation Example 100
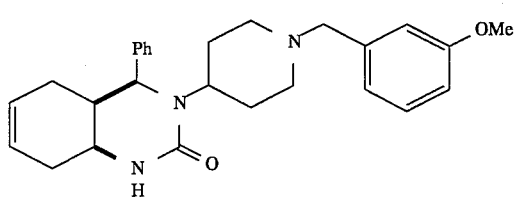
Preparation Example 101
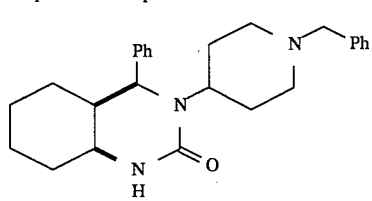
Preparation Example 102
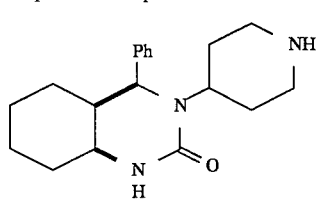
Preparation Example 103
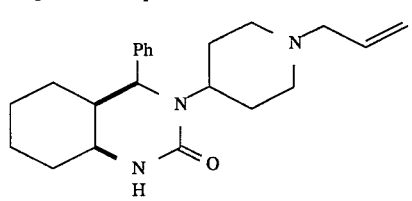
Preparation Example 104
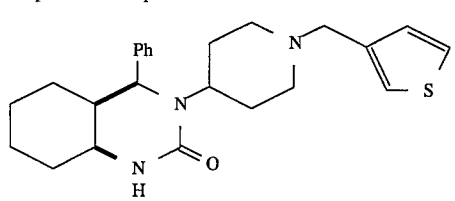
Preparation Example 105
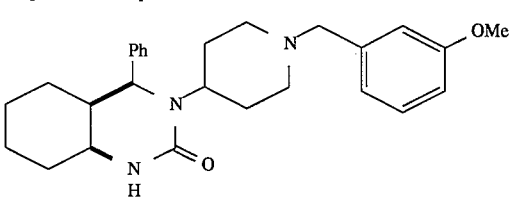

Preparation Example 106

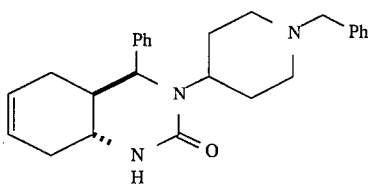

Preparation Example 107

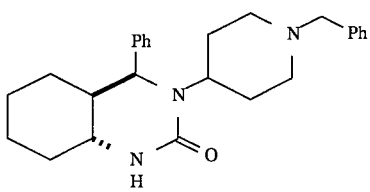

Preparation Example 108

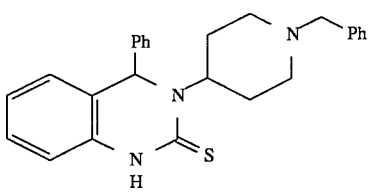

Preparation Example 109

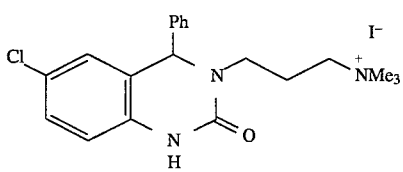

Preparation Example 110

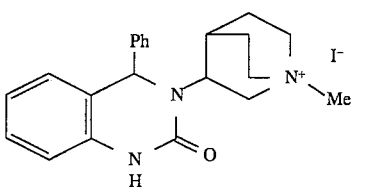

Preparation Example 111

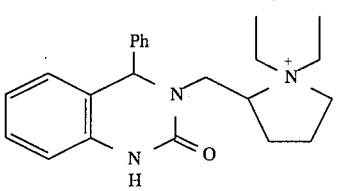

PREPARATION EXAMPLE 1

Synthesis of 6-chloro-3-[3-(dimethylamino)propyl]-4-phenyl-3,4-dihydro-2(1H)-quinazolinone The compound was synthesized according to the method disclosed in Chem. Pharm. Bull., 1981, 29, 2135–56.

(a) Synthesis of 5-chloro-2-trichloroacetylaminobenzophenone

To a solution of 23.2 g (100 mmol) of 2-amino-5-chlorobenzophenone and 11 g (110 mmol) of triethylamine in 200 mL of tetrahydrofuran was added dropwise 20 g (110 mmol) of trichloroacetyl chloride at temperature of 5° C. to 15° C. After being stirred for 3 hours at ambient temperature, the reaction mixture was poured into water and the mixture was extracted with ethyl acetate. The organic layer separated was washed with water and then with brine, dried on anhydrous sodium sulfate and concentrated in vacuo. The resulting crude crystals were recrystallized from ethanol to give 33.8 g (89.9 mmol) of the title compound.

(b) Synthesis of 6-chloro-3-[3-(dimethylamino)propyl]-4-phenyl-4-(trichloromethyl)-3,4-dihydro-2(1H)-quinazolinone To a solution of 3.77 g (10 mmol) of 5-chloro-2-trichloroacetylaminobenzophenone in 50 mL of dimethylsulfoxide was added 1.23 g (12 mmol) of 3-dimethylaminopropylamine at ambient temperature, and the mixture was stirred for 24 hours. The reaction mixture was poured onto 200 mL of ice water, and the crystals formed were separated by filtration. The resulting crude crystals were recrystallized from a mixed solvent of chloroform and dimethyl formamide to give 3.97 g (8.6 mmol) of the title compound.

(c) Synthesis of 6-chloro-3-[(3-dimethylamino)propyl]-4-phenyl-3,4-dihydro-2(1H)-quinazolinone To a solution of 3.69 g (8 mmol) of 6-chloro-3-[3-(dimethylamino)propyl]-4-phenyl-4-(trichloromethyl)-3,4-dihydro-2(1H)-quinazolinone in 80 mL of dimethylformamide was added 605 mg (16 mmol) of sodium borohydride at temperature of 5° C. to 15° C., and the mixture was stirred for 3 hours. Then, the reaction mixture was poured onto 300 mL of ice water, and the mixture was extracted with ethyl acetate. The organic layer separated was washed with water and then with brine, dried on anhydrous sodium sulfate and concentrated in vacuo. The resulting solid was recrystallized from ethanol to give 2.23 g (6.5 mmol) of the title compound.

A solution of 1.72 g (5.0 mmol) of the above free base in ethanol was mixed with a solution of 1.05 g (5 mmol) of citric acid monohydrate in ethanol at ambient temperature, and the mixture was stirred for one hour. The solvent was distilled away in vacuo, and the resulting solid was recrystallized from ethanol to give 2.55 g (4.6 mmol) of the citric acid salt of the title compound.

Melting point: 157°–159° C. (recrystallized from ethanol)

PREPARATION EXAMPLE 2

Synthesis of 3-[3-(dimethylamino)propyl]-4-cyclohexyl-3,4-dihydro-2(1H)-quinazolinone In similar way as in Preparation Example 1, the title compound was synthesized from (2-aminobenzoyl)cyclohexane and 3-(dimethylamino)propylamine.

$^1$H NMR(CDCl$_3$) δ; 7.65(1H, brs), 7.17(1H, m), 6.94(2H, m), 6.73(1H, m), 4.16(1H, d, J=5.0 Hz), 4.04(1H, m), 3.02(1H, m), 2.28(2H, m), 2.17(6H,s), 1.72(7H, m), 1.04(5H, m), 0.80(1H, m).

Melting point: 124°–125° C. (recrystallized from ethanol)
Melting point at the HCl salt: 183°–184° C. (recrystallized from diethyl ether/ethanol)

PREPARATION EXAMPLE 3

Synthesis of 3-[2-(diethylamino)ethyl]-4-(3-hydroxy-phenyl)-3,4-dihydro-2(1H)-quinazolinone (a) Synthesis of 3-[2-(diethylamino)ethyl]-4-(3-benzyloxyphenyl)-3,4-dihydro-2(1H)-quinazolinone In similar way as in Preparation Example 1, the title compound was synthesized from 2-amino-3'-benzyloxybenzophenone and 2-(diethylamino)ethylamine.

$^1$H NMR(CDCl$_3$) δ; 7.29–7.43(5H, m), 7.22(1H, m), 7.12(1H, m), 6.83–6.97(6H, m), 6.66(1H, dd, J=7.9, 1.0 Hz), 5.63(1H, s), 5.01(2H, s), 3.77–3.87(1H, m), 2.93–3.03(1H, m), 2.54–2.71(1H, m), 2.39–2.52(5H, m), 0.97(6H, t, J=7.3 Hz).

Melting point: 128°–129° C. (recrystallized from ethanol)

(b) Synthesis of 3-[2-(diethylamino)ethyl]-4-(3-hydroxyphenyl)-3,4-dihydro-2(1H)-quinazolinone To a solution of 2.0 g (4.66 mmol) of 3-[2(diethylamino)ethyl]-4-(3-benzyloxyphenyl)-3,4 -dihydro-2(1H)-quinazolinone in 100 mL of methanol was added 200 mg of 5 % palladium-carbon, and the mixture was stirred for 5 hours under a hydrogen atmosphere at ambient temperature. The reaction mixture was filtered through cerite, and the filtrate was concentrated in vacuo. The crystals formed was recrystallized from methanol to give 1.30 g (3.83 mmol) of the title compound.

$^1$H NMR(DMSO-d$_6$) δ; 9.45(1H, s, D$_2$O exchangeable, 9.33(1H, s), 7.04–7.15(3H, m), 6.62–6.83(5H, m), 5.62(1H, s), 3.68(1H, m), 2.77(1H, m), 2.34–2.56 (6H, m), 0.89(6H, t, J=7.3 Hz).

Melting point: 208°–210° C. (recrystallized from methanol)

Melting point of the HCl salt: 247°–249° C. (recrystallized from diethyl ether/ethanol)

PREPARATION EXAMPLE 4

Synthesis of 3-[2-(1-methylpyrrolidin-2-yl)ethyl]-4 -phenyl-3,4-dihydro-2-(1H)-quinazolinone In similar way as in Preparation Example 1, the title compound, as an about 1:1 mixture of the diastereomers, was synthesized from 2-aminobenzophenone and 2-(2-aminoethyl)-1-methylpyrrolidine.

$^1$H NMR(CDCl$_6$) δ; 7.23–7.34(5H, m), 7.13(1H, m), 7.00(1H, m), 6.87(1H, m), 6.71(1H, m), 5.51(0.5H, s), 5.49(0.5H, s), 3.89–4.00(0.5H, m), 3.73–3.84 (0.5H, m), 2.96–3.07(1H, m), 2.75–2.86(1H, m), 2.25(1.5H, s), 2.23(1.5H, s), 1.84–2.14(4H, m), 1.36–1.78(4H, m).

Melting point: 154°–157° C. (recrystallized from diethyl ether/ethanol)

PREPARATION EXAMPLE 5

Synthesis of 3-(piperidin-2-yl)methyl-4-phenyl-3,4 -dihydro-2(1H)-quinazolinone

In similar way as in Preparation Example 1, the title compound, as an about 1:1 mixture of the diastereomers, was synthesized from 2-aminobenzophenone and 2-aminomethylpiperidine.

$^1$H NMR(CDCl$_3$) δ; 7.93(1H, m), 6.74–7.49(9H, m), 5.56(0.5H, s), 5.52(0.5H, s), 3.79–4.00(1H, m), 2.52–3.09(4H, m), 1.10–1.80(6H, m).

Melting point: 193°–195° C. (recrystallized from diethyl ether/ethanol)

PREPARATION EXAMPLE 6

Synthesis of 3-(1-ethylpiperidin-3-yl)methyl-4-phenyl -3,4-dihydro-2-(1H)-quinazolinone In similar way as in Preparation Example 1, the title compound, as an about 2:3 mixture of the diastereomers, was synthesized from 2-aminobenzophenone and 3-(aminomethyl)-1-ethylpiperidine.

$^1$H NMR(CDCl$_3$) δ; 8.04(1H, brs), 7.22–7.35(5H, m), 6.74–7.16(4H, m), 5.52(0.4H, s), 5.47(0.6H, s), 3.94(1H, m), 2.59–3.01(3H, m), 2.44(2H, m), 1.55–2.19 (7H, m), 1.05(3H, m).

Melting point: approximately 250° C. (decomposed, recrystallized from ethanol)

PREPARATION EXAMPLE 7

Synthesis of 3-(morpholin-2-yl)methyl-4-phenyl-3,4 -dihydro-2(1H)-quinazolinone

In similar way as in Preparation Example 1, the title compound, as an about 1:1 mixture of the diastereomers, was synthesized from 2-aminobenzophenone and 2-aminomethylmorpholine.

$^1$H NMR(CDCl$_3$) δ; 7.80(0.5H, brs), 7.71(0.5H, brs), 6.68–7.40(9H, m), 5.74(0.5H, s), 5.69(0.5H, s), 3.35–3.96(4H, m), 2.43–3.03(5H, m).

PREPARATION EXAMPLE 8

Synthesis of 3-(1-ethylpyrrolidin-2-yl)methyl-4-phenyl -3,4-dihydro-2(1H)-quinazolinone In similar way as in Preparation Example 1, 1.02 g of the title compound, as a mixture of the diastereomers, was synthesized from 2-aminobenzophenone and 2-(aminomethyl)-1-ethylpyrrolidine. The mixed diastereomers were separated each other by means of column chromatography (silica gel, 1:9 methanol chloroform) to give 589 mg of Diastereomer A, 254 mg of Diastereomer B and 150 mg of the mixture. Diastereomer A had a higher Rf value, and Diastereomer B, a lower Rf value, on thin layer chromatography (developed with 1:9 methanol:chloroform).

Diastereomer A:

$^1$H NMR(CDCl$_3$) δ; 9.59(1H, brs), 6.80–7.35(9H, m), 5.81(1H, s), 4.04(1H, dd, J=14, 3 Hz), 3.18(1H, m), 2.71–3.02(3H, m), 1.61–2.39(6H, m), 1.17(3H, t, J=7 Hz).

Melting point of the HCl salt: over 250° C. (recrystallized from ethanol)

Diastereomer B:

$^1$H NMR (CDCl$_3$) δ; 9.02(1H, brs), 6.81–7.39(9H, m), 5.83(1H, s), 3.94(1H, dd, J=14, 6 Hz), 3.29(1H, m), 2.83–3.11(3H, m), 2.27–2.46(2H, m), 1.62–1.93(4H, m), 1.06(3H, t, J=7 Hz).

Melting point: 151°–153° C. (recrystallized from ethanol)

PREPARATION EXAMPLE 9

Synthesis of 3-[(2S)-1-ethylpyrrolidin-2-yl]methyl-4-phenyl-3,4-dihydro-2(1H)-quinazolinone In similar way as in Preparation Example 8, but using (S)-2-aminomethyl-1-ethylpyrrolidine, the title compound was synthesized, as a mixture of the diastereomers. The mixed diastereomers were separated each other by means of column chromatography (silica gel, 1:9 methanol chloroform) to give 11.8 g of Diastereomer A1 and 4.62 g of Diastereomer B1. Diastereomer A1 had a higher Rf value, and Diastereomer B1, a lower Rf value, on thin layer chromatography (developed with 1:9 methanol:chloroform). Diastereomer A1 was an optically active form of Diastereomer A synthesized in Preparation Example 8, and Diastereomer B1, an optically active form of Diastereomer B.

Diastereomer A1 :

Melting point of the HCl salt: 299.5°–302° C. (recrystallized from ethanol)

$[α]_D^{24}$+177.3° (c 1.07 in methanol)

Diastereomer B1:
Melting point of the HCl salt: 302.5°–304° C. (recrystallized from ethanol)
$[\alpha]_D^{24}$ –204° (c 0.943 in methanol)

PREPARATION EXAMPLE 10

Synthesis of 3-[(2R)-1-ethylpyrrolidin-2-yl]methyl-4-phenyl-3,4-dihydro-2(1H)-quinazolinone In similar way as in Preparation Example 8, but using (R)-2-aminomethyl-1-ethylpyrrolidine, the title compound was synthesized, as a mixture of the diastereomers. The mixed diastereomers were separated each other by means of column chromatography (silica gel, 1:9 methanol:chloroform) to give 9.89 g of Diastereomer A2 and 4.12 g of Diastereomer B2. Diastereomer A2 had a higher Rf value, and Diastereomer B2, a lower Rf value, on thin layer chromatography (developed with 1:9 methanol:chloroform). Diastereomer A2 was an optically active form of Diastereomer A synthesized in Preparation Example 8, and an enantiomer of Diastereomer A1 synthesized in Preparation Example 9. Similarly, Diastereomer B2 is an optically active form of Diastereomer B, and an enantiomer of Diastereomer B1.

Diastereomer A2 :
Melting point of the HCl salt: 305°–306.5° C. (recrystallized from ethanol)
$[\alpha]_D^{24}$ –178.2° (c 0.995 in methanol)

Diastereomer B2 :
Melting point of the HCl salt: 305°–307.5° C. (recrystallized from ethanol)
$[\alpha]_D^{24}$ +203.6° (c 0.978 in methanol)

PREPARATION EXAMPLE 11

Synthesis of 3-(1-benzylpyrrolidin-2-yl)methyl-4-phenyl-3,4-dihydro-2(1H)-quinazolinone In similar way as in Preparation Example 1, the title compound, as an about 2:3 mixture of the diastereomers, was synthesized from 2-aminobenzophenone and 2-(aminomethyl)-1-benzylpyrrolidine. The HCl salt:

$^1$H NMR(CD$_3$OD) δ; 6.82–7.90(14H, m), 5.66(0.4H, s), 5.45(0.6H, s), 3.78–4.87(4H, m), 2.86–3.63 (3H, m), 1.67–2.69(4H, m).

PREPARATION EXAMPLE 12

Synthesis of 3-(quinuclidin-3-yl)methyl-4-phenyl-3,4-dihydro-2(1H)-quinazolinone In similar way as in Preparation Example 1, the title compound, as an about 1:1 mixture of the diastereomers, was synthesized from 2-aminobenzophenone and 3-aminomethylquinuclidine. Borane (BH$_3$) coordinated to the nitrogen atom in the quinuclidine was removed by heating under reflux in 2N HCl/tetrahydrofuran. The HCl salt:

$^1$H NMR(CDCl$_3$) δ; 8.96(0.5H, brs), 8.87(0.5H, brs), 7.22–7.36(5H, m), 7.01–7.16(2H, m), 6.79–6.90(2H, m), 5.47(0.5H, s), 5.42(0.5H, s), 3.88–4.19(1H, m), 2.65–3.66(6H, m), 2.34–2.48(1H, m), 2.01–2.16(1H, m), 1.40–1.99(5H, m).

PREPARATION EXAMPLE 13

Synthesis of 3-(quinuclidin-4-yl)methyl-4-phenyl-3,4-dihydro-2(1H)-quinazolinone In similar way as in Preparation Example 1, the title compound was synthesized from 2-aminobenzophenone and 4-aminomethylquinuclidine.

$^1$H NMR(CDCl$_3$) δ; 7.10–7.47(7H, m), 6.88–7.00(1H, m), 6.68–6.77(1H, m), 5.39(2H, s), 3.93(2H, d, J=14 Hz), 2.89(6H, brt, J=8 Hz), 2.44(2H, d, J=14 Hz), 1.36–1.65(6H, m).

PREPARATION EXAMPLE 14

Synthesis of 3-(1-benzylpiperidin-4-yl)methyl-4-phenyl-3,4-dihydro-2(1H)-quinazolinone In similar way as in Preparation Example 1, the title compound was synthesized from 2-aminobenzophenone and 4-(aminomethyl)-1-benzylpiperidine.

$^1$H NMR(CDCl$_3$) δ; 7.48(1H, s), 7.20–7.31(10H, m), 7.02–7.15(2H, m), 6.85–6.91(1H, m), 6.71(1H, d, J=7.9 Hz), 5.41(1H, s), 3.90(1H, dd, J=14, 7.3 Hz), 3.47(2H, s), 2.85(2H, brd, J=11 Hz), 2.56(1H, dd, J=14, 6.9 Hz), 1.87–1.95(2H, m), 1.66–1.8(3H, m), 1.24–1.42(2H, m).

Melting point: 163°–165° C. (recrystallized from ethanol)

PREPARATION EXAMPLE 15

Synthesis of 3-(pyrrolidin-2-yl)methyl-4-phenyl-3,4-dihydro-2(1H)-quinazolinone

To a solution of 15.98 g (40.2 mmol) of 3-(1-benzylpyrrolidin-2-yl)methyl-4-phenyl-3,4-dihydro-2(1H)-quinazolinone in 300 mL ethanol were added 13.61 g (216 mmol) of ammonium formate and 1.64 g of 10 % palladium-carbon, and the mixture was heated under reflux for 5 hours. After being cooled, the reaction mixture was filtered through cerite, and the filtrate was concentrated in vacuo. To the residue was added an aqueous saturated sodium hydrogencarbonate solution, and the mixture was extracted with chloroform. The organic layer separated was dried on potassium carbonate, and then concentrated in vacuo. The residue was purified by means of column chromatography (silica gel, 5:100:900 aqueous ammonia methanol:chloroform) to give 9.32 g (30.3 mmol) of the title compound as an about 1:1 mixture of the diastereomers.

$^1$H NMR(CDCl$_3$) δ; 8.32(1H, m), 7.21–7.37(5H, m), 6.99–7.14(2H, m), 6.74–6.89(2H, m), 5.81(0.5H, s), 5.64(0.5H, s), 3.89–4.03(1H, m), 3.41–3.51(1H, m), 2.67–3.07(3H, m), 2.02(1H, brs), 1.64–1.89(3H, m), 1.31(1H, m).

Melting point: 163°–164° C. (recrystallized from ethyl acetate)

PREPARATION EXAMPLE 16

Synthesis of 3-[1-(2-propyl)pyrrolidin-2-yl]methyl-4-phenyl-3,4-dihydro-2(1H)-quinazolinone To a solution of 554 mg (1.80 mmol) of 3-(pyrrolidin-2-yl)methyl-4-phenyl-3,4-dihydro-2(1H)-quinazolinone in 30 mL of methanol were added 660 mg of 10% HCl/ethanol, 523 mg (9.00 mmol) of acetone and 566 mg (9.00 mmol) of sodium cyanoborohydride under ice-cooling. After being stirred for 10 hours at ambient temperature, the reaction mixture was concentrated in vacuo. To the residue was added an aqueous saturated sodium hydrogen-carbonate solution, and the mixture was extracted with chloroform. The organic layer separated was dried on potassium carbonate and then concentrated in vacuo. The residue was subjected to column chromatography (silica gel, 1:9 methanol:chloroform) for isolation and purification to give 279 mg of Diastereomer A and 71 mg of Diastereomer B. Diastereomer A had a higher Rf value, and Diastereomer B, a lower Rf value, on thin layer chromatography (developed with 1:9 methanol:chloroform).

Diasteromer A:

¹H NMR(CDCl₃) δ; 9.80(1H, brs), 7.19–7.36(5H, m), 7.00–7.13(2H, m), 6.82–6.87(2H, m), 5.72(1H, s), 3.86(1H, dd, J=14, 3 Hz), 3.18(1H, m), 2.90–2.97 (2H, m), 2.76(1H, dd, J=14, 9 Hz), 2.46–2.52(1H, m), 1.65–1.82(4H, m), 1.20(3H, d, J=7 Hz), 1.06(3H, d, J=7 Hz).

Diastereomer B: HCl salt:

¹H NMR (CD₃ OD ) δ; 7.29–7.40(5H, m), 6.89–7.23(4H, m), 5.70(1H, s), 3.81–3.89(1H, m), 3.38–3.61(3H, m), 3.18–3.27(1H, m), 1.88–2.13(5H, m), 1.31(3H, d, J=7 Hz ), 1.14 (3H, d, J=7 Hz).

Melting point: over 250° C. (recrystallized from ethanol)

PREPARATION EXAMPLE 17

Synthesis of 3-[1-(tetrahydropyran-4-yl)pyrrolidin-yl]methyl-4-phenyl-3,4-dihydro-2(1H)-quinazolinone In similar way as in Preparation Example 16, the title compound, as a mixture of the diastereomers, was obtained from 3-(pyrrolidin-2-yl)methyl-4-phenyl-3,4-dihydro-2(1H)-quinazolinone and tetrahydro-4H-pyran-4-one. Diastereomer A had a higher Rf value, and Diastereomer B, a lower Rf value, on thin layer chromatography (developed with 1:9 methanol:chloroform).

Diastereomer A: HCl salt:

¹H NMR(CD₃ OD) δ: 7.28–7.40(5H, m), 7.06–7.21(2H, m), 6.87–6.96(2H, m), 5.77(1H, s), 3.86–4.12(3H, m), 3.22–3.64(7H, m), 1.62–2.15(8H, m).

Melting point: over 250° C. (recrystallized from ethanol)

Diastereomer B: HCl salt:

¹H NMR(CD₃ OD) δ; 6.87–7.53(9H, m), 5.80(1H, s), 3.74–3.96(3H, m), 3.26–3.71(6H, m), 1.61–2.15(9H, m).

PREPARATION EXAMPLE 18

Synthesis of 3-(1-cyclohexylpyrrolidin-2-yl)methyl-4-phenyl-3,4-dihydro-2(1H)-quinazolinone In similar way as in Preparation Example 16, the title compound, as a mixture of the diastereomers, was obtained from 3-(pyrrolidin-2-yl)methyl-4-phenyl-3,4-dihydro-2(1H)-quinazolinone and cyclohexanone. Diastereomer A had a higher Rf value, and Diastereomer B, a lower Rf value, on thin layer chromatography (developed with 1:9 methanol:chloroform).

Diastereomer A: HCl salt:

¹H NMR(CD₃ OD) δ; 6.84–7.37(9H, m), 5.77(1H, s), 3.84–4.04(2H, m), 3.40–3.52(1H, m), 3.15–3.33(2H, m), 1.47–2.24(9H, m), 1.14–1.43(6H, m).

Diastereomer B: HCl salt:

¹H NMR(CD₃ OD) δ; 7.30–7.43(5H, m), 7.18–7.24(1H, m), 7.06–7.09(1H, m), 6.90–6.99(2H, m), 5.75(1H, s). 3.87–3.92(1H, m), 3.58–3.82(2H, m), 3.42–3.51 (1H, m), 3.24–3.34(1H, m), 3.03–3.13(1H, m), 1.81–2.17 (8H, m), 1.64(1H, m), 1.13–1.45(5H, m).

Melting point: over 250° C. (recrystallized from isopropyl alcohol)

PREPARATION EXAMPLE 19

Synthesis of 3-[1-(tetrahydrothiophen-3-yl)pyrrolidin-2-yl]methyl-4-phenyl-3,4-dihydro-2 (1H)-quinazolinone In similar way as in Preparation Example 16, the title compound, as a mixture of the diastereomers, is obtained from 3-(pyrrolidin-2-yl)methyl-4-phenyl-3,4-dihydro-2(1H)-quinazolinone and tetrahydrothiophen-3-one. This compound retained 4 kinds of the diastereomers, which were named Diastereomers A, B, C and D in the sequence of the Rf values from the higher to the lower, on thin layer chromatography (developed with 1:9 methanol:chloroform).

By means of column chromatography (developed with 1:9 methanol:chloroform), a mixture of Diastereomers A and B and a mixture of Diastereomers C and D were isolated from the mixed diastereomers.

A mixture of Diastereomers A and B:

¹H NMR(CDCl₃) δ; 8.05–8.12(1H, m), 6.73–7.32(9H, m), 5.70(0.4H, s), 5.68(0.6H, s), 3.68–3.86(2H, m), 2.45–3.20(10H, m), 1.74–2.20(4H, m).

Melting point: 123°–126° C. (recrystallized from ethanol)

A mixture of Diastereoisomers C and D: HCl salt:

¹H NMR(CD₃ OD) δ; 7.29–7.39(5H, m), 7.18–7.24(1H, m), 6.90–7.09(3H, m), 5.76(1H, s), 3.79–3.91(3H, m), 3.58–3.64(2H, m), 3.29–3.40(1H, m), 2.70–3.08 (4H, m), 1.93–2.36(6H, m).

Melting point: over 250° C. (recrystallized from isopropyl alcohol)

PREPARATION EXAMPLE 20

Synthesis of 3-(1-cyanomethylpyrrolidin-2-yl)methyl-4-phenyl-3,4-dihydro-2(1H)-quinazolinone A solution of 203 mg (0.66 mmol) of 3-(pyrrolidin-2-yl)methyl-4-phenyl-3,4-dihydro-2(1H)-quinazolinone, 95 mg (0.79 mmol) of bromoacetonitrile and 283 mg (2.8 mmol) of triethylamine in 5 mL of dimethyl-formamide was stirred for 6 hours at 70° C. After being cooled, the reaction mixture was diluted with water, and the mixture was extracted with chloroform. The organic layer separated was washed with water, dried on potassium carbonate and concentrated in vacuo. The residue was purified by means of column chromatography (silica gel, 1:9 methanol:chloroform) to give 226 mg (0.65 mmol) of the title compound as an about 1:2 mixture of the diastereomers.

¹H NMR(CDCl₃) δ; 8.02(0.4H, brs), 7.90(0.6H, brs), 7.23–7.36(5H, m), 6.75–7.18(4H, m), 5.70(0.7H, s), 5.62(0.3H, s), 3.91–4.09(1H, m), 3.57–3.75(2H, m), 2.54–3.09(5H, m), 1.62–2.03(3H, m).

PREPARATION EXAMPLE 21

Synthesis of 3-(1-ethylpiperidin-2-yl)methyl-4-phenyl-3,4-dihydro-2(1H)-quinazolinone In similar way as in Preparation Example 20, the title compound, as an about 1:1 mixture of the diastereomers, was synthesized from 4-phenyl-3-(piperidin-2-yl)methyl-3,4-dihydro-2(1H)-quinazolinone and ethyl iodide.

¹H NMR(CDCl₃) δ; 8.05(1H, brs), 7.24–7.36(5H, m), 6.74–7.16(4H, m), 5.48(1H, m), 4.16(1H, m), 2.35–2.96 (8H, m), 1.30–1.77(4H, m), 0.99(3H, t, J=7 Hz).

PREPARATION EXAMPLE 22

Synthesis of 3-(4-ethylmorpholin-2-yl)methyl-4-phenyl-3,4-dihydro-2(1H)-quinazolinone In similar way as in Preparation Example 20, the title compound, as an about 2:3 mixture of the diastereomers, was synthesized from 3-(morpholin-2-yl)-methyl-4-phenyl-3,4-dihydro-2(1H)-quinazolinone and ethyl iodide.

¹H NMR (CDCl₃) δ: 7.08–7.38(6H, m), 6.99–7.06(1H, m), 6.83–6.92 (1H, m), 6.65–6.73(1H, m), 5.75(0.4H, s), 5.71(0.6H , s), 4.22(0.4H, dr, J=2, 11 Hz), 4.17(0.6H, dt , J=2, 11 Hz), 4.12(0.6H, dd, J=15, Hz), 3.94 (0.4H, dd, J=14, 4 Hz), 3.70–3.90(2H, m), 2.96(0.6H, dd, J=15, 3 Hz), 2.60–2.86(2.2H, m), 2.37(2H, q, J=7.2 Hz), 2.06(1.2H, J=12, 3 Hz), 1.94 (0.6H, dd, J=12, 11 Hz), 1.74(0.4H, dd, J=12, 11 Hz), 1.06(1.8H, t, J=7.2 Hz), 1.05(1.2H, t, J=7.2 Hz).

PREPARATION EXAMPLE 23

Synthesis of 3-(4-benzylmorpholin-2-yl)methyl-4-phenyl-3,4-dihydro-2(1H)-quinazolinone In similar way as in Preparation Example 20, the title compound, as an about 2:3 mixture of the diastereomers was synthesized from 3-(morpholin-2-yl)-methyl-4-phenyl-3,4-dihydro-2(1H)-quinazolinone and benzyl bromide.

$^1$H NMR(CDCl$_3$) δ; 7.64(0.6H, brs), 7.57(0.4H, brs), 7.17–7.43(9H, m), 7.12(0.6H, dt, J=8, 1 Hz), 7.11 (0.4H, dt, J=8, 1 Hz), 7.02(0.4H, s), 7.00(0.6H, s), 6.88(0.6H, dt, J=7, 1 Hz), 6.87(0.4H, dt, J=7, 1 Hz), 6.72(0.6H, dd, J=8, 1 Hz), 6.70(0.4H, dd, J=8, 1 Hz), 5.77(0.4H, s), 5.68(0.6H, s), 4.11(0.6H, dd, J=15, Hz), 3.70–3.95(2.4H, m), 3.30–3.67(3H, m), 2.95 (0.6H, dd, J=15, 4 Hz), 2.48–2.85(2.2H, m), 2.00–2.19 (1.6H, m), 1.83(0.6H, dd, J=11, 10 Hz).

PREPARATION EXAMPLE 24

Synthesis of 3-(1-benzylpiperidin-4-yl)-4-phenyl-3,4-dihydro-2(1H)-quinazolinone (a) Synthesis of N-(1-benzylpiperidin-4-yl)-2-(trichloroacetylamino)benzophenoneimine A 40.8 g (119 mmol) portion of 2-trichloroacetylaminobenzophenone obtained from 2-aminobenzophenone in similar way as in Preparation Example 1, and 25.0 g (131 mmol) of 4-amino-1-benzylpiperidine were dissolved in 300 mL of dimethylsulfoxide, and the solution was stirred at temperature of around 40 ° C. for 15 hours. The reaction mixture was poured into water, and the crystals formed were separated by filtration. The resulting crude crystals were recrystallized from ethyl acetate to give 44.8 g (86.9 mmol) of the title compound.

$^1$H NMR(CDCl$_3$) δ; 8.73(1H, m), 7.22–7.54(9H, m), 7.12–7.16(2H, m), 6.88–6.99(2H, m), 3.44(2H, s), 3.06–3.17(1H, m), 2.82–2.86(2H, m), 1.96–2.11 (2H, m), 1.72–1.82(2H, m), 1.50–1.58(2H, m).

Melting point: 151°–152° C. (recrystallized from ethyl acetate)

(b) Synthesis of α-(2-aminophenyl)-N-(1-benzylpiperidin-4-yl)benzylamine

To a solution of 44.7 g (86.8 mmol) of N-(1-benzylpiperidin-4-yl)-2-(trichloroacetylamino)benzo-phenoneimine in 150 mL of ethanol was added 3.28 g (86.8 mmol) of sodium borohydride at temperature of 5° C. to 15° C., and the mixture was stirred for 2 hours. Additionally, 3.28 g (86.8 mmol) of sodium borohydride was added to the mixture at temperature of 5° C. to 15° C., and the mixture was stirred for 10 hours at ambient temperature. The reaction mixture was diluted with water, and the ethanol was distilled off in vacuo. The residual mixture was extracted with ethyl acetate, and the organic layer separated was washed with brine, dried on sodium sulfate and concentrated in vacuo. The residue was purified by means of column chromatography (silica gel, ethyl acetate) to give 27.7 g (74.5 mmol) of the title compound.

$^1$H NMR(CDCl$_3$) δ; 7.21–7.35(10H, m), 7.01–7.07(1H, m), 6.84–6.88(1H, m), 6.60–6.65(2H, m), 5.08(1H, s), 4.74(1H, br), 3.46(2H, s), 2.79(2H, brd, J=11 Hz), 2.44–2.52(1H, m), 1.86–2.00(4H, m), 1.65 (2H, brs), 1.46–1.60(2H, m).

(c) synthesis of 3-(1-benzylpiperidin-4-yl)-4-phenyl-3,4-dihydro-2(1H)-quinazolinone To a solution of 27.6 g (74.4 mmol) of α-(2-aminophenyl)-N-(1-benzylpiperidin-4-yl)benzylamine in 300 mL of tetrahydrofuran was added 12.1 g (74.5 mmol) of 1,1'-carbonyldiimidazole, and the mixture was heated under reflux for 8 hours. After allowing to cool, the reaction mixture was concentrated in vacuo. The residue was purified by means of column chromatography (silica gel, 1:9 methanol:chloroform). The resulting crude crystals were recrystallized from ethanol to give 24.0 g (60.3 mmol) of the title compound.

$^1$H NMR(CDCl$_3$) δ; 7.11–7.40(12H, m), 6.91(1H, dd, J=7.6, 1.0 Hz), 6.83(1H, s), 6.66(1H, d, J=7.6 Hz), 5.56(1H, s), 4.33–4.45(1H, m), 3.45(1H, m), 2.90–2.97(1H, m), 2.74–2.81(1H, m), 1.91–2.14(2H, m), 1.42–1.65(2H, m).

Melting point: 199°–200° C. (recrystallized from ethanol)

Melting point of the citrate: 159°–161.5° C. (recrystallized from diethyl ether/ethanol)

PREPARATION EXAMPLE 25

Synthesis of 3-(quinuclidin-3-yl)-4-phenyl-3,4-dihydro-2(1H)-quinazolinone

In similar way as in Preparation Example 24, the title compound, as a mixture of the diastereomers, was synthesized from 2-aminobenzophenone and 3-aminoquinuclidine. The mixed diastereomers were separated each other by means of column chromatography (silica gel, 1:9:90 aqueous ammonia:methanol:chloroform) to give 258 mg of Diastereomer A, 330 mg of Diastereomer B and 480 mg of the mixture. Diastereomer A had a higher Rf value, and Diastereomer B, a lower Rf value, on thin layer chromatography (developed with 1:9:90 aqueous ammonia: methanol:chloroform).

Diastereomer A:

$^1$H NMR(CDCl$_3$) δ; 8.41(1H, brs), 7.12–7.36(8H, m), 6.96(1H, m), 6.77(1H, m), 5.75 (1H, s ), 4.62 (1H, m ), 2.77–3.05(5H, m), 2.50(1H, m), 1.36–1.98(5H, m).

Melting Point of the HCl salt: over 250 ° C. (recrystallized from diethyl ether/ethanol)

Diastereomer B:

$^1$H NMR(CDCl$_3$) δ; 8.59(1H, m), 6.76–7.30(9H, m), 5.59(1H, s), 3.87(1H, m), 3.67(1H, m), 2.72–3.04(5H, m), 1.40–2.06(5H, m).

PREPARATION EXAMPLE 26

Synthesis of 3-(1-methylpiperidin-4-yl)-4-phenyl-3,4-dihydro-2(1H)-quinazolinone In similar way as in Preparation Example 24, the title compound was synthesized from 2-aminobenzo-phenone and 4-amino-1-methylpiperidine.

$^1$H NMR(CDCl$_3$) δ; 7.54(1H, brs), 7.08–7.43(7H, m), 6.90(1H, m), 6.72(1H, m), 5.55(1H, s), 4.40(1H, m), 2.91(1H, m), 2.73(1H, m), 3.23(3H, s), 1.93–2.12 (3H, m), 1.46–1.69(3H, m).

Melting point: 252°–253° C. (recrystallized from ethanol)

PREPARATION EXAMPLE 27

Synthesis of 3-(1-benzylpyrrolidin-3-yl)-4-phenyl-3,4-dihydro-2(1H)-quinazolinone In similar way as in Preparation Example 24, the title compound, as a mixture of the diastereomers, was synthesized from 2-aminobenzophenone and 3-amino-1-benzylpyrrolidin. The mixed diastereomers were separated from each other by means of column chromatography (silica gel, 1:2 ethyl acetate:chloroform) to give 520 mg (1.36 mmol) of Diastereomer A and 1.08 g (2.82 mmol) of a mixture of Diastereomers A and B. Diastereomer A had a higher Rf value, and Diastereomer B, a lower Rf value, on thin layer chromatography (developed with 1:2 ethyl acetate:chloroform).

Diastereomer A:

¹H NMR(CDCl₃) δ; 7.50(1H, m), 7.08–7.35(12H, m), 6.69–6.93(2H, m), 5.77(1H, s), 4.83(1H, m), 3.57 (1H, d, J=13 Hz), 3.40(1H, d, J=13 Hz), 2.90(1H, m), 2.68(1H, m), 2.20–2.34(3H, m), 2.16(1H, m).

Melting point: around 250° C. (decomposed, recrystallized from diethyl ether/ethanol)

PREPARATION EXAMPLE 28

Synthesis of 3-(pyrrolidin-3-yl)-4-phenyl-3,4-dihydro-2(1H)-quinazolinone

In similar way as in Preparation Example 15, the title compound, as a mixture of the diastereomers, was synthesized from the mixed diastereomers of 3-(1-benzyl-pyrrolidin-3-yl)-4-phenyl-3,4-dihydro-2(1H)-quinazolinone.

¹H NMR(CD₃OD) δ; 7.29–7.41(5H, m), 6.79–7.15(4H, m), 5.67(1H, m), 4.20(1H, m), 3.62(1H, m), 2.88–3.18 (3H, m), 2.14–2.53(2H, m).

Melting point: over 250° C. (recrystallized from ethanol)

PREPARATION EXAMPLE 29

Synthesis of 3-(1-ethylpyrrolidin-3-yl)-4-phenyl-3,4-dihydro-2(1H)-quinazolin

In similar way as in Preparation Example 20, the title compound, as an about 1:2 mixture of the diastereomers, was synthesized from 3-(pyrrolidin-3-yl)-4-phenyl-3,4-dihydro-2(1H)-quinazolinone and ethyl iodide.

¹H NMR(CDCl₃) δ; 7.52–7.58(1H, m), 7.08–7.41(7H, m), 6.90(1H, m), 6.73(1H, m), 5.76(0.7H, s), 5.72(0.3H, s), 4.72–4.91(1H, m), 1.70–2.88(9H, m), 1.07(0.9H, t, J=7 Hz), 0.97(2.1H, t, J=7 Hz).

PREPARATION EXAMPLE 30

Synthesis of 3-(piperidin-4-yl)-4-phenyl-3,4-dihydro-2(1H)-quinazolinone

In similar way as in Preparation Example 15, the title compound was synthesized from 3-(1-benzyl-piperidin-4-yl)-4-phenyl-3,4-dihydro-2(1H)-quinazolinone.

¹H NMR(CDCl₃) δ: 7.37–7.41(2H, m), 7.09–7.31(5H, m), 6.90(1H, dt, J=1, 7 Hz), 6.71(1H, d, J=8 Hz), 5.56 (1, s), 4.36 (1HH, m), 3.13 (1H, m), 2.99(1H, m), 2.55–2.73(2H, m), 1.87–2.02(1H, m), 1.56–1.76(2H, m), 1.29–1.45(1H, m).

Melting point: 213°–215° C. (recrystallized from diethyl ether/ethanol)

Melting point of the HCl salt: over 250° C. (recrystallized from ethanol)

PREPARATION EXAMPLE 31

Synthesis of 3-(1-allylpiperidin-4-yl)-4-phenyl-3,4-dihydro-2(1H)-quinazolinone

To a solution of 300 mg (0.976 mmol) of 3-(1-piperidine-4-yl)-4-phenyl-3,4-dihydro-2(1H)-quinazolinone in 20 mL of ethanol were added, sequentially, 202 mg (1.46 mmol) of potassium carbonate and 142 mg (1.17 mmol) of allyl bromide, and the mixture was stirred for 4 hours at ambient temperature. The reaction mixture was concentrated in vacuo, and the residue was partitioned between water and chloroform. The organic layer separated was dried on potassium carbonate and then concentrated in vacuo. The residue was purified by means of column chromatography (silica gel, 1:9:90 aqueous ammonia:methanol:chloroform) to give 262 mg (0.67 mmol) of the title compound.

¹H NMR(CDCl₃) δ; 7.06–7.45(7H, m), 6.90(1H, brt, J=7.8 Hz), 6.69(1H, brd, J=8 Hz), 5.73–5.92(1H, m), 5.58(1H, s), 5.05–5.22(2H, m), 5.33–5.52(1H, m), 2.78–3.10(4H, m), 1.87–2.24(3H, m), 1.36–1.80(3H, m).

Melting point of the HCl salt: 190°–195° C. (recrystallized from ethanol)

PREPARATION EXAMPLE 32

Synthesis of 3-[1-(2-propynyl)piperidine-4-yl]-4-phenyl-3,4-dihydro-2(1H)-quinazolinone In similar way as in Preparation Example 31, the title compound was synthesized from 3-(piperidin-4-yl)-phenyl-3,4-dihydro-2(1H)-quinazolinone and propargyl bromide.

¹H NMR(CDCl₃) δ; 6.85–7.52(6H, m), 6.68(1H, brd, J=8 Hz), 5.55(1H, s), 4.32–4.50(1H, m), 3.25(2H, d, J=2 Hz), 2.71–3.40(2H, m), 1.95–2.43(3H, m), 2.21 (1H, t, J=2 Hz), 1.40–1.90(3H, m).

Melting point: 198°–201° C. (recrystallized from diethyl ether/ethanol)

PREPARATION EXAMPLE 33

Synthesis of 3-(1-ethylpiperidin-4-yl)-4-phenyl-3,4-dihydro-2(1H)-quinazolinone

In similar way as in Preparation Example 31, the title compound was synthesized from 3-(piperidin-4-yl)-4-phenyl-3,4-dihydro-2(1H)-quinazolinone and ethyl iodide.

The HCl salt:

¹H NMR(DMSO-d₆) δ; 9.58–9.76(1H, brs), 9.54(1H, s), 7.18–7.45(6H, m), 7.09(1H, dd, J=8, 1.5 Hz), 6.77–6.89(2H, m), 5.64(1H, s), 4.13–4.30(1H, m), 3.21–3.50(2H, m), 2.72–3.09(4H, m), 2.30–2.59 (1H, m), 1.75–1.99(1H, m), 1.50–1.72(2H, m), 1.16 (3H, t, J=7 Hz).

Melting point: 295°–296° C. (decomposed, recrystallized from diethyl ether/ethanol)

PREPARATION EXAMPLE 34

Synthesis of 3-[1-(2-hydroxyethyl)piperidin-4-yl]-4-phenyl-3,4-dihydro-2(1H)-quinazolinone In similar way as in Preparation Example 31, the title compound was synthesized from 3-(piperidin-4-yl)-4-phenyl-3,4-dihydro-2(1H)-quinazolinone and ethylene bromohydrin.

¹H NMR(CDCl₃) δ; 7.04–7.50(7H, m), 6.90(1H, dt, J=1, 7.6 Hz), 6.69(1H, d, J=8 Hz), 5.53(1H, s), 4.27–4.45 (1H, m), 3.76–3.89(1H, m), 3.55(2H, m), 2.91–3.05 (2H, m), 2.49(2H, m), 1.93–2.28(3H, m), 1.35–1.72 (3H, m).

Melting point of the HCl salt: 261°–265° C. (recrystallized from diethyl ether/ethanol)

PREPARATION EXAMPLE 35

Synthesis of 3-(1-ethoxycarbonylmethylpiperidin-4-yl)-4-phenyl-3,4-dihydro-2(1H)-quinazolinone To a solution of 1.5 g (4.88 mmol) of 3-(piperidin-4-yl)-4-phenyl-3,4-dihydro-2(1H)-quinazolinone in 30 mL of isopropanol were added 896 mg (5.37 mmol) of ethyl bromoacetate, 853 mg (96.18 mmol) of potassium carbonate and 20 mg of potassium iodide, and the mixture was heated under reflux for 3 hours. The hot solution was subjected to filtration, and the solid matter was washed with 200 mL of hot isopropanol. The filtrate was concentrated in vacuo, and the residue was purified by means of column chromatography (silica gel, 1:9 :90 aqueous ammonia:methanol:chloroform) to give 1.88 g (4.37 mmol) of the title compound.

¹H NMR(CDCl₃) δ; 7.71–7.83(1H, brs), 7.05–7.43 (1H, m), 6.90(1H, dt, J=1, 7 Hz), 6.73(1H, d, J=8 Hz), 5.57(1H, s), 4.36–4.54(1H, m), 4.17(2H, g, J=7 Hz), 3.16(2H , s), 2.95–3.07(1H, m), 2.79–2.90 (1H, m), 2.00–2.39(3H, m), 1.45–1.82(2H, m), 1.25(3H, t, J=7 Hz), 1.17–1.30(1H, m).

Melting point of the HCl salt: 195°–198° C. (recrystallized from diethyl ether/ethanol)

PREPARATION EXAMPLE 36

Synthesis of 3-[1-(2-furylmethyl)piperidin-4-yl]-4 -phenyl-3,4-dihydro-2(1H)-quinazolinone To a solution of 344 mg (1.0 mmol) of 3-(piperidin-4-yl)-4-phenyl-3,4-dihydro-2(1H)-quinazolinone HCl salt and 384 mg (4.0 mmol) of furfural in 40 mL of methanol was added 123 mg (2.0 mmol) of sodium cyano-borohydride under ice-cooling. After being stirred for 12 hours at ambient temperature, the reaction mixture was concentrated in vacuo. The residue was diluted with water, and the mixture was adjusted to pH 10 with aqueous ammonia, and then extracted with chloroform. The organic layer separated was dried on potassium carbonate and then concentrated in vacuo. The residue was purified by means of column chromatography (silica gel, 1:9 methanol:chloroform) to give 329 mg (0.85 mmol) of the title compound.

¹H NMR(CDCl₃) δ; 7.31–7.37(3H, m), 7.08–7.28(5H, m), 6.88–6.94(1H, m), 6.60–6.73(2H, m), 6.29(1H, dd, J=3, 2 Hz), 6.16(1H, d, J=3 Hz), 5.56(1H, s), 4.42(1H, m), 3.49(2H, s), 2.95(1H, d, J=10 Hz), 2.79(1H, d, J=12 Hz), 1.96–2.17(3H, m), 1.45–1.69 (3H, m).

Melting point of the HCl salt: 205°–206° C. (recrystallized from diethyl ether/ethanol)

In similar way as in Preparation Example 36, the compounds of Preparation Examples 37 through 69 were synthesized.

PREPARATION EXAMPLE 37

3-[1-(3-furylmethyl)piperidin-4-yl]-4-phenyl-3,4 -dihydro-2(1H)-quinazolinone

¹H NMR(CDCl₃) δ; 7.35–7.39(3H, m), 7.08–7.29(7H, m), 6.87–6.93(1H, m), 6.68(1H, d, J=8 Hz), 6.34(1H, d, J=1.6 Hz), 5.56(1H, s), 4.34–4.43(1H, m), 3.33 (2H, s), 2.96(1H, d, J=8 Hz), 2.81(1H, d, J=11 Hz), 1.91–2.12 (3H, m), 1.41–1.65(3H, m).

Melting point: over 250° C. (recrystallized from ethanol)

PREPARATION EXAMPLE 38

3-[1-(2-thienylmethyl)piperidin-4-yl]-4-phenyl-3,4 -dihydro-2(1H)-quinazolinone

¹H NMR(CDCl₃) δ; 7.61(1H, s), 7.38(2H, m), 7.08–7.29 (6H, m), 6.86–6.93(3H, m), 6.72(1H, d, J=8 Hz), 5.56(1H, s), 4.33–4.45(1H, m), 3.68(2H, s), 2.98(1H, d, J=10 Hz), 2.83(1H, dd, J=11, 2.3 Hz), 1.95–2.18(3H, m), 1.39–1.67(3H, m).

Melting point of the HCl salt: 213°–214.5° C. (recrystallized from diethyl ether/ethanol)

PREPARATION EXAMPLE 39

3-[1-(3-thienylmethyl)piperidin-4-yl]-4-phenyl-3,4 -dihydro-2(1H)-quinazolinone

¹H NMR(CDCl₃) δ; 7.66(1H, s), 7.35–7.40(2H, m), 7.07–7.29(7H, m), 7.02(1H, m), 6.86–6.92(1H, m), 6.72(1H, d, J=8 Hz), 5.56(1H, s), 4.34–4.42(1H, m), 3.49(2H, s), 2.95(1H, brd, J=7 Hz), 2.08(1H, brd, J=11 Hz), 1.93–2.17(3H, m), 1.47–1.65(3H, m).

Melting point of the HCl salt: 240°–242° C. (recrystallized from ethanol)

PREPARATION EXAMPLE 40

3-[1-(2-pyridylmethyl)piperidin-4-yl]-4-phenyl-3,4 -dihydro-2(1H)-quinazolinone

¹H NMR (CDCl₃) δ; 8.55(1H, m), 7.69(1H, s), 7.59–7.65 (1H, m), 7.08–7.40(9H, m), 6.87–6.93(1H, m), 6.73(1H, d, J=8 Hz), 5.57(1H, s), 4.37–4.47(1H, m), 3.61 (2H, s), 2.96(1H, d, J=8.5 Hz), 2.80(1H, d, J=11 Hz) , 2.02–2.25(3H, m), 1.51–1.65(3H, m).

Melting point of the HCl salt: 253°–255° C. (recrystallized from ethanol)

PREPARATION EXAMPLE 41

3-[1-(3-pyridylmethyl)piperidin-4-yl]-4-phenyl-3,4 -dihydro-2(1H)-quinazolinone

¹H NMR(CDCl₃) δ; 8.47–8.51(2H, m), 7.53–7.63(2H, m), 7.37–7.41(2H, m), 7.08–7.30(6H, m), 6.87–6.93 (1H, m), 6.71(1H, d, J=8 Hz), 5.55 (1H, s), 4.32–4.44 (1H, m), 3.46(2H, s), 2.90(1H, brd, J=10 Hz), 2.76(1H, brd, J=11 Hz), 1.95–2.17(3H, m), 1.38–1.65 (3H, m).

Melting point of the HCl salt: 252°–254° C. (recrystallized from diethyl ether/ethanol)

PREPARATION EXAMPLE 42

3-[1-(4-pyridylmethyl)piperidin-4-yl]-4-phenyl-3,4 -dihydro-2(1H)-quinazolinone

¹H NMR(CDCl₃) δ; 8.52(2H, dd, J=4.6, 1.6 Hz), 7.37–7.41 (2H, m), 7.07–7.31(8H, m), 6.88–6.94(1H, m), 6.69(1H, d, J=8 Hz), 5.56(1H, s), 4.30–4.42(1H, m), 3.44(2H, s), 2.89(1H, dd, J=10, 2 Hz), 2.75(1H, brd, J=11 Hz), 1.97–2.17(3H, m), 1.45–1.64(3H, m).

Melting point: 241.5°–243° C. (recrystallized from ethanol)

PREPARATION EXAMPLE 43

3-[1-(2-imidazolylmethyl)piperidin-4-yl]-4-phenyl-3,4 -dihydro-2(1H)-quinazolinone ¹H NMR(CDCl₃) δ; 9.38(1H, s), 8.31(1H, s), 7.18–7.41 (6H, m), 7.03–7.17(1H, m), 6.76–6.87(2H, m), 5.69(1H, s), 4.09(1H, m), 3.41(2H, s), 2.83(1H, m), 2.65(1H, m), 1.97–2.00(3H, m), 1.37(3H, m).

Melting point of the HCl salt: 303°–305° C. (recrystallized from ethanol)

PREPARATION EXAMPLE 44

3-[1-(2-pyrrolylmethyl)piperidin-4-yl]-4-phenyl-3,4 -dihydro-2(1H)-quinazolinone ¹H NMR(CDCl₃) δ; 10.59(1H, brs), 9.38(1H, brs), 7.15–7.48(6H, m), 7.05(1H, m), 6.76–6.83(2H, m), 6.59(1H, m), 5.88(1H, m), 5.81(1H, brs), 5.70(1H, s), 4.06(1H, m), 3.33(2H, s), 2.82(1H, m), 2.62–2.71 (1H, m), 1.83–2.10(3H, m), 1.28–1.43(3H, m).

Melting point of the HCl salt: 201°–204° C. (recrystallized from ethanol)

PREPARATION EXAMPLE 45

3-[1-(1-methyl-2-pyrrolylmethyl)piperidin-4-yl]-4 -phenyl-3,4-dihydro-2(1H)-quinazolinone ¹H NMR(CDCl₃) δ; 7.08–7.58(7H, m), 6.90(2H, m), 6.72(2H, m), 5.54(1H, s), 4.33–4.57(2H, m), 3.46–3.73 (1H, m), 2.95(1H, m), 2.79(1H, m), 2.59(3H, s), 1.88–2.10(3H, m), 1.20–1.75(3H, m).

PREPARATION EXAMPLE 46

3-[1-(2-phenylethyl)piperidin-4-yl]-4-phenyl-3,4-dihydro-2(1H)-quinazolinone $^1$H NMR(CDCl$_3$) δ; 7.62(1H, s), 7.37–7.41(2H, m), 7.09–7.30(10H, m), 6.88–6.93(1H, m), 6.73(1H, d, J=7.6 Hz), 5.59(1H, s), 4.40–4.50(1H, m), 3.06(1H, d J=10 Hz), 2.93(1H, d, J=11 Hz), 2.73–2.79(2H, m), 2.53–2.58(2H, m), 1.97–2.20(3H, m), 1.43–1.72(3H, m).

Melting point of the HCl salt: 284°–285.5° C. (recrystallized from diethyl ether/ethanol)

PREPARATION EXAMPLE 47

3-[1-(cyclohexylmethyl)piperidin-4-yl]-4-phenyl-3,4-dihydro-2(1H)-quinazolinone $^1$H NMR(CDCl$_3$) δ; 7.67(1H, s), 7.36–7.41(2H, m), 7.08–7.29(5H, m), 6.87–6.93(1H, m), 6.72(1H, d, J=8 Hz), 5.57(1H, s), 4.34–4.44(1H, m), 2.90(1H, d, J=7 Hz), 2.77(1H, d, J=11 Hz), 1.62–2.12(11H, m), 1.35–1.51(3H, m), 1.05–1.25(3H, m), 0.75–0.88(2H, m).

Melting point of the HCl salt: 194°–197.5° C. (recrystallized from diethyl ether/ethanol)

PREPARATION EXAMPLE 48

3-[1-(4-cyclohexenylmethyl)piperidin-4-yl]-4-phenyl-3,4-dihydro-2(1H)-quinazolinone HCl salt:

$^1$H NMR(DMSO-d$_6$) δ; 9.53(1H, s), 9.35–9.53(1H, m), 7.18–7.45(6H, m), 7.09(1H, dt, J=1, 8 Hz), 6.76–6.89 (2H, m), 5.55–5.72(3H, m), 4.12–4.38(1H, m), 3.20–3.55(2H, m), 2.80–3.07(4H, m), 2.39–2.63(1H, m), 1.47–2.26(9H, m), 1.10–1.30(1H, m).

Melting point: 160° C. (decomposed, recrystallized from diethyl ether/ethanol)

PREPARATION EXAMPLE 49

3-(1-cyclohexylpiperidin-4-yl)-4-phenyl-3,4-dihydro-(1H)-quinazolinone $^1$H NMR(CDCl$_3$) δ; 7.39(2H, d, J=7 Hz), 7.05–7.29(5H, m), 6.88–6.94(1H, m), 6.67(1H, d, J=8 Hz), 5.61(1H, s), 4.45(1H, m), 3.02(1H, d, J=10 Hz), 2.87(1H, d, J=11 Hz), 1.50–2.46(12H, m), 1.04–1.20(5H, m).

Melting point: 213°–215.5° C. (recrystallized from ethanol)

PREPARATION EXAMPLE 50

3-[1-(tetrahydropyran-4-yl)piperidin-4-yl]-4-phenyl-3,4-dihydro-2(1H)-quinazolinone $^1$H NMR(CDCl$_3$) δ; 7.36–7.40(2H, m), 7.08–7.30 (5H, m), 6.88–6.94(1H, m), 6.68(1H, dd, J=8, 1 Hz), 5.58(1H, s), 4.35–4.47(1H, m), 3.97–4.02(2H, m), 3.36(1H, d, J=11 Hz), 3.32(1H, d, J=12 Hz), 3.01 (1H, brd, J=12 Hz), 2.87(1H, brd, J=11 Hz), 2.10–2.45 (3H, m), 1.89–2.04(1H, m), 1.37–1.72(7H, m).

Melting point: 282°–284° C. (recrystallized from ethanol)

PREPARATION EXAMPLE 51

3-[1-(1-phenylethyl)piperidin-4-yl]-4-phenyl-3,4-dihydro-2(1H)-quinazolinone

The compound was obtained as an about 1:1 mixture of the diastereomers.

$^1$H NMR(CDCl$_3$) δ; 8.53(1H, s), 7.06–7.49(10H, m), 6.75–6.90(4H, m), 5.56(0.5H, s), 5.55(0.5H, s), 4.34 (1H, m), 3.38(1H, m), 2.70–3.09(2H, m), 1.86–2.08 (4H, m), 1.43–1.67(2H, m), 1.34(1.5H, d, J=6 Hz), 1.32(1.5H, d, J=6 Hz).

Melting point of the HCl salt: 282°–285° C. (recrystallized from diethyl ether/ethanol)

PREPARATION EXAMPLE 52

3-[1-(2-methoxybenzyl)piperidin-4-yl]-4-phenyl-3,4-dihydro-2(1H)-quinazolinone $^1$H NMR (CDCl$_3$) δ; 7.08–7.39(8H, m), 6.81–6.94(4H, m), 6.65 (1H, d, J=8 Hz), 5.58(1H, s), 4.39(1H, m), 3.79(3H, s), 3.52(2H, s), 2.97(1H, m), 2.83(1H, m), 1.95–2.17(3H, m), 1.49–1.65(3H, m).

Melting point: 197°–198.5° C. (recrystallized from ethanol)

PREPARATION EXAMPLE 53

3-[1-(3-methoxybenzyl)piperidin-4-yl]-4-phenyl-3,4-dihydro-2(1H)-quinazolinone $^1$H NMR(CDCl$_3$) δ; 7.37–7.40(2H, m), 7.08–7.29(6H, m), 6.76–6.94(5H, m), 6.66(1H, d, J=8 Hz), 5.56(1H, s), 4.38(1H, m), 3.80(3H, s), 3.43(2H, s), 2.93 (1H, m), 2.78(1H, m), 1.93–2.09(3H, m), 1.46–1.65 (3H, m).

Melting point: 187°–188.5° C. (recrystallized from ethanol)

Melting point of the meso-tartarate: 122°–140° C. (recrystallized from isopropanol)

PREPARATION EXAMPLE 54

3-[1-(4-methoxybenzyl)piperidin-4-yl]-4-phenyl-3,4-dihydro-2(1H)-quinazolinone $^1$H NMR(CDCl$_3$) δ; 7.35–7.39(2H, m), 7.08–7.29(6H, m), 6.77–6.93(4H, m), 6.65(1H, dd, J=8, 1 Hz), 5.56(1H, s), 4.37(1H, m), 3.79(3H, s), 3.39(2H, s), 2.92(1H, m), 2.77(1H, m), 1.90–2.10(3H, m), 1.46–1.64 (3H, m).

Melting point: 218°–219.5° C. (recrystallized from ethanol)

PREPARATION EXAMPLE 55

3-[1-(2-chlorobenzyl)piperidin-4-yl]-4-phenyl-3,4-dihydro-2(1H)-quinazolinone $^1$H NMR(CDCl$_3$) δ; 7.08–7.42(11H, m), 6.88–6.94(1H, m), 6.83(1H, brs), 6.66(1H, d, J=8 Hz), 5.57(1H, s), 4.33–4.45(1H, m), 3.56(2H, s), 2.95(1H, m), 2.81 (1H, m), 1.95–2.26(3H, m), 1.45–1.65(3H, m).

Melting point: 206°–207.5° C. (recrystallized from ethanol)

PREPARATION EXAMPLE 56

3-[1-(3-chlorobenzyl)piperidin-4-yl]-4-phenyl-3,4-dihydro-2(1H)-quinazolinone $^1$H NMR(CDCl$_3$) δ; 7.37–7.41(2H, m), 7.08–7.29(9H, m), 6.88–6.94(1H, m), 6.74(1H, brs), 6.65(1H, d, J=8 Hz), 5.56(1H, s), 4.33–4.43(1H, m), 3.41(2H, s), 2.88–2.92(1H, m), 2.72–2.77(1H, m), 1.94–2.13(3H, m), 1.46–1.65(3H, m).

Melting point: 204°–205.5° C. (recrystallized from ethanol)

PREPARATION EXAMPLE 57

3-[1-(4-chlorobenzyl)piperidin-4-yl]-4-phenyl-3,4-dihydro-2(1H)-quinazolinone

¹H NMR(CDCl₃) δ; 7.36–7.40(2H, m), 7.08–7.27(9H, m), 6.91(1H, m), 6.78(1H, brs), 6.66(1H, d, J=8 Hz), 5.55(1H, s), 3.42–4.42(1H, m), 3.40(2H, s), 2.88(1H, m), 2.74(1H, m), 1.92–2.12(3H, m), 1.38–1.64 (3H, m).

Melting point: 233°–234° C. (recrystallized from ethanol)

PREPARATION EXAMPLE 58

3-[1-(3-nitrobenzyl)piperidin-4-yl]-4-phenyl-3,4-dihydro-2(1H)-quinazolinone

¹H NMR(CDCl₃) δ; 8.19(1H, d, J=2 Hz), 8.08(1H, m), 7.61(1H, d, J=8 Hz), 7.39–7.48(3H, m), 7.09–7.31(5H, m), 6.88–6.94(1H, m), 6.68(1H, m), 5.57(1H, s), 4.34–4.45(1H, m), 3.53(2H, s), 2.89(1H, m), 2.75 (1H, m), 1.96–2.19(3H, m), 1.44(3H, m).

Melting point: 213°–214.5° C. (recrystallized from ethanol)

PREPARATION EXAMPLE 59

3-[1-(3-methylbenzyl)piperidin-4-yl]-4-phenyl-3,4-dihydro-2(1H)-quinazolinone

¹H NMR(CDCl₃) δ; 7.37(2H, m), 7.04–7.28(8H, m), 6.87–6.96(2H, m), 6.66(1H, d, J=8 Hz), 5.56(1H, s), 4.37(1H, m), 3.41(2H, s), 2.93(1H, m), 2.77(1H, m), 2.32(3H, s), 1.92–2.08(3H, m), 1.39–1.61(3H, m).

Melting point: 190°–191° C. (recrystallized from ethanol)

PREPARATION EXAMPLE 60

3-[1-(3-hydroxybenzyl)piperidin-4-yl]-4-phenyl-3,4-dihydro-2(1H)-quinazolinone
HCl salt:

¹H NMR(DMSO-d₆) δ; 9.37(1H, brs), 9.25(1H, brs), 7.39–7.43(2H, m), 7.26–7.31(3H, m), 7.15–7.21 (1H, m), 7.02–7.09(2H, m), 6.76–6.84(2H, m), 6.59–6.66 (3H, m), 5.76(1H, s), 4.12(1H, m), 3.29(2H, s), 2.82(1H, m), 2.69(1H, m), 1.86–2.04(3H, m), 1.35–1.43(3H, m).

Melting point: 222.5°–224° C. (recrystallized from ethanol)

PREPARATION EXAMPLE 61

3-[1-(3-cyanobenzyl)piperidin-4-yl]-4-phenyl-3,4-dihydro-2(1H)-quinazolinone

¹H NMR(CDCl₃) δ; 7.96(1H, s), 7.63(1H, s), 7.48–7.54 (2H, m), 7.35–7.43(3H, m), 7.09–7.30(5H, m), 6.87–6.93(1H, m), 6.75(1H, d, J=8 Hz), 5.57(1H, s), 4.35–4.45(1H, m), 3.46(2H, s), 2.87(1H, m), 2.73 (1H, m), 1.96–2.17(3H, m), 1.41–1.65(3H, m).

Melting point of the HCl salt: 226°–227.5° C. (recrystallized from diethyl ether/ethanol)

PREPARATION EXAMPLE 62

3-[1-(3-ethylbenzyl)piperidin-4-yl]-4-phenyl-3,4-dihydro-2(1H)-quinazolinone

¹H NMR(CDCl₃) δ; 7.36–7.39(2H, m), 7.06–7.29(9H, m), 6.88–6.94(1H, m), 6.75(1H, s), 6.65(1H, d, J=8 Hz), 5.57(1H, s), 4.40(1H, m), 3.49(2H, s), 2.94(1H, m), 2.78(1H, m), 2.62(2H, q, J=7.6 Hz), 1.93–2.08(3H, m), 1.42–1.64(3H, m), 1.22(3H, t, J=7.6 Hz).

Melting point of the HCl salt: 175°–179° C. (recrystallized from diethyl ether/ethanol)

PREPARATION EXAMPLE 63

3-[1-(3-methylthiobenzyl)piperidin-4-yl]-4-phenyl-3,4-dihydro-2(2H)-quinazolinone ¹H NMR(CDCl₃) δ; 7.39(2H, d, J=7 Hz), 7.02–7.28(9H, m), 6.87–6.92(1H, m), 6.69–6.90(1H, m), 5.56(1H, s), 4.39(1H, m), 3.42(2H, s), 2.91(1H, m), 2.78(1H, m), 2.47(3H, s), 1.95–2.03(3H, m), 1.51–1.64(3H, m).

Melting point: 188°–189° C. (recrystallized from diethyl ether/ethanol)

PREPARATION EXAMPLE 64

3-[1-(3-hydroxymethylbenzyl)piperidin-4-yl]-4-phenyl-3,4-dihydro-2(1H)-quinazolinone ¹H NMR(CDCl₃) δ; 7.08–7.40(11H, m), 6.91(1H, m), 6.81(1H, s), 6.65(1H, d, J=7 Hz), 5.56(1H, s), 4.68(2H, s), 4.38(1H, m), 3.45(2H, s), 2.92(1H, m), 2.77(1H, m), 1.93–2.09(3H, m), 1.46–1.68(3H, m).

Melting point of the HCl salt: 174°–177° C. (recrystallized from diethyl ether/ethanol)

PREPARATION EXAMPLE 65

3-[1-(3-fluorobenzyl)piperidin-4-yl]-4-phenyl-3,4-dihydro-2(1H)-quinazolinone

¹H NMR(CDCl₃) δ; 7.58(1H, brs), 7.38–7.41(2H, m), 7.01–7.30(8H, m), 6.87–6.95(2H, m), 6.72(1H, d, J=8 Hz), 5.56(1H, s), 4.40(1H, m), 3.44(2H, s), 2.91(1H, d, J=8 Hz), 2.77(1H, m), 1.95–2.14(3H, m), 1.43–1.65(3H, m).

Melting point: 202°–203° C. (recrystallized from ethanol)

PREPARATION EXAMPLE 66

3-[1-(3,4-methylenedioxybenzyl)piperidin-4-yl]-4-phenyl-3,4-dihydro-2(1H)-quinazolinone ¹H NMR(CDCl₃) δ; 7.36–7.40(2H, m), 7.08–7.29(4H, m), 6.87–6.93 (2H, m), 6.80 (1H, s), 6.65–6.73 (3H, m), 5.93(2H, s), 5.56(1H, s), 4.38(1H, m), 3.35(2H, s), 2.91(1H, m), 2.78(1H, m), 1.91–2.06 (3H, m), 1.39–1.64(3H, m).

Melting point: 209°–210° C. (recrystallized from ethanol)

PREPARATION EXAMPLE 67

3-[1-(3-ethoxybenzyl)piperidin-4-yl]-4-phenyl-3,4-dihydro-2(1H)-quinazolinone

¹H NMR(CDCl₃) δ; 8.15(1H, brs), 7.37–7.41(2H, m), 7.07–7.28(6H, m), 6.73–6.92(5H, m), 5.56(1H, s), 4.40(1H, m), 4.01(2H, q, J=7 Hz), 3.42(2H, s), 2.93 (1H, m), 2.79(1H, m), 1.94–2.09(3H, m), 1.48–1.63 (3H, m), 1.40(3H, t, J=7 Hz).

Melting point of the HCl salt: 170°–173° C. (recrystallized from ethanol)

PREPARATION EXAMPLE 68

3-[1-(3-isopropoxybenzyl)piperidin-4-yl]-4-phenyl-3,4-dihydro-2(1H)-quinazolinone ¹H NMR (CDCl₃) δ: 7.37–7.40(2H, m), 7.08–7.29(6H, m), 6.64–6.94(6H, m), 5.56(1H, s), 4.54(1H,m), 4.38(1H, m), 3.41(2H, s), 2.93(1H, m), 2.74(1H, m), 1.94–2.12 (3H, m), 1.49–1.64(3H, m), 1.33(3H, d, J=6.3 Hz), 1.32(3H, d, J=6.3 Hz)

Melting point of the HCl salt: 204°–206° C. (recrystallized from ethanol)

PREPARATION EXAMPLE 69

3-[1-(2-methoxyethyl)piperidin-4-yl]-4-phenyl-3,4-dihydro-2(1H)-quinazolinone

¹H NMR(CDCl₃) δ; 7.53(1H, brs), 7.36–7.39(2H, m), 7.08–7.29(5H, m), 6.90(1H, m), 5.57 (1H, s), 4.39–4.50(1H, m), 3.40–3.55(4H, m), 3.32(3H, s), 3.00–3.06(1H, m), 2.85–2.90(1H, m), 2.53(2H, m), 1.95–2.17(3H, m).

Melting point of the HCl salt: 102°–104° C. (recrystallized from acetone)

PREPARATION EXAMPLE 70

Synthesis of 3-[1-(3-aminobenzyl)piperidin-4-yl]-4-phenyl-3,4-dihydro-2(1H)-quinazolinone To a solution of 540 mg (1.22 mmol) of 3-[1-(3-nitrobenzyl)piperidin-4-yl]-4-phenyl-3,4-dihydro-2(1H)quinazolinone in 50 mL of ethanol was added 826 mg (3.66 mmol) of $SnCl_2 \cdot 2H_2O$, and the mixture was stirred for 12 hours at 60° C. After being cooled, the reaction mixture was filtered through cerite, and the filtrate was concentrated in vacuo. The residue was purified by means of column chromatography (silica gel, 1:19 methanol:chloroform) to give 210 mg (0.51 mmol) of the title compound.

$^1$H NMR(CDCl$_3$) δ: 7.36–7.40(2H, m), 7.04–7.29(6H, m), 6.88–6.94(2H, m), 6.63–6.67(2H, m), 6.54–6.58 (1H, m), 5.56(1H, s), 4.40(1H, m), 3.62(2H, br), 3.37(2H, s), 2.95(1H, m), 2.81(1H, m), 1.95–2.13 (3H, m), 1.50–1.63(3H, m).

Melting point of the HCl salt: 247°–249° C. (recrystallized from diethyl ether/ethanol)

PREPARATION EXAMPLE 71

Synthesis of 3-[1-(3-methanesulfonamidobenzyl) -piperidin-4-yl]-4-phenyl-3,4-dihydro-2(1H)-quinazolinone To a solution of 200 mg (0.48 mmol) of 3-[1-(3-aminobenzyl)piperidin-4-yl]-4-phenyl-3,4-dihydro-2(1H)quinazolinone in 20 mL of acetonitrile was added 93 mg (0.53 mmol) of methanesulfonic anhydride, and the mixture was stirred for 10 hours at ambient temperature. The reaction mixture was concentrated in vacuo, and the residue was purified by means of column chromatography (silica gel, 1:9 methanol:chloroform) to give 180 mg (0.37 mmol) of the title compound.

$^1$H NMR(CDCl$_3$) δ; 7.57(1H, s), 7.08–7.38(11H, m), 6.86–6.92(1H, m), 6.72(1H, dd, J=8, 1 Hz), 5.53(1H, s), 4.31(1H, m), 3.47(1H, d, J=13 Hz), 3.40(1H, d, J=13 Hz), 3.03(3H, s), 2.93(1H, m), 2.82(1H, m), 1.98–2.08(3H, m), 1.46–1.57(3H, m).

Melting point of the HCl salt: 219.5°–222.5° C. (recrystallized from diethyl ether/ethanol)

PREPARATION EXAMPLE 72

Synthesis of 3-[1-(3-acetylaminobenzyl)piperidin-4-yl]-phenyl-3,4-dihydro-2(1H)-quinazolinone To a solution of 200 mg (0.48 mmol) of 3-[1-(3-aminobenzyl)piperidin-4-yl]-4-phenyl-3,4-dihydro-2(1H)quinazolinone in 20 mL of tetrahydrofuran were added 42 mg (0.53 mmol) of acetyl chloride and 1 mL of triethylamine, and the mixture was stirred for 10 hours at ambient temperature. The reaction mixture was poured into water, and the mixture was extracted with ethyl acetate. The organic layer separated was washed with brine, dried on sodium sulfate and then concentrated in vacuo. The residue was purified by means of column chromatography (silica gel, 1:9 methanol:chloroform) to give 170 mg (0.37 mmol) of the title compound.

$^1$H NMR(CDCl$_3$) δ; 7.45(1H, m), 7.36–7.40(3H, m), 6.87–7.29(10H, m), 6.66(1H, d, J=8 Hz), 5.55(1H, s), 4.31(1H, s), 3.43(2H, s), 2.91(1H, m), 2.78(1H, 2.17(3H, s), 1.93–2.11(3H, m), 1.45–1.61(3H, m).

Melting point of the HCl salt: 192°–195° C. (recrystallized from diethyl ether/ethanol)

PREPARATION EXAMPLE 73

Synthesis of 3-[1-(3-dimethylaminobenzyl)piperidin-4-yl]-4-phenyl-3,4-dihydro-2(1H)-quinazolinone To a solution of 200 mg (0.48 mmol) of 3-[1-(3-aminobenzyl)piperidin-4-yl]-4-phenyl-3,4-dihydro-2(1H)quinazolinone in 20 mL of methanol were added 415 mg (4.85 mmol) of formaldehyde and 243 mg (3.88 mmol) of sodium cyanoborohydride and the mixture was stirred for 12 hours at ambient temperature. Then, the reaction mixture was concentrated in vacuo. The residue was diluted with water, and the mixture was adjusted to pH 10 with aqueous ammonia and extracted with chloroform. The organic layer separated was dried on potassium carbonate, and then concentrated in vacuo. The residue was purified by means of column chromatography (silica gel, 1:9:90 aqueous ammonia:methanol:chloroform) to give 210 mg (0.47 mmol) of the title compound.

$^1$H NMR(CDCl$_3$) δ; 7.37–7.40(2H, m), 7.07–7.29(7H, m), 6.87–6.93(3H, m), 6.60–6.69(4H, m), 5.57(1H, s), 4.39(1H, m), 3.42(2H, s), 2.90(1H, m), 2.93(6H, s), 2.80(1H, m), 1.94–2.13(3H, m), 1.43–1.60(3H, m).

Melting point of the oxalate: 264.5°–266° C. (recrystallized from ethanol)

PREPARATION EXAMPLE 74

Synthesis of 3- [ 1- (3-methoxycarbonylbenzyl)piperidin-4-yl]-4-phenyl-3,4-dihydro-2(1H)-quinazolinone (a) Synthesis of 3-[1-(3-benzyloxycarbonylbenzyl)-piperin-4-yl]-4-phenyl-3,4-dihydro-2(1H)quinazolinone In similar way as in Preparation Example 36, 1012 mg (1.90 mmol) of the title compound was obtained from 700 mg (2.03 mmol) of 3-(piperidin-4-yl)-4-phenyl-3,4-dihydro-2 (1H)-quinazolinone HCl salt and 3-benzyloxycarbonylbenzaldehyde.

$^1$H NMR(CDCl$_3$) δ; 7.93–7.96(2H, m), 7.08–7.50(14H, m), 6.87–6.93(1H, m), 6.67(1H, d, J=8 Hz), 5.55(1H, s), 5.36(2H, s), 4.39(1H, m), 3.48(2H, s), 2.90 (1H, m), 2.83(1H, m), 2.01–2.13(3H, m), 1.41–1.61 (3H, m).

(b) Synthesis of 3-[1-(3-methoxycarbonylbenzyl)-piperidin-4-yl]-4-phenyl-3,4-dihydro-2(1H)quinazolinone To a solution of 300 mg (0.56 mmol) of 3-[1-(3-benzyloxycarbonylbenzyl)piperidin-4-yl]-4-phenyl-3,4 -dihydro-2(1H)-quinazolinone in 20 mL of methanol was added 8 mg (0.06 mmol) of potassium carbonate and the mixture was stirred for 12 hours at ambient temperature. The reaction mixture was poured into water, and the mixture was extracted with ethyl acetate. The organic layer separated was washed with brine, dried on sodium sulfate and concentrated in vacuo. The residue was purified by means of column chromatography (silica gel, 1:9 methanol:chloroform) to give 179 mg (0.39 mmol) of the title compound.

$^1$H NMR(CDCl$_3$) δ; 7.89–7.94(3H, m), 7.08–7.50(8H, m), 6.88–6.93(1H, m), 6.77(1H, m), 5.56(1H, s), 4.40(1H, m), 3.91(3H, s), 3.49(2H, s), 2.92(1H, m), 2.78(1H, m), 2.01–2.12(3H, m), 1.52–1.65(3H, m).

Melting point of the HCl salt: 190°–191° C. (recrystallized from diethyl ether/ethanol)

PREPARATION EXAMPLE 75

Synthesis of 3-[1-(3-carboxybenzyl)piperidin-4-yl]-4-phenyl-3,4-dihydro-2(1H)-quinazolinone To a solution of 700 mg (1.32 mmol) of 3-[1-(3-benzyloxycarbonylbenzyl)piperidin-4-yl]-4-phenyl-3,4 -dihydro-2(1H)-quinazolinone in acetic acid was added 50 mg 10 % palladium-carbon, and the mixture was stirred for 5 hours in a hydrogen atmosphere at ambient temperature. The reaction mixture was filtered through cerite, and the filtrate was concentrated in vacuo. The resulting crude crystals were recrystallized from ethanol to give 450 mg (1.02 mmol) of the title compound.

$^1$H NMR(DMSO-d$_6$) δ; 9.37(1H, s), 7.79–7.83(2H, m), 7.15–7.50(8H, m), 7.02–7.08(1H, m), 6.75–6.84(2H, m), 5.80(1H, s), 4.15(1H, m), 3.46(2H, s), 2.68–2.84 (2H, m), 1.91–2.09(3H, m), 1.35–1.43(3H, m).

Melting point: over 250° C. (recrystallized from ethanol)

PREPARATION EXAMPLE 76

Synthesis of 3-[1-(3-carbamoylbenzyl)piperidin-4-yl]-4-phenyl-3,4-dihydro-2(1H)-quinazolinone To a solution of 220 mg (0.50 mmol) of 3-[1-(3-carboxybenzyl)piperidin-4-yl]-4-phenyl-3,4-dihydro-2(1H)quinazolinone in 50 mL of methylene chloride was added a solution of 65 mg (0.55 mmol) of thionyl chloride in 5 mL of methylene chloride, and the mixture was stirred for 1 hour at ambient temperature. The react ion mixture was bubbled with gaseous ammonia for 5 minutes, and then stirred for 1 hour at ambient temperature. The mixture was concentrated in vacuo, and the residue was dissolved in ethyl acetate. The solution was washed with water and then with brine, and dried on sodium sulfate. The solvent was distilled away in vacuo to give 210 mg (0.48 mmol) of the title compound.

$^1$H NMR(CDCl$_3$) δ; 7.77(1H, s), 7.66–7.70(1H, m), 7.09–7.46(10H, m), 6.88–6.94(1H, m), 6.69(1H, d, J=8 Hz), 6.15(1H, br), 5.80(1H, br), 5.56(1H, s), 4.33(1H, m), 3.49(2H, s), 2.90(1H, m), 2.77(1H, m), 1.96–2.14(3H, m), 1.52–1.62(3H, m)

Melting point of the HCl salt: 202°–205° C. (recrystallized from diethyl ether/ethanol)

PREPARATION EXAMPLE 77

Synthesis of 3-[1-(3-acetoxybenzyl)piperidin-4-yl]-4phenyl-3,4-dihydro-2(1H)-quinazolinone To a solution of 207 mg (0.5 mmol) of 3-[1-(3-hydroxybenzyl)piperidin-4-yl]-4-phenyl-3,4-dihydro-2(1H)quinazolinone in 3 mL of pyridine was added 61 mg (0.6 mmol) of acetic anhydride, and the mixture was stirred for 12 hours at ambient temperature. The reaction mixture was poured into water, and the mixture was extracted with ethyl acetate. The organic layer separated was washed with water and then with brine, dried on sodium sulfate and then concentrated in vacuo. The residue was purified by means of column chromatography (silica gel, 1:9 methanol:chloroform) to give 187 mg (0.41 mmol) of the title compound.

$^1$H NMR(CDCl$_3$) δ; 7.37–7.39(3H, m), 6.83–7.32(10H, m), 6.66 (1H, d, J=8 Hz), 5.55 (1H, s), 4.36 (1H, m), 3.44(2H, m), 2.88(1H, m), 2.78(1H, m), 2.29(3H, s), 1.90–2.08(3H, m), 1.41–1.58(3H, m).

Melting point of the HCl salt: 171°–173° C. (recrystallized from diethyl ether/ethanol)

PREPARATION EXAMPLE 78

Synthesis of 3-[1-(3-methylsulfinylbenzyl)piperidin-4yl]-4-phenyl-3,4-dihydro-2(1H)-quinazolinone To a solution of 480 mg (1 mmol) of 3-[1-(3-methylthiobenzyl)piperidin-4-yl]-4-phenyl-3,4-dihydro -2(1H)-quinazolinone HCl salt in 10 mL of methylene chloride was added 190 mg (1.1 mmol) of m-chloroperbenzoic acid at temperature of 0° C. to 10° C. The mixture was stirred for 10 hours at ambient temperature, mixed with water, adjusted to pH 10 with a aqueous ammonia and then extracted with chloroform. The organic layer separated was washed with brine, dried on sodium sulfate and then concentrated in vacuo. The residue was purified by means of column chromatography (silica gel, 1:9 methanol:chloroform) to give 440 mg (0.96 mmol) of the title compound as an about 1:1 mixture of the diastereomers.

$^1$H NMR(CDCl$_3$) δ; 8.41(1H, s), 7.61(1H, s), 7.39–7.50 (5H, m), 7.08–7.28(5H, m), 6.86–6.91(1H, m), 6.78(1H, d, J=8 Hz), 5.56(1H, s), 4.39(1H, m), 3.51 (2H, s), 2.88(1H, m), 2.73(1H, m), 2.71(1.5H, s), 2.72(1.5H, s), 2.03–2.12(3H, m), 1.51–1.64(3H, m).

Melting point of the HCl salt: 198°–202° C. (recrystallized from diethyl ether/ethanol)

PREPARATION EXAMPLE 79

Synthesis of 3-(1-carboxymethylpiperidin-4-yl)-4-phenyl-3,4-dihydro-2(1H)-quinazolinone A solution of 191 mg (0.445 mmol) of 3-(1-ethoxycarbonylmethylpiperidin-4-yl)-4-phenyl-3,4 -dihydro-2(1H)-quinazolinone HCl salt in 30 mL of 4N hydrochloric acid was heated under reflux for 4 hours. After being cooled, the reaction mixture was concentrated in vacuo. The residue was diluted with 30 mL of toluene, and the mixture was again concentrated in vacuo to give yellow crystals, which were then recrystallized from diethyl ether/ethanol to give 56 mg (0.14 mmol) of the HCl salt of the title compound.

The HCl salt:

$^1$H NMR(DMSO-d$_6$) δ; 9.83–10.13(1H, brs), 9.55 (1H, s), 7.18–7.48(6H, m), 7.03–7.15(1H, m), 6.75–6.90 (2H, m), 5.67(1H, s), 4.17–4.35(1H, m), 3.93–4.13(2H, brs), 2.87–3.90(5H, m), 1.49–1.99(3H, m).

Melting point: 230°–236° C. (recrystallized from diethyl ether/ethanol)

PREPARATION EXAMPLE 80

Synthesis of 3-(1-carbamoylmethylpiperidin-4-yl)-4-phenyl-3,4-dihydro-2(1H)-quinazolinone A solution of 200 mg (0.508 mmol) of 3-(1-ethoxycarbonylmethylpiperidin-4-yl)-4-phenyl-3,4-dihydro -2(1H)-quinazolinone in ammonia/methanol (6.09M, 30 mL) was stirred in an autoclave for 6 hours at temperature of approximately 150° C. After being cooled, the reaction mixture was concentrated in vacuo, and the residue was purified by means of column chromatography (silica gel, 1:9 methanol:chloroform) to give 167 mg (0.45 mmol) of the title compound.

The HCl salt:

$^1$H NMR(DMSO-d$_6$) δ; 9.40(1H, s), 6.95–7.50(7H, m), 6.73–6.90(2H, m), 5.74 (1H, s), 4.00–4.20 (1H, m), 2.60–2.90(2H, m), 2.78(2H, s), 1.92–2.18(3H, m), 1.20–1.55(3H, m).

Melting point: 208°–220° C. (recrystallized from diethyl ether/ethanol)

PREPARATION EXAMPLE 81

Synthesis of 3-[1-(3-methoxybenzyl)piperidin-4-yl]-4 -(3-hydroxyphenyl)-3,4-dihydro-2(1H)-quinazolinone a) Synthesis of 3-[1-(3-methoxybenzyl)piperidin-4-yl]-4-(3-benzyloxyphenyl)-3,4-dihydro-2(1H)-quinazolinone In similar way as in Preparation Example 24, the title compound was synthesized from 2-amino-3'-benzyloxybenzophenone and 4-amino-1-(3-methoxybenzyl)piperidine.

$^1$H NMR(CDCl$_3$) δ; 6.60–7.41(17H, m), 5.50(1H, s), 5.01(2H, s), 4.38(1H, m), 3.79(3H, s), 3.43(2H, s), 2.92(1H, m), 2.78(1H, m), 1.77–2.12(3H, m), 1.47–1.63 (3H, m).

(b) Synthesis of 3-[1-(3-methoxybenzyl)piperidin-4-yl]-4-(3-hydroxyphenyl)-3,4-dihydro-2(1H)-quinazolinone To a solution of 1.3 g (2.44 mmol) of 3-[1-(3-methoxybenzyl)piperidin-4-yl]-4-(3-benzyloxyphenyl)-3,4-dihydro-2(1H)-quinazolinone in 100 mL of methanol were added 504 mg (8 mmol) of ammonium formate and 50 mg of 10 palladium-carbon, and the mixture was heated under reflux for 8 hours. After being cooled, the reaction mixture was filtered through cerite, and the filtrate was concentrated in vacuo. The residue was dissolved in 50 mL of methanol, and 1.33 g (9.76 mmol) of m-anisaldehyde and 613 mg (9.76 mmol) of sodium cyanoborohydride were added to the solution. The mixture was stirred for 12 hours at ambient temperature. The reaction mixture was concentrated in vacuo, diluted with water, then adjusted to pH 10 with aqueous ammonia and extracted with chloroform. The organic layer separated was dried on potassium carbonate and concentrated in vacuo. The residue was purified by means of column chromatography (silica gel, 1:9 methanol:chloroform) to give 810 mg (1.83 mmol) of the title compound.

$^1$H NMR(DMSO-d$_6$) δ; 9.39(1H, s), 9.33(1H, s), 7.23–7.26 (2H, m), 7.03–7.08(2H, m), 6.75–6.86(7H, m), 6.55(1H, m), 5.65(1H, s), 4.09(1H, m), 3.72(3H, s), 3.36(2H, s), 2.83(1H, m), 2.71(1H, m)0 1.88–2.09(3H, m), 1.39(3H, br).

Melting point: over 250° C. (recrystallized from ethanol)
Melting point of the citrate: 130°–132° C. (recrystallized from diethyl ether/ethanol)

PREPARATION EXAMPLE 82

Synthesis of 3-(1-benzylpiperidin-4-yl)-6-chloro-4-phenyl-3,4-dihydro-2(1H)-quinazolinone In similar way as in Preparation Example 24, the title compound was synthesized from 5-chloro-2-trichloroacetylaminobenzophenone and 4-amino-1-benzylpiperidine.

$^1$H NMR(CDCl$_3$) δ; 7.19–7.38(10H, m), 7.13(1H, s), 7.11(1H, d, J=8.3 Hz), 6.62(1H, d, J=8.3 Hz), 5.50 (1H, s), 4.35(1H, m), 3.45(2H, s), 2.93(1H, d, J=0.6 Hz), 2.78(1H, d, J=11.6 Hz), 1.93–2.09(3H, m), 1.40–1.63(3H, m).

Melting point: over 230° C. (recrystallized from ethanol)
Melting point of the HCl salt: 162°–165° C. (recrystallized from diethyl ether/ethanol)

PREPARATION EXAMPLE 83

Synthesis of 3-[2-(diethylamino)ethyl]-6-nitro-4-phenyl-3,4-dihydro-2(1H)-quinazolinone In similar way as in Preparation Example 1, the title compound was synthesized from 5-nitro-2-trichloroacetylaminobenzophenone and 2-(diethylamino)ethylamine.

$^1$H NMR(CDCl$_3$) δ; 8.85(1H, brs), 8.04(1H, dd, J=8.9, 2.3 Hz), 7.90(1H, d, J=2.3 Hz), 7.34–7.38(5H, m), 6.85(1H, d, J=8.9 Hz), 5.85(1H, s), 3.80–3.90(5H, m), 2.96–3.07(1H, m), 2.68–2.78(1H, m), 2.44–2.60(5H, m), 0.99(6H, t, J=7.3 Hz).

Melting point: 161°–163° C. (recrystallized from ethanol)

PREPARATION EXAMPLE 84

Synthesis of 6-amino-3-[2-(diethylamino)ethyl]-4-phenyl-3,4-dihydro-2(1H)-quinazolinone In similar way as in Preparation Example 70, the title compound was synthesized from 3-[2-(diethylamino)ethyl]-6-nitro-4-phenyl-3,4-dihydro-2(1H)quinazolinone.

$^1$H NMR(CDCl$_3$) δ; 7.24–7.34(5H, m), 6.54(1H, d, J=8.3 Hz), 6.48(1H, dd, J=8.3, 2.3 Hz), 6.31(1H, d, J=2.3 Hz), 5.54(1H, s), 3.74–3.84(1H, m), 3.38(2H, brs), 2.95–3.05(1H, m), 2.65–2.75(1H, m), 2.36–2.58 (5H, m ), 0.99 (6H, t, J=7.3 Hz).

Melting point of the HCl salt: 242°–244° C. (recrystallized from diethyl ether/ethanol)

PREPARATION EXAMPLE 85

Synthesis of 3-[2-(diethylamino)ethyl]-4-phenyl-2-oxo-1,2,3,4-tetrahydropyrido[2,3-d]pyrimidine (a) Synthesis of 3-benzoyl-2-trichloroacetylamino-pyridine To a solution of 11.0 g (55 mmol) of 2-amino-3-benzoylpyridine and 6.1 g (60 mmol) of triethylamine in 200 mL of tetrahydrofuran was added dropwise 10.0 g (55 mmol) of trichloroacetyl chloride at temperature of 5° to 15° C. After being stirred for 3 hours at ambient temperature, the reaction mixture was poured into water, and then the mixture was extracted with ethyl acetate. The organic layer separated was washed with water and then with brine, dried on anhydrous sodium sulfate and then concentrated in vacuo. The resulting crude crystals were recrystallized from ethanol to give 14.0 g (40 mmol) of the title compound.

$^1$H NMR(CDCl$_3$) δ; 8.73–8.75(1H, m), 7.99–8.02 (1H, m), 7.71–7.77(2H, m), 7.62–7.68(1H, m), 7.42–7.56 (2H, m), 7.23–7.28(1H, m).

(b) Synthesis of 3-[2-(diethylamino) ethyl]-4-phenyl-4-trichloromethyl-2-oxo-l,2,3,4-tetrahydropyrido- [2,3-d]pyrimidine To a solution of 1.4 g (4.07 mmol) of 3-benzoyl-2-trichloroacetylaminopyridine in 50 mL of dimethylsulfoxide was added 0.52 g (4.5 mmol) of 2-(diethylamino)ethylamine, and the mixture was stirred for 24 hours at ambient temperature. The reaction mixture was poured into water, and then the mixture was extracted with ethyl acetate. The organic layer separated was washed with water and then with brine, dried on anhydrous sodium sulfate and then concentrated in vacuo. The residue was subjected to column chromatography (silica gel, 1:9 methanol:chloroform) for separation and purification to give 240 mg (0.54 mmol) of the title compound.

$^1$H NMR (CDCl$_3$) δ; 9.42(1H, brd), 8.33–8.38(2H, m), 7.31–7.46(3H, m), 7.13–7.19(2H, m), 6.83(1H, dd, J=7.9, 4.9 Hz), 3.89–4.00(1H, m), 3.15–3.26(1H, m), 2.75–2.85(1H, m), 2.20–2.34(4H, m), 1.92–2.02(1H, m), 0.79(6H, t, J=7.3 Hz).

(c) Synthesis of 3-[2-(diethylamino)ethyl]-4-phenyl-2-oxo-1,2,3,4-tetrahydropyrido[2,3-d]pyrimidine To a solution of 240 mg (0.54 mmol) of 3-[2(diethylamino)ethyl]-4-phenyl-4-trichloromethyl-2-oxo -1,2,3,4-tetrahydropyrido[2,3-d]pyrimidine in 10 mL of dimethylformamide was added 82 mg (1.26 mmol) of sodium borohydride at temperature of 5° C. to 15° C. After being stirred for 3 hours at ambient temperature, the reaction mixture was poured onto ice water, and the mixture was extracted with ethyl acetate. The organic layer separated was washed with water and then with brine, dried on anhydrous sodium sulfate and then concentrated in vacuo. The residue was purified by means of column chromatography (silica gel, 1:9 methanol:chloroform) to give 110 mg (0.34 mmol) of the title compound.

Melting point: 160°–162.5° C.

$^1$H NMR (CDCl$_3$) δ; 8.14(1H, dd, J=5.0, 1.7 Hz), 7.78 (1H, brs), 7.31–7.39(5H, m), 7.25–7.28(1H, m), 6.82 (1H, dd, J=7.6, 5.0 Hz), 5.75(1H, s), 3.77–3.87(1H, m), 2.99–3.03(1H, m), 2.69–2.79(1H, m), 2.42–2.60 (5H, m), 0.99(6H, t, J=7.3 Hz).

PREPARATION EXAMPLE 86

Synthesis of 3-[2-(diethylamino)ethyl]-4-phenyl-2-oxo-1,2,3,4-tetrahydropyrido[3,4-d]pyrimidine In similar way as in Preparation Example 85, the title compound was synthesized from 3-amino-4-benzoylpyridine and 2-(diethylamino)ethylamine.

Melting point: 138°–140.5° C. (recrystallized from ethyl acetate)

$^1$H NMR(CDCl$_3$) δ; 8.11(1H, s), 8.11(1H, d, J=5.0 Hz), 7.68(1H, brds), 7.30–7.36(5H, m), 6.86(1H, d, J=5.0 Hz), 5.76(1H, s), 3.77–3.87(1H, m), 2.97–3.08(1H, m), 2.66–2.78(1H, m), 2.41–2.59(5H, m), 0.99(6H, t, J=7.3 Hz).

PREPARATION EXAMPLE 87

Synthesis of 3-[2-(diethylamino)ethyl]-4-phenyl-2-oxo-1,2,3,4-tetrahydropyrido[4,3-d]pyrimidine In similar way as in Preparation Example 85, the title compound was synthesized from 4-amino-3-benzoylpyridine and 2-(diethylamino)ethylamine.

Melting point: 132.5°–134° C. (recrystallized from diethyl ether/ethanol)

$^1$H NMR(CDCl$_3$) δ; 8.26(1H, d, J=5.3 Hz), 8.16(1H, s), 7.30–7.36(5H, m), 6.63(1H, d, J=5.3 Hz), 5.80(1H, s) 3.81–3.89(1H, m), 2.97–3.09(1H, m), 2.73–2.76(1H, m), 2.44–2.60(5H, m), 0.99(6H, t, J=7.3 Hz).

Melting point of the HCl salt: over 230° C. (recrystallized from diethyl ether/ethanol)

PREPARATION EXAMPLE 88

Synthesis of 3-[2-(diethylamino)ethyl]-4-(3-methoxy)-phenyl-2-oxo-1,2,3,4-tetrahydropyrido[2,3-d]pyrimidine In similar way as in Preparation Example 85, the title compound was synthesized from 2-amino-3-(3-methoxybenzoyl)pyridine and 2-(diethylamino)ethylamine.

Melting point: 162.5°–164° C. (recrystallized from diethyl ether)

$^1$H NMR(CDCl$_3$) δ; 8.15(1H, dd, J=4.9 and 1.6 Hz), 7.88(1H, brs), 7.23–7.29(2H, m), 6.92(1H, dd, J=8.9, 1.0 Hz), 6.80–6.86(3H, m), 5.72(1H, s), 3.78–3.87 (1H, m), 3.78(3H, s), 2.91–3.02(1H, m), 2.67–2.77 (1H, m), 2.38–2.60(5H, m), 0.97(6H, t, J=7.3 Hz).

PREPARATION EXAMPLE 89

Synthesis of 3-(1-(benzylpiperidin-4-yl)-4-phenyl-2-oxo-1,2,3,4-tetrahydropyrido[4,3-d]pyrimidine (a) Synthesis of 3-[α-[{(1-benzylpiperidin-4-yl)-imino}benzyl]-4-trichloroacetylaminopyridine To a solution of 19.6 g (57 mmol) of 3-benzoyl-4-trichloroacetylaminopyridine in 100 mL of dimethylsulfoxide was added 13.0 g (68 mmol) of 4-amino-1-benzylpiperidine, and the mixture was stirred for 48 hours at ambient temperature. The reaction mixture was poured into water, and the mixture was extracted with ethyl acetate. The organic layer separated was washed with water and then with brine, dried on anhydrous sodium sulfate and then concentrated in vacuo. The residue was purified by means of column chromatography (silica gel, 1:1 ethyl acetate:hexane), and the resulting crude crystals were recrystallized with ethyl acetate to give 8.5 g (35.9 mmol) of the title compound.

Melting point: 152°–154° C. (decomposed)

$^1$H NMR(CDCl$_3$) δ; 8.60(1H, dd, J=5.9 Hz), 8.52(1H, d, J=5.9 Hz), 8.07(1H, s), 7.51–7.53(3H, m), 7.27–7.32 (5H, m), 7.14–7.18(2H, m), 3.44(2H, s), 3.14–3.22(1H, m), 2.87(2H, m), 1.96–2.08(2H, m), 1.52–1.83(4H, m).

(b) Synthesis of 3-[α-{(1-benzylpiperidin-4-yl)amino}-benzyl]-4-aminopyridine

To a solution of 18.0 g (34.9 mmol) of 3-[α-{(1-benzylpiperidin-4-yl)imino}benzyl]-4-trichloroacetylaminopyridine in 150 mL of ethanol was added 2.65 g (70 mmol) of sodium borohydride under ice-cooling and the mixture was stirred for 5 hours at ambient temperature. The reaction mixture was poured into water, and the ethanol was evaporated in vacuo. The residue was extracted with ethyl acetate. The organic layer separated was washed with water and then with brine, dried on anhydrous sodium sulfate and then concentrated in vacuo. Purification by means of column chromatography (silica gel, 1:9 methanol:chloroform) gave 4.82 g (12.9 mmol) of the title compound and 6.65 g (17.9 mmol) of 3-[α-{(1-benzyl-piperidin-4-yl)imino}benzyl]-4-aminopyridine.

To a suspension of 0.68 g (17.9 mmol) of lithium aluminum hydride in 100 mL of tetrahydrofuran was added dropwise a solution of 6.65 g (17.9 mmol) of 3-[α-{(1-benzylpiperidin-4-yl)imino}benzyl]-4-aminopyridine in tetrahydrofuran 30 ml under reflux, and the mixture was heated under reflux for 1 hour. After being cooled, the mixture was added sequentially with 0.7 mL of water, 0.7 mL of an aqueous 15% sodium hydroxide solution and 2 mL of water, under ice-cooling. After being stirred for 1 hour at ambient temperature, the reaction mixture was filtered through cerite. The filtrate was concentrated and the residue was purified by means of column chromatography (silica gel, 1:9 methanol:chloroform) to give 4.2 g (11.3 mmol) of the title compound.

$^1$H NMR(CDCl$_3$) δ; 8.06(1H, d, J=5.6 Hz), 7.98(1H, s), 7.24–7.35(10H, m), 6.42(1H, d, J=5.6 Hz), 5.59(2H, brs), 5.08(1H, s), 3.48(2H, s), 2.82(1H, m), 2.45(1H, m), 1.86–2.00(4H, m), 1.36–1.54(2H, m).

3-[α-{(1-benzylpiperidin-4-yl)imino}benzyl]-4-aminopyridine:

$^1$H NMR(CDCl$_3$) δ; 7.80(1H, d, J=5.6 Hz), 7.74(1H, s), 7.43–7.46(3H, m), 7.22–7.33(5H, m), 7.11–7.14(2H, m), 6.49(1H, d, J=5.6 Hz), 3.47(2H, s), 3.15–3.22 (1H, m), 2.77–2.81(2H, m), 1.95–2.02(2H, m), 1.73–1.87 (2H, m), 1.63–1.67(2H, m).

(c) Synthesis of 3-(1-benzylpiperidin-4-yl)-4-phenyl-2-oxo-1,2,3,4-tetrahydropyrido[4,3-d]pyrimidine To a solution of 8.0 g (21.5 mmol) of 3-[α-{(1-benzyl-piperidin-4-yl)amino}benzyl]-4-aminopyridine in 100 mL of tetrahydrofuran was added 5.0 g (3.1 mmol) of 1,1'-carbonyldiimidazole, and the mixture was heated under reflux for 8 hours. After being cooled, the reaction mixture was concentrated in vacuo, and the residue was purified by means of column chromatography (silica gel, 1:9 methanol:chloroform). The resulting crude crystals were recrystallized from diethyl ether/ethanol to give 4.2 g (10.5 mmol) of the title compound.

Melting point: 209°–210° C. (recrystallized from diethyl ether/ethanol)

$^1$H NMR(CDCl$_3$) δ; 8.35(1H, s), 8.26(1H, d, J=5.6 Hz), 8.09(1H, brs), 7.20–7.38(10H, m), 6.65(1H, d, J=5.6 Hz), 5.64(1H, s), 4.36(1H, m), 2.96(1H, m), 2.80 (1H, m), 2.00–2.10(3H, m), 1.50–1.65(3H, m).

Melting point of the HCl salt: over 230° C. (recrystallized from diethyl ether/ethanol)

PREPARATION EXAMPLE 90

Synthesis of 3-(piperidin-4-yl)-4-phenyl-2-oxo-1,2,3,4-tetrahydropyrido[2,3-d]pyrimidine In similar way as in Preparation Example 89, the title compound was synthesized from 3-benzoyl-2-trichloroacetylaminopyridine and 4-amino-1-benzylpiperidine.

¹H NMR(CDCl₃) δ; 8.74(1H, s), 8.19(1H, dd, J=5.0, 1.7 Hz), 7.19–7.46(11H, m), 6.85(1H, dd, J=7.6, 5.0 Hz), 5.55(1H, s), 4.40(1H, m), 3.44(2H, s), 2.93(1H, d, J=8.3 Hz), 2.78(1H, d, J=11.6 Hz), 1.94–2.08 (3H, m), 1.39–1.75(3H, m).

Melting point of the HCl: 186°–189° C. (recrystallized from diethyl ether/ethanol)

PREPARATION EXAMPLE 91

Synthesis of 3-(piperidin-4-yl)-4-phenyl-2-oxo-1,2,3,4-tetrahydropyrido[4,3-d]pyrimidine To a solution of 4.13.g (10.4 mmol) of 3-(1-benzylpiperidin-4-yl)-4-phenyl-2-oxo-1,2,3,4-tetrahydropyrido[4,3-d]pyrimidine in 250 mL of methanol were added 1.89 g (30 mmol) of ammonium formate and 0.3 g of 10% palladium-carbon, and the mixture was heated under reflux for 5 hours. After being cooled, the reaction mixture was filtered through cerite, and the filtrate was concentrated in vacuo. To the residue was added an aqueous saturated sodium hydrogencarbonate solution, and the mixture was extracted with chloroform. The organic layer separated was dried on potassium carbonate and then concentrated in vacuo. The residue was purified by means of column chromatography (silica gel, 10:100:900 aqueous ammonia methanol:chloroform) to give 2.67 g (8.66 mmol) of the title compound.

¹H NMR(CDCl₃) δ; 9.53(1H, brs), 8.31(1H, s), 8.26 (1H, d, J=5.3 Hz), 7.22–7.41(5H, m), 6.76(1H, d, J=5.3 Hz), 5.65(1H, s), 4.33(1H, m), 3.17(1H, d, J=12.2 Hz), 3.03(1H, d, J=12.5 Hz), 2.58–2.74(2H, m), 1.95–2.04(1H, m), 1.64(2H, d, J=10.6 Hz), 1.38–1.54 (1H, m).

PREPARATION EXAMPLE 92

Synthesis of 3-(1-allylpiperidin-4-yl)-4-phenyl-2-oxo-1,2,3,4-tetrahydropyrido[4,3-d]pyrimidine To a solution of 500 mg (1.62 mmol) of 3-(1piperidin-4-yl)-4-phenyl-2-oxo-1,2,3,4-tetrahydropyrido -[4,3-d]pyrimidine in 20 mL of ethanol were added sequentially 336 mg (2.43 mmol) of potassium carbonate and 235 mg (1.94 mmol) of allyl bromide, and the mixture was stirred for 4 hours at ambient temperature. The reaction mixture was concentrated in vacuo, the residue was partitioned between water and chloroform. The organic layer separated was dried on potassium carbonate and then concentrated in vacuo. The residue was purified by means of column chromatography (silica gel, 1:9 methanol:chloroform) to give 385 mg (1.10 mmol) of the title compound.

¹H NMR(CDCl₃) δ; 8.44(1H, s), 8.32(1H, s), 8.24(1H, d, J=5.3 Hz), 7.21–7.38(5H, m), 6.69(1H, d, J=5.3 Hz), 5.77–5.87(1H, m), 5.64(1H, s), 5.16(1H, d, J=7.9 Hz), 5.11(1H, d, J=1.0 Hz), 4.38(1H, m), 2.80–3.02(3H, m), 1.91–2.08(3H, m), 1.52–1.70(3H, m).

Melting point of the HCl salt: 155°–158° C. (recrystallized with diethyl ether/ethanol)

PREPARATION EXAMPLE 93

Synthesis of 3-[1-(3-thienylmethyl)piperidin-4-yl]-4-phenyl-2-oxo -1,2,3,4-tetrahydropyrido[4,3-d]pyrimidine To a solution of 500 mg (1.62 mmol) of 3-(piperidin-4-yl)-4-phenyl-2-oxo-1,2,3,4-tetrahydropyrido[4,3-d]pyrimidine in 30 mL of methanol were added 1,200 mg of 10% HCl/ethanol solution, 727 mg (6.48 mmol) of 3-thiophenecarboxaldehyde and 407 mg (6.48 mmol) of sodium cyanoborohydride under ice-cooling, and the mixture was stirred for 10 hours at ambient temperature. Then, the reaction mixture was concentrated in vacuo, and water was added to the residue. The mixture was adjusted to pH 10 and extracted with chloroform. The organic layer separated was dried on potassium carbonate, and then concentrated in vacuo. The residue was purified by means of column chromatography (silica gel, 1:9 methanol:chloroform) to give 550 mg (1.36 mmol) of the title compound.

¹H NMR(CDCl₃) δ; 8.93(1H, s), 8.34(1H, s), 8.27(1H, d, J=5.3 Hz), 7.20–7.39(6H, m), 7.07(1H, m), 7.01(1H, dd, J=5.0 and 1.3 Hz), 6.70(1H, d, J=5.3 Hz), 5.64(1H, s), 4.35(1H, m), 3.50(2H, s), 2.97(1H, d, J=6.9 Hz), 2.82(1H, d, J=10.9 Hz), 1.93–2.14(3H, m), 1.47–1.66 (3H, m).

Melting point of the HCl salt: over 230° C. (recrystallized from diethyl ether/ethanol)

PREPARATION EXAMPLE 94

Synthesis of 3-[1-(3-methoxybenzyl)piperidin-4-yl]-4-phenyl -2-oxo-1,2,3,4-tetrahydropyrido[4,3-d]pyrimidine In similar way as in Preparation Example 93, the title compound was synthesized from 3-(piperidin-4-yl)-4-phenyl-2-oxo-1,2,3,4-tetrahydropyrido[4,3-d]pyrimidine and 3-methoxybenzyldehyde.

¹H NMR(CDCl₃) δ; 8.40(1H, brs), 8.35(1H, s), 8.24 (1H, d, J=5.3 Hz), 7.18–7.39(6H, m), 6.76–6.84(3H, m), 6.67(1H, d, J=5.3 Hz), 5.64(1H, s), 4.35(1H, m), 3.80(3H, s), 3.53(2H, s), 2.96(1H, m), 2.81(1H, m).

Melting point of the HCl salt: over 230° C. (recrystallized from diethyl ether/ethanol)

PREPARATION EXAMPLE 95

Synthesis of 3-[2-(diethylamino)ethyl]-5-methyl-4-phenyl-2-oxo-1,2,3,4-tetrahydrothieno[2,3-d]pyrimidine In similar way as in Preparation Example 85, the title compound was synthesized from 2-amino-3-benzoyl-methylthiophene and 2-(diethylamino)ethylamine.

¹H NMR(CDCl₃) δ; 7.56(1H, brs), 7.28–7.34(5H, m), 6.18(1H, d, J=1.0 Hz), 5.49(1H, s), 3.56–3.66(1H, m), 3.05–3.15(1H, m), 2.64–2.74(1H, m), 2.46–2.60(4H, m), 2.31–2.41(2H, m), 1.83(3H, d, J=1.0 Hz), 1.00 (6H, t, J=7.3 Hz).

PREPARATION EXAMPLE 96

Synthesis of 3-(1-benzylpiperidin-4-yl)-4-phenyl-cis-3,4,4a, 5,8,8a-hexahydro-2(1H)-quinazolinone (a) Synthesis of 4,5-cis-4-methoxycarbonylamino-5-(α-hyroxybenzyl)cyclohexene To a solution of 500 mg (1.93 mmol) of 4,5-cis-4-methoxycarbonylamino-5-benzoylcyclohexene in 10 mL of methanol was added 162 mg (4.28 mmol) of sodium borohydride under ice-cooling, and the mixture was stirred for 3 hours at ambient temperature. The reaction mixture was poured into water, and methanol was distilled away in vacuo. The residue was extracted with chloroform, and the organic layer separated was dried on potassium carbonate and then concentrated in vacuo. The resulting residue was purified by means of column chromatography (silica gel, 1:1 hexane:ethyl acetate) to give 487 mg (1.87 mmol) of the title compound as a mixture of the diastereomers. The above mixed diastereomers (35 mg) was subjected to column chromatography (silica gel, 1:1 hexane:ethyl acetate) for separation and purification to give 10 mg of Diastereomer A and 25 mg of B. Diastereomer A had a higher Rf value, and Diastereomer B, a lower Rf value, on oil thin layer chromatography (developed with 1:1 hexane:ethyl acetate).

Diastereomer A:

$^1$H NMR(CDCl$_3$) δ; 7.18–7.36(5H, m), 5.48–5.62(2H, m), 5.03(1H, dd, J=3, 3 Hz), 4.73(1H, d, J=9 Hz), 4.28(1H, d, J=3 Hz), 3.91(1H, m), 3.73(3H, m), 2.39–2.50 (1H, m), 2.19–2.32(1H, m), 1.94–2.07(1H, m), 1.71–1.82(1H, m), 1.52–1.60(1H, m).

Diastereomer B:
$^1$H NMR(CDCl$_3$) δ; 7.23–7.36(5H, m), 5.59(2H, m), 5.10(1H, d, J=9 Hz), 4.48–4.55(2H, m), 4.21(1H, dd, J=10, 4 Hz), 3.74(3H, s), 2.46–2.53(1H, m), 2.13–2.20 (1H, m), 1.44–2.05(1H, m), 1.50–1.73(2H, m).

(b) Synthesis of 4,5-cis-4-methoxycarbonylamino-5-(α-chlorobenzyl)cyclohexene

To a solution of 415 mg (1.59 mmol) of the mixed diastereomers of 4,5-cis-4-methoxycarbonylamino-5 -(α-hydroxybenzyl)cyclohexane in 10 mL of 1,2-dichloroethane were added 0.17 mL (1.76 mmol) of carbon tetrachloride and 512 mg (1.95 mmol) of triphenylphosphine at ambient temperature. The mixture was stirred for 2 hours at ambient temperature and then heated under reflux for 2 hours. The solvent was distilled away in vacuo and the resulting residue was purified by means of column chromatography (silica gel, chloroform) to give 219 mg (0.78 mmol) of the mixed diastereomers of the title compound.

$^1$H NMR(CDCl$_3$) δ; 7.20–7.41(5H, m), 5.76–5.81(1H, m), 5.58–5.67(2H, m), 4.61–5.05(2H, m), 3.60–3.71(3H, m), 1.81–2.82(5H, m).

(c) Synthesis of 3-(1-benzylpiperidin-4-yl)-4-phenyl -cis-3,4,4a,5,8,8a-hexahydro-2(1H)-quinazolinone To a solution of 200 mg (0.72 mmol) of 4,5-cis-methoxycarbonylamino-5-(α-chlorobenzyl)cyclohexene in 10 mL of dimethylformamide were added 1.08 g (9.43 mmol) of 4-amino-1-benzylpiperidine and 1 mL of triethylamine, and the mixture was stirred for 20 hours at temperature of approximately 80° C. The solvent was distilled away in vacuo and the residue was partitioned between water and chloroform. The organic layer separated was dried on potassium carbonate and then concentrated in vacuo. The resulting residue was subjected to column chromatography (silica gel, 1:10:90 aqueous ammonia:methanol:chloroform) for separation and purification to give 64 mg (0.16 mmol) of Diastereomer A and 112 mg (0.28 mmol) of Diastereomer B. Diastereomer A had a higher Rf value, and Diastereomer B, a lower Rf value, on thin layer chromatography (developed with 1:10:90 aqueous ammonia:methanol:chloroform).

Diastereomer A:
$^1$H NMR(CDCl$_3$) δ; 7.21–7.36(10H, m), 5.70(1H, m), 5.56(1H, m), 4.85(1H, d, J=5 Hz), 4.64(1H, d, J=9 Hz), 4.34(1H, d, J=8 Hz), 3.99(1H, m), 3.52(1H, m), 3.47 (2H, s), 2.78(2H, m), 2.24–2.34(1H, m), 1.99–2.12 (6H, m), 1.89(2H, m), 1.40(2H, m).

Melting point of the citrate: 120°–122° C. (recrystallized from isopropanol/ethyl acetate)

Diastereomer B:
$^1$H NMR (CDCl$_3$) δ; 7.20–7.37(10H, m), 5.52–5.77(2H, m), 4.84(1H, d, J=5 Hz), 4.76(1H, d, J=9 Hz), 4.50 (1H, d, J=8 Hz), 3.81–4.01(2H, m), 3.53(1H, m), 3.48 (2H, s), 2.76–2.87(2H, m), 1.87–2.33(9H, m), 1.45 (2H, m).

PREPARATION EXAMPLE 97

Synthesis of 3-(piperidin-4-yl)-4-phenyl-cis-3,4,4a,5,8,8a-hexahydro-2(1H)-quinazolinone In similar way as in Preparation Example 15, the title compound was synthesized from 3-(1-benzyl-piperidin-4-yl)-4-phenyl-cis-3,4,4a,5,8,8a-hexahydro -2-(1H) -quinazolinone.

$^1$H NMR(CDCl$_3$) δ; 7.23–7.34(5H, m), 5.69(1H, m), 5.56 (1H, m), 4.94(1H, d, J=9 Hz), 4.80(2H, m), 3.94 (1H, m), 3.61(1H, m), 2.99(2H, m), 2.62(2H, m), 1.88–2.32(6H, m), 1.20–1.33(2H, m).

PREPARATION EXAMPLE 98

Synthesis of 3-(1-allylpiperidin-4-yl)-4-phenyl-cis-3,4,4a,5,8,8a-hexahydro-2(1H)-quinazolinone In similar way as in Preparation Example 31, the title compound was synthesized from 3-(piperidin-yl)-4-phenyl-cis-3,4,4a,5,8,8a-hexahydro-2-(1H)quinazolinone.

$^1$H NMR(CDCl$_3$) δ; 7.14–7.29 (5H, m), 5.63–5.81 (2H, m), 5.49(1H, m), 5.03–5.11(3H, m), 4.65–4.79(2H, m), 4.45(1H, d, J=8 Hz), 3.93(1H, m), 3.49(2H, m), 2.85 (2H, d, J=7 Hz), 2.72(2H, m), 1.65–2.27(6H, m), 1.31 (2H, m).

PREPARATION EXAMPLE 99

Synthesis of 3-[1-(3-thienylmethyl)piperidin-4-yl]-4 -phenyl-cis-3,4,4a,5,8,8a-hexahydro-2(1H)-quinazolinone In similar way as in Preparation Example 36, the title compound was synthesized from 3-(piperidin-4-yl)-4-phenyl-cis-3,4,4a,5,8,8a-hexahydro-2(1H) -quinazolinone and 3-thiophenecarboxaldehyde.

$^1$H NMR(CDCl$_3$) δ; 7.25–7.35(6H, m), 7.12(1H, s), 7.05(1H, dd, J=5, 1 Hz), 5.71(1H, m), 5.57(1H, m), 4.86(1H, d, J=5 Hz), 4.56(1H, d, J=8.6 Hz), 4.26(1H, d, J=7.6 Hz), 4.02(1H, m), 3.54(2H, s), 2.83(2H, d, J=11.9 Hz), 1.90–2.36(8H, m), 1.37–1.50(2H, m).

PREPARATION EXAMPLE 100

Synthesis of 3-[1-(3-methoxybenzyl)piperidin-4-yl]-4 -phenyl-cis-3,4,4a,5,8,8a-hexahydro-2(1H)-quinazolinone In similar way as in Preparation Example 36, the title compound was synthesized from 3-(piperidin-4-yl)-phenyl-cis-3,4,4a,5,8,8a-hexahydro-2(1H)-quinazolinone and 3-methoxybenzaldehyde.

$^1$H NMR(CDCl$_3$) δ; 7.19–7.35(6H, m), 6.88(1H, m), 6.78–6.82(1H, m), 5.74(1H, m), 5.57(1H, m), 4.86(1H, d, J=5 Hz), 4.61(1H, d, J=8.9 Hz), 4.33(1H, d, J=7.3 Hz), 4.02(1H, m), 3.81(3H, s), 3.57(1H, m), 3.45(2H, s), 2.80–2.88(2H, m), 1.89–2.35(8H, 1.37–1.48(2H, m).

PREPARATION EXAMPLE 101

Synthesis of 3-(1-benzylpiperidin-4-yl)-4-phenyl-cis -octahydro-2(1H)-quinazolinone To a solution of 391 mg (0.97 mmol) of Diastereomer A of 3-(1-benzylpiperidin-4-yl)-4-phenyl- cis-3,4,4a, 5,8,8a-hexahydro-2 (1H)-quinazolinone in 15 mL of methanol was added 90 mg of 30% platinum oxide, and the mixture was stirred for 6 hours in an atmosphere of hydrogen at ambient temperature. After being filtered through cerite, the solvent was distilled away in vacuo, and the resulting residue was subjected to column chromatography (silica gel, 1:10:90 aqueous ammonia:methanol:chloroform) for separation and purification to give 352 mg (0.87 mmol) of the title compound.

$^1$H NMR(CDCl$_3$) δ; 7.25–7.36(10H, m), 4.93(1H, d, J=7.6 Hz), 4.73(1H, d, J=5.3 Hz), 4.21(1H, d, J=8.3 Hz), 3.54–3.62(2H, m), 3.48(2H, s), 2.76(2H, m), 2.09(2H, m), 1.74–1.91(8H, m), 1.15–1.48(9H, m).

PREPARATION EXAMPLE 102

Synthesis of 3-(piperidin-4-yl)-4-phenyl-cis-octahydro -2(1H)-quinazolinone

In similar way as in Preparation Example 15, the title compound was synthesized from 3-(1-benzyl-piperidin-4-yl)-4-phenyl-cis-octahydro-2(1H)-quinazolinone.

¹H NMR(CDCl₃) δ; 7.28–7.36(5H, m), 5.14(1H, d, J=7.6 Hz), 4.73(1H, d, J=5 Hz), 4.37(1H, d, J=8.3 Hz), 3.56–3.70(3H, m), 2.93–3.02(2H, m), 2.60(2H, m), 1.73–2.08(5H, m), 1.18–1.48(6H, m).

PREPARATION EXAMPLE 103

Synthesis of 3-(1-allylpiperidin-4-yl]-4-phenyl-cis-octahydro-2(1H)-quinazolinone In similar way as in Preparation Example 31, the title compound was synthesized from 3-(piperidin-4-yl)-4-phenyl-cis-octahydro-2(1H)-quinazolinone ¹H NMR(CDCl₃) δ; 7.22–7.36(5H, m), 5.73–5.88(1H, m), 5.06–5.19(3H, m), 4.74(1H, d, J=5.3 Hz), 4.35 (1H, d, J=7.9 Hz), 3.51–3.67(2H, m), 2.80–2.96(5H, m), 1.73–2.21(7H, m), 1.15–1.48(6H, m).

PREPARATION EXAMPLE 104

Synthesis of 3-[1-(3-thienylmethyl)piperidin-4-yl]-4 -phenyl-cis-octahydro-2(1H)-quinazolinone In similar way as in Preparation Example 36, the title compound was synthesized from 3-(piperidin-4-yl)-4-phenyl-cis-octahydro-2(1H)-quinazolinone and 3-thiophenecarboxaldehyde.

¹H NMR(CDCl₃) δ; 7.20–7.34(6H, m), 7.11(1H, m), 7.02(1H, m), 5.29(1H, d, J=7.9 Hz), 4.73(2H, d, J=5 Hz), 3.51(2H, s), 3.45–3.68(3H, m), 2.80(2H, m), 1.70–1.85(5H, m), 1.12–1.44(6H, m).

PREPARATION EXAMPLE 105

Synthesis of 3-[1-(3-methoxybenzyl)piperidin-4-yl]-4 -phenyl-cis-octahydro-2(1H)-quinazolinone In similar way as in Preparation Example 36, the title compound was synthesized from 3-(piperidin-4-yl)-4-phenyl-cis-octahydro-2(1H)-quinazolinone and 3-methoxybenzaldehyde.

¹H NMR(CDCl₃) δ; 7.18–7.34(5H, m), 6.78–6.89(3H, m), 5.25(1H, d, J=7.9 Hz), 4.72(1H, d, J=5 Hz), 4.67(1H, d, J=7.6 Hz), 3.79(3H, s), 3.46(2H, s), 3.52–3.74(3H, m), 2.77(2H, m), 2.10(2H, m), 1.70–1.85 (5H, m), 1.13–1.46(6H, m).

PREPARATION EXAMPLE 106

Synthesis of 3-(1-benzylpiperidin-4-yl)-4-phenyl-trans -3,4,4a,5,8,8a-hexhydro-2-(1H)-quinazolinone (a) Synthesis of 4,5-trans-4-methoxycarbonylamino-5benzoylcyclohexene To a solution of 13.74 g (53.0 mmol) of 4,5-cis-methoxycarbonylamino-5-benzoylcyclohexene in 400 mL of methanol was added 3.31 g (61.27 mmol) of sodium methoxide, and the mixture was heated under reflux for 20 hours. The solvent was distilled away in vacuo, then the residue was partitioned between water and chloroform. The organic layer separated was dried on potassium carbonate, and then concentrated in vacuo. The resulting residue was purified by means of column chromatography (silica gel, 1:1 chloroform:ethyl acetate). The crude crystals obtained were recrystallized from ethyl acetate/hexane to give 6.94 mg (29.7 mmol) of the title compound.

Melting point: 122°–124° C.

¹H NMR(CDCl₃) δ; 8.07(2H, m), 7.46–7.60(3H, m), 5.76(1H, m), 5.65(1H, m), 4.90(1H, m), 4.20(1H, m), 4.02(1H, m), 3.63(3H, s), 2.36(3H, m), 2.17(1H, m).

(b) Synthesis of 4,5-trans-4-methoxycarbonylamino-5-(α-hydroxybenzyl)cyclohexene In similar way as in Preparation Example 96 (a), the title compound, as an about 2:3 mixture of the diastereomers, was synthesized from 4,5-trans-4-methoxy-carbonylamino-5-benzoylcyclohexene.

¹H NMR(CDCl₃) δ; 7.17–7.40(5H, m), 5.49–5.65(2.6H, m), 5.24(0.4H, m), 5.03(0.6H, m), 4.94(0.6H, d, J=10.2 Hz), 4.59(0.4H, m), 4.34(0.4H, d, J=4 Hz), 3.81–4.08 (1H, m), 3.71(1.8H, s), 3.59(1.2H, s), 1.57–2.61 (5H, m).

(c) Synthesis of 4,5-trans-4-methoxycarbonylamino-5-(α-chlorobenzyl)cyclohexene

In similar way as in Preparation Example 96 (b), the title compound, as a mixture of the diastereomers, was synthesized from 4,5-trans-4-methoxycarbonylamino-5-(α-hydroxybenzyl)cyclohexene.

¹H NMR(CDCl₃) δ; 7.20–7.44(5H, m), 5.56–5.71(2H, m), 5.02(1H, d, J=6.9 Hz), 4.76(1H, m), 3.57–3.76 (4H, m), 2.49–2.56(2H, m), 1.93–2.33(3H, m).

(d) Synthesis of 3-(1-benzylpiperidin-4-yl)-4-phenyl -trans-3,4,4a,5,8,8a-hexahydro-2(1H)-quinazolinone To a solution of 202 mg (0.72 mmol) of 4,5-trans-4-methoxycarbonylamino-5-(α-chlorobenzyl)cyclohexene in 10 mL of acetonitrile were added 205 mg (1.08 mmol) of 4-amino-1-benzylpiperidine, 163 mg (1.09 mmol) of sodium iodide and 300 mg (2.17 mmol) of potassium carbonate, and the mixture was stirred in an autoclave for 10 hours at temperature of approximately 120° C. After being cooled, the reaction mixture was filtered through cerite, and the filtrate was concentrated in vacuo. The residue was partitioned between water and chloroform. The organic layer separated was washed with brine, dried on potassium carbonate and then concentrated in vacuo. The residue was purified by means of column chromatography (silica gel, 1:10:90 aqueous ammonia:methanol:chloroform) to give 119 mg (0.30 mmol) of the title compound.

¹H NMR(CDCl₃) δ; 7.34(3H, m), 7.20–7.32(7H, m), 5.53–5.63(2H, m), 5.01(1H, d, J=10.2 Hz), 3.45–3.58 (2H, m), 3.45(2H, m), 2.60–2.78(3H, m), 1.63–2.17 (11H, m).

PREPARATION EXAMPLE 107

Synthesis of 3-(1-benzylpiperidin-4-yl)-4-phenyl-trans-octahydro-2(1H)-quinazolinone In similar way as in Preparation Example 101, the title compound was synthesized from 3-(1-benzyl-piperidin-4-yl)-4-phenyl-trans-3,4,4a,5,8,8a-hexahydro -2(1H)-quinazolinone.

¹H NMR(CDCl₃) δ; 7.40–7.47(3H, m), 7.19–7.33(7H, m), 5.05(1H, d, J=10.6 Hz), 3.51(1H, m), 3.46(2H, m), 3.28(1H, m), 2.76(2H, m), 2.26(1H, m), 2.09(2H, m), 1.61–1.86(7H, m), 0.94–1.49(5H, m).

PREPARATION EXAMPLE 108

Synthesis of 3-(1-benzylpiperidin-4-yl)-4-phenyl-3,4 -dihydro-2(1H)-quinazolinethione To a solution of 503 mg (1.35 mmol) of α-(2-aminophenyl)-N-(1-benzylpiperidin-4-yl)benzylamine in 10 mL of tetrahydrofuran was added 300 mg (1.68 mmol) of 1,1'-thiocarbonyldiimidazole, and the mixture was heated under reflux for 3 hours. After being cooled, the reaction mixture was concentrated in vacuo, and the residue was purified by means of column chromatography (silica gel, 1:4 ethyl acetate:chloroform) to give 540 mg (1.30 mmol) of the title compound.

Melting point of the HCl salt: 212°–214° C. (recrystallized from diethyl ether/ethanol)

¹H NMR(CD₃ OD) δ; 7.13–7.57(12H, m), 6.88–7.03(2H, m), 5.70–5.84(2H, m), 4.85(2H, s), 3.02–3.59(4H, m), 2.43(1H, m), 1.74–2.04(3H, m).

PREPARATION EXAMPLE 109

Synthesis of 6-chloro-3-[3-(trimethylammonio)propyl]-4-phenyl-3,4-dihydro-2(1H)-quinazolinone iodide To a solution of 418 mg (1.22 mmol) of 6-chloro-[3-(dimethylamino)propyl]-4-phenyl-3,4-dihydro-2(1H)quinazolinone in 30 mL of ethanol was added 176 mg (1.24 mmol) of methyl iodide, and the mixture was stirred for 4 days at ambient temperature. The crystals formed were separated by filtration, and washed with diethyl ether to give 374 mg (0.77 mmol) of the title compound.

Melting point: 164°–166° C.

$^1$H NMR(CD$_3$ OD ) δ; 7.28–7.45(5H, m), 7.09–7.15(2H, m), 6.83(1H, m), 5.77(1H, s), 3.61(1H, m), 3.30(2H, m), 3.15(1H, m), 3.06(9H, s), 2.00(2H, m).

PREPARATION EXAMPLE 110

Synthesis of 3-(1-methyl-3-quinuclidinio)-4-phenyl -3,4-dihydro-2(1H)-quinazolinone iodide In similar way as in Preparation Example 109, the title compound was synthesized from Diastereomer B of 3-(quinuclidin-3-yl)-4-phenyl-3,4-dihydro-2(1H)-quinazolinone.

Melting point: over 230° C. (recrystallized from ethanol/acetone)

$^1$H NMR(DMSO-d$_6$) δ; 9.89(1H, s), 7.11–7.48(7H, m), 6.80–6.95(2H, m), 5.76(1H, s), 3.80–4.01(2H, m), 3.27–3.59(5H, m), 2.92(3H, s), 2.28–2.33(1H, m), 1.70–2.08(4H, m).

PREPARATION EXAMPLE 111

Synthesis of 3-[(2S)-1,1-diethyl-2-pyrrolidinio]-methyl-4-phenyl-3,4-dihydro-2(1H)-quinazolinone iodide To a solution of 156 mg (0.46 mmol) of Diastereomer A1 of 3-[(2S)-1-ethylpyrrolidin-2-yl]methyl-4 -phenyl-3,4-dihydro-2(1H)-quinazolinone in 10 mL of chloroform was added 819 mg (5.25 mmol) of ethyl iodide, and the mixture was heated under reflux for 4 days. After being cooled, the reaction mixture was filtered through cerite, and the filtrate was concentrated in vacuo. The resulting solid matter was washed with diethyl ether/ethanol to give 63 mg (0.13 mmol) of the title compound in the amorphous state.

$^1$H NMR(CD$_3$ OD) δ; 7.25–7.43(5H, m), 7.13–7.19(2H, m), 6.84–6.96(2H, m), 5.79(1H, s), 4.18–4.35(2H, m), 3.28–3.60(6H, m), 3.04–3.12(1H, m), 2.40(1H, 2.08–2.20(3H, m).

Formulation Example 1

Formulation for tablets is exemplified as follows:

|  | Amount (mg/tablet) |
|---|---|
| HCl salt of the compound in Preparation Example 89 | 10 |
| Lactose | 72.5 |
| Corn starch | 30 |
| Carboxymethylcellulose Ca | 5 |
| Hydroxypropylcellulose (HPC-L) | 2 |
| Magnesium stearate | 0.5 |
| Total | 120 mg |

Tablets of each 120 mg can be formulated by mixing the above ingredients and tabletting.

Formulation Example 2

Formulation for injection is exemplified as follows

| HCl salt of the compound in Preparation Example 89 | 1 mg |
|---|---|
| Isotonic sodium chloride solution | 10 mL |

An injection can be formulated by sterilizing the solution composed of the above ingredients by filteration, filling the solution in a vial which has been washed and sterilized, closing the vial with a rubber stopper which has been washed and sterilized, and sealing the vial with a flip-off-cap.

Testing Example 1

To estimate the effect of preventing Ca$^{2+}$ overload in myocardial cells, which is one of the targets of the present invention, a preventing effect on ouabain intoxication was measured using the compounds of the invention. The ouabain intoxication is caused by occurrence of Ca$^{2+}$ overload when Ca$^{2+}$ is entered myocardial cells (see Am. J. Physiol., 1989, 256, C1273–C1276; and Basic Res. Cardiol., 1989, 84, 553–563), and accordingly, it can be said that compounds which prevent ouabain action could prevent Ca$^{2+}$ overload in myocardial cells.

Testing Method (1) Preparation of the specimens

Male guinea pig (Charles River Japan, Inc.) was killed by assaulting the head for cervical dislocation. The heart was dissected out immediately, and the contraction was stopped promptly in a cooled Tyrode solution. The left atria were quickly excised. The left atrial preparations were suspended in an organ bath which had been filled with 25 mL of a Tyrode solution maintained at temperature of 32°±0.3° C. and bubbled with a mixed 95% O$_2$+5% CO$_2$ gas, and the preparation was loaded with a 0.45–0.55 g weight. Using an electronic stimulator (Dia Medical DPS-160B), the preparation was driven electrically by rectangular wave stimulation (stimulation frequency: 2 Hz, pulse duration: 3 msec, 50% more voltage of the threshold) via bipolar silver electrodes. The tension was recorded isometrically on a linearly recording thermostylus oscillograph (Graphtec, WR-3101) via a force-displacement transducer (Toyo Baldwin T 7-30-240) and a carrier-amplifier (Nihon Denki San'ei Type-1829). The preparation was equilibrated for 1 hour after the suspension, and the experiment was started after identifying the good stability of the developed tension.

(2) Evaluation of the improving effect of the present compounds against ouabain-induced myocardial dysfunction A compound of the present invention was added thereto so as to 3×10$^{-6}$M, and, after 10 minutes standing, ouabain (Merck) was applied so as to be 10$^{-6}$M. In each case the developed tension was recorded 40 minutes after the ouabain treatment, and the developed and resting tensions were recorded 60 minutes after. The developed and resting tensions are shown as the percent change (developed tension % and resting tension %) at every time period based on 100% of the value just before the ouabain treatment, and determined as P<0.05 being significant in Student's t test versus the untreated control. Each of the testing compounds was dissolved in purified water so as to be 3×10$^{-4}$M to make a source solution.

(3) Test compounds

Compound No. 1: Preparation Example 1:citrate
Compound No. 2: Preparation Example 2:HCl salt
Compound No. 3: Preparation Example 3:HCl salt
Compound No. 4: Preparation Example 8:HCl salt of Diastereomer A
Compound No. 5: Preparation Example 15:HCl salt
Compound No. 6: Preparation Example 24:citrate
Compound No. 7: Preparation Example 25:HCl salt of Diastereomer A
Compound No. 8: Preparation Example 53:meso-tartarate
Compound No. 9: Preparation Example 84:HCl salt
Compound No. 10: Preparation Example 109
Compound No. 11: Preparation Example 110
Compound No. 12: Preparation Example 111

Testing results

Testing results of the compounds are shown in Table 1.

Testing method (1) Culture of myocardial cells

According to the procedure described in the literature (see Circ. Res., 1993, 73, 758–770), myocardial cells were isolated from ICR mouse fetus 14–15 days after pregnancy (Charles River Japan, Inc.), and incubated. That is to say, ventricular muscle was removed from the fetus myocardium. After being minced, the myocardial cells were isolated using a 0.25% trypsin solution (Gibco). The myocardial cells were placed on a cover glass coated with fibronectins (Koken), and incubated in an Eagle MEM medium containing 10% fetal calf serum (Gibco) in a $CO_2$ incubator (Astec BL-160: 37° C., 5% $CO_2$+95% air).

(2) Estimation of the changes in cytosolic $Ca^{2+}$ concentration by the substitution with a $Na^+$ free solution The cells after 4 to 6 day incubation were washed with a solution containing 117.4 mM of NaCl, 5.4 mM of KCl, 0.8 mM of $MgCl_2$, 2, 1.8 mM of $CaCl_2$, 0.1% of glucose and 5 mM of HEPES (Nakarai Tesque) of pH 7.4 (normal HEPES

TABLE 1

Effects of the test compounds on contractile failure and increase in resting tension induced by ouabain in electrically stimulated guinea pig left atria

| Test compounds | Contractile force (%) | | Resting tension (%) |
| --- | --- | --- | --- |
| | 40 minutes | 60 minutes | 60 minutes |
| | (after the treatment with ouabain) | | |
| Untreated control(n = 12) | 9.90 ± 2.82 | 0.51 ± 0.51 | 367.39 ± 27.86 |
| Compound No. 1(n = 6) | 65.93 ± 15.87* | 7.93 ± 2.72* | 224.43 ± 10.00** |
| Compound No. 2(n = 6) | 68.64 ± 33.04 | 16.12 ± 9.99 | 266.98 ± 22.47* |
| Compound No. 3(n = 6) | 96.99 ± 22.66* | 18.94 ± 7.61 | 228.35 ± 32.71* |
| Compound No. 4(n = 6) | 18.16 ± 5.53 | 3.44 ± 0.35** | 321.62 ± 24.62 |
| Compound No. 5(n = 6) | 86.48 ± 38.59 | 30.35 ± 13.30 | 287.25 ± 48.30 |
| Compound No. 6(n = 5) | 123.55 ± 33.75* | 52.51 ± 15.39* | 144.24 ± 22.66** |
| Compound No. 7(n = 6) | 33.75 ± 7.32** | 10.08 ± 3.59* | 302.31 ± 24.33 |
| Compound No. 8(n = 6) | 86.39 ± 10.30** | 19.15 ± 2.60** | 154.49 ± 6.46** |
| Compound No. 9(n = 6) | 13.46 ± 5.05 | 0.91 ± 0.91 | 364.59 ± 25.63 |
| Compound No. 10(n = 6) | 7.11 ± 1.29 | 3.86 ± 0.61** | 365.24 ± 26.34 |
| Compound No. 11(n = 6) | 19.43 ± 13.99 | 2.53 ± 1.60 | 330.47 ± 46.58 |
| Compound No. 12(n = 6) | 22.93 ± 11.63 | 5.53 ± 2.25 | 330.71 ± 12.42 |

The contractile force and resting tension were expressed as percentage to the values before the treatment with ouabain. The test compounds were applied 10 minutes before the treatment with ouabain.

Each value set forth the mean ±S.E., and n means number of the experiments.

\* P<0.05 as compared with the untreated control.

\*\* P<0.01 as compared with the untreated control.

Testing Example 2

To estimate the effect of preventing $Ca^{2+}$ overload in myocardial cells, which is one of the targets of the present invention, the effect of preventing the influx of $Ca^{2+}$ into myocardial cells was investigated in cultured myocardial cells. The evaluation was made basing upon the preventing effect on the increase in cytosolic $Ca^{2+}$ concentration due to the substitution with $Na^+$ free solution, according to the method described in the literatures (see Mol. Pharmacol., 1986, 30, 164–170; and Circ. Res., 1992, 70, 804–811).

Figure 2:
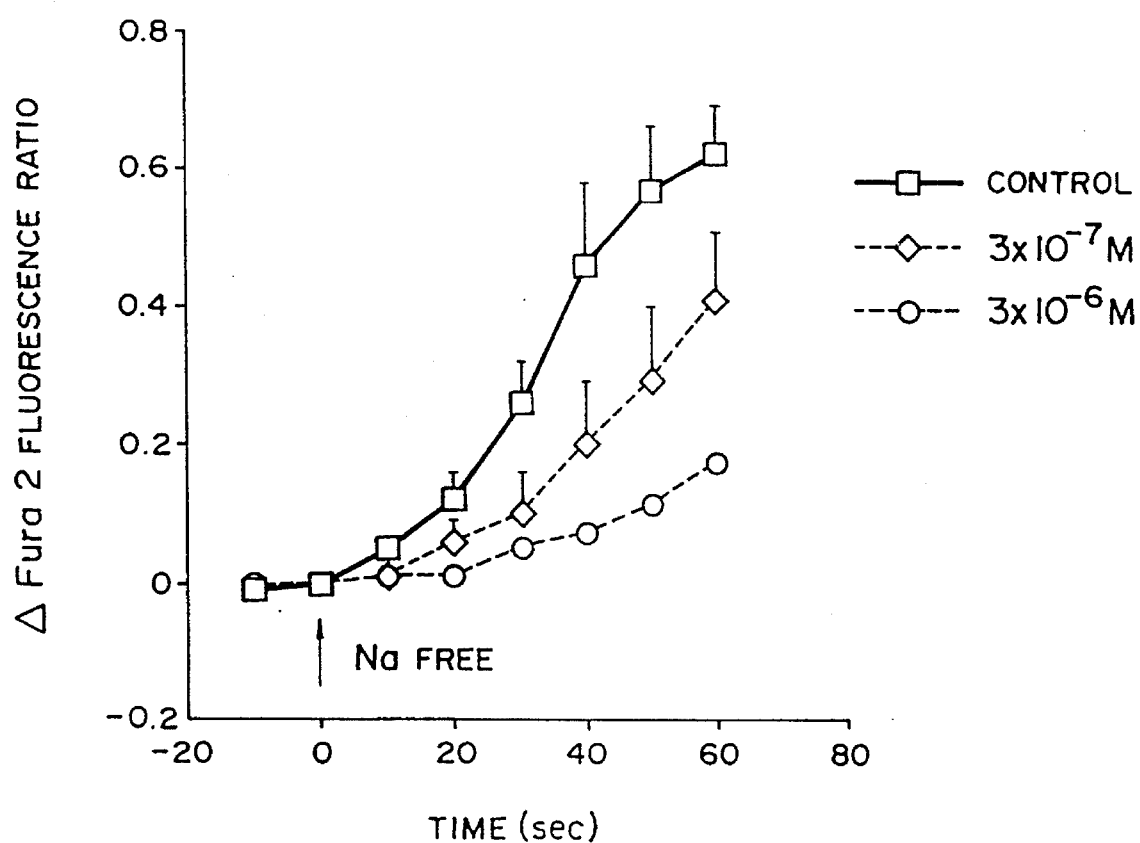
FIG. 2 is a graph showing the preventing effect of the Compound No. 13 on the increase in cytosolic $Ca^{2+}$ concentration through substitution with a $Na^+$ free solution (Preparation Example 89; hydrochloride). The axis of abscissas represents the time period after the treatment with the test compound, and the axis of ordinates represents the change in Fura 2-AM fluorescence ratio during perfusion of the Na free HEPES solution.

The results in Testing Example 2 are shown in FIGS. 1 and 2.

solution), and then incubated (light shielded, 37° C.) for 20 minutes in a normal HEPES solution containing 20 μM of Fura 2-AM (Dojin) and 0.4% of bovine serum albumin (Sigma), thereby to load Fura 2-AM into the cells. After being washed twice with 2 mL of a normal HEPES solution, the cell-adhered cover glass was installed in a perfusion chamber which can be kept at 37° C., and a normal HEPES solution, through which a highly pure oxygen gas has been passed, was perfused on it. According to the procedure described in the literature (see Biochimica et Biophysica Acta, 1981, 642, 158–172), then, the cover glass was perfused for 5 minutes with a solution containing 28 mM of NaCl, 108 mM of choline-Cl (Wako Pure Chemical Industries, LTD.), 0.1 mM of EGTA (Wako Pure Chemical Industries, LTD.), 0.1% of glucose and 5 mM of HEPES solution of pH 7.4 (28 mM of Na-loaded HEPES solution), thereby to load $Na^+$ to the cells, and then perfused with a solution containing 135 mM of choline-Cl, 1.8 mM of $CaCl_2$, 0.1% of glucose and 5mM of HEPES of pH 7.4 (Na free HEPES solution), thereby to increase the cytosolic $Ca^{2+}$ concentration. The cytosolic $Ca^{2+}$ concentrations were determined by measuring the fluorescence intensity at 500 nm excited at 340 nm and 380 nm using a microscopic dual-wavelength fluorometer (Jasco CAM-230), and calculated from the fluorescence ratio (340 nm/380 nm). Each agent was dissolved in a purified water to make a 1 mM solution, which was then suitably diluted with the perfused solution to a definite concentration, before use.

(3) Evaluation of the preventing effect of the present compounds on the increase in cytosolic Ca²⁺ concentration The compound of the present invention was applied at the time of both the perfusion with a 28 mM Na-loaded HEPES solution and the perfusion with Na free HEPES solution, and the change in the Fura 2-AM fluorescence ratio in the perfusion with the Na free HEPES solution (changes in cytosolic Ca²⁺ concentration) was observed. The preventing effect of the test compound was evaluated by comparing the changes in Fura 2-AM fluorescence ratios in the perfusion with the Na free HEPES solution with respect to the treated and untreated groups.

What is claimed is:

1. A method for preventing or treating a disease caused by influx of calcium ions into cells, which comprises administering a pharmaceutically effective amount of a quinazolinone derivative represented by the formula:

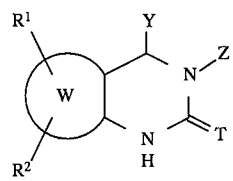

(1)

wherein T represents an oxygen or sulfur atom; Y represents an alkyl, cycloalkyl, cycloalkylalkyl, phenyl, substituted phenyl, aralkyl, substituted aralkyl, heteroaryl or substituted heteroaryl group; ring W represents a benzene, pyridine, thiophene, or 5–10 membered cycloalkene or cycloalkane ring; $R^1$ and $R^2$ represent, independently, a hydrogen or halogen atom, or a lower alkyl, cyano trifuloromethyl, nitro, amino, substituted amino, hydroxy, lower alkoxy, lower alkylthio, lower alkyl-sulfinyl or lower alkylsulfonyl group; Z represents the following group (1a) or (1b):

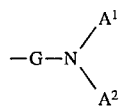

(1a)

in which $A^1$ and $A^2$ represent, independently, a hydrogen atom, or an alkyl, substituted alkyl, cycloalkyl, saturated heterocyclic, cycloalkylalkyl, cycloalkenyl-alkyl, aralkyl, substituted aralkyl, heteroarylalkyl, substituted heteroarylalkyl or —CH₂R³ group, R³ being an alkenyl or alkynyl group, or $A^1$ and $A^2$ may be bound to each other to form a hetero ring which is a five to seven membered ring with one or two nitrogen atoms or with one nitrogen atom and one oxygen atom; and G represents a straight chain alkylene group having 1 to 6 carbon atoms, a branched alkylene group having 1 to 6 carbon atoms, or the following group:

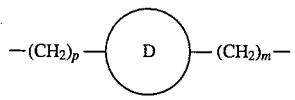

p and m stand, independently, an integer from 0 to 2; and D is a cycloalkane ring; or

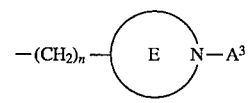

(1b)

in which n represents an integer of 0 to 2; ring E represents a 4–8 membered saturated heterocyclic ring containing a nitrogen atom; and $A^3$ represents a hydrogen atom, or an alkyl, substituted alkyl, cycloalkyl, saturated heterocyclic, cycloalkylalkyl, cycloalkenylalkyl, aralkyl, substituted aralkyl, heteroarylalkyl, substituted heteroarylalkyl or —CH₂R³ group, R³ being an alkenyl or alkynyl group, or may be bound to the ring E to form a quinuclidin-3-yl or guinuclidin-4-yl; or a pharmaceutically acceptable acid-addition salt or quaternary ammonium salt thereof, to a patient.

2. A method according to claim 1, wherein the disease is one selected from the group consisting of ischemic heart disease, ischemic cerebral disease and ischemic renal disease.

3. A method according to claim 1, wherein the ring W is a benzene ring.

4. A quinazolinone derivative represented by the formula:

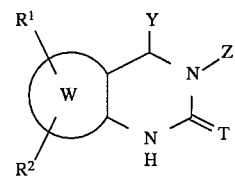

(1)

wherein T represents an oxygen or sulfur atom; Y represents an alkyl, cycloalkyl, cycloalkylalkyl, phenyl, substituted phenyl, aralkyl, substituted aralkyl, heteroaryl or substituted heteroaryl group; $R^1$ and $R^2$ represent, independently, a hydrogen or halogen atom, or a lower alkyl, cyano trifuloromethyl, nitro, amino, substituted amino, hydroxy, lower alkoxy, lower alkylthio, lower alkyl-sulfinyl or lower alkyl-sulfonyl group; ring W represents a pyridine, thiophene, or 5–10 membered cycloalkene or cycloalkane ring; Z represents the following group (1a) or (1b):

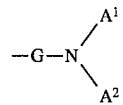

(1a)

in which $A^1$ and $A^2$ represent, independently, a hydrogen atom, or an alkyl, substituted alkyl, cycloalkyl, saturated heterocyclic, cycloalkylalkyl, cycloalkenylalkyl, aralkyl, substituted aralkyl, heteroarylalkyl, substituted heteroarylalkyl or —CH₂R³ group, R³ being an alkenyl or alkynyl group, or $A^1$ and $A^2$ may be bound to each other to form a hetero ring which is a five to seven membered ring with one or two nitrogen atoms or with one nitrogen atom and one oxygen atom; and G represents a straight chain alkylene group having 1 to 6 carbon atoms, a branched alkylene group having 1 to 8 carbon atoms, or the following group:

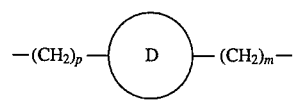

wherein p and m stand, independently, an integer from 0 to 2; and D is a cycloalkane ring; or

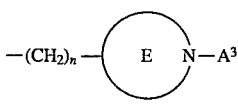

(1b)

in which n represents an integer of 0 to 2; ring E represents a 4–8 membered saturated heterocyclic ring containing a nitrogen atom; and $A^3$ represents a hydrogen atom, or an alkyl, substituted alkyl, cycloalkyl, saturated heterocyclic, cycloalkylalkyl, cycloalkenylalkyl, aralkyl, substituted aralkyl, heteroarylalkyl, substituted heteroarylalkyl or —$CH_2R^3$ group, $R^3$ being an alkenyl or alkynyl group, or may be bound to the ring E to form a quinuclidin-3-yl or guinuclidin-4-yl; or when Z represents a group represented by the following formula:

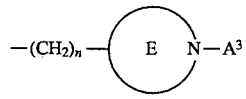

in which n, ring E and $A^3$ have the same meanings as above, the ring W may be a benzene ring; or a pharmaceutically acceptable acid addition salt or quaternary ammonium salt thereof.

5. A compound according to claim 4, wherein the ring W is a benzene or pyridine ring.

6. A compound according to claim 5, wherein Y is a phenyl or substituted phenyl group.

7. A compound according to claim 6, wherein $R^1$ is a hydrogen atom.

8. A compound according to claim 4, 5, 6 or 7, wherein the ring W is a pyridine ring.

* * * * *